United States Patent
Castelli et al.

(10) Patent No.: US 10,525,045 B2
(45) Date of Patent: *Jan. 7, 2020

(54) DOSING REGIMENS FOR THE TREATMENT OF LYSOSOMAL STORAGE DISEASES USING PHARMACOLOGICAL CHAPERONES

(71) Applicant: Amicus Therapeutics, Inc., Cranbury, NJ (US)

(72) Inventors: Jeff Castelli, New Hope, PA (US); David J. Lockhart, Emerald Hills, CA (US)

(73) Assignee: Amicus Therapeutics, Inc., Cranbury, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 16/011,068

(22) Filed: Jun. 18, 2018

(65) Prior Publication Data

US 2018/0360813 A1 Dec. 20, 2018

Related U.S. Application Data

(60) Continuation of application No. 15/213,920, filed on Jul. 19, 2016, now Pat. No. 9,999,618, which is a continuation-in-part of application No. 14/713,821, filed on May 15, 2015, now abandoned, which is a division of application No. 12/597,238, filed as application No. PCT/US2008/061764 on Apr. 28, 2008, now Pat. No. 9,056,101.

(60) Provisional application No. 60/914,288, filed on Apr. 26, 2007, provisional application No. 61/014,744, filed on Dec. 18, 2007, provisional application No. 61/028,105, filed on Feb. 12, 2008.

(51) Int. Cl.
| | | |
|---|---|---|
| *A01N 43/04* | (2006.01) | |
| *A61K 31/70* | (2006.01) | |
| *A61K 31/445* | (2006.01) | |
| *A61K 31/45* | (2006.01) | |
| *A61K 31/7008* | (2006.01) | |

(52) U.S. Cl.
CPC ............ *A61K 31/445* (2013.01); *A61K 31/45* (2013.01); *A61K 31/7008* (2013.01)

(58) Field of Classification Search
None
See application file for complete search history.

(56) References Cited

U.S. PATENT DOCUMENTS

| | | | |
|---|---|---|---|
| 5,900,360 | A | 5/1999 | Welch et al. |
| 6,270,954 | B1 | 8/2001 | Welch et al. |
| 6,274,597 | B1 | 8/2001 | Fan et al. |
| 6,541,195 | B2 | 4/2003 | Welch et al. |
| 6,583,158 | B1 | 6/2003 | Fan et al. |
| 6,589,964 | B2 | 7/2003 | Fan et al. |
| 6,599,919 | B2 * | 7/2003 | Fan .................. A61K 31/445 435/208 |
| 6,774,135 | B2 | 8/2004 | Fan et al. |
| 6,916,829 | B2 | 7/2005 | Fan et al. |
| 7,141,582 | B2 | 11/2006 | Fan et al. |
| 2004/0180419 | A1 | 9/2004 | Fan |
| 2005/0137223 | A1 | 6/2005 | Fan et al. |
| 2006/0287358 | A1 | 12/2006 | Wustman |
| 2010/0004156 | A1 | 1/2010 | Kaushal et al. |

FOREIGN PATENT DOCUMENTS

| | | |
|---|---|---|
| AU | 2015230773 A1 | 12/2015 |
| CA | 2086413 A1 | 12/1991 |
| JP | 2013255488 A | 12/2013 |
| WO | 90/11353 A1 | 10/1990 |
| WO | 2004/074450 A2 | 9/2004 |
| WO | 2004/103368 A1 | 12/2004 |
| WO | 2006/125141 A2 | 11/2006 |
| WO | 2007/137072 A2 | 11/2007 |
| WO | 2008/134628 A1 | 3/2008 |
| WO | 2008/121826 A2 | 10/2008 |

OTHER PUBLICATIONS

Pastores et al. Expert Opinion on Emerging Drugs (2005), vol. 10, p. 891-902.*
Giraldo et al. Haematologica (2009), vol. 94, pp. 1771-1775.*
Extended European Search Report for EP 08 74 7020 dated Sep. 30, 2010, 3 pages.
Final Office Action in U.S. Appl. No. 11/749,512, dated Jun. 16, 2010, 13 pages.
Final Office Action in U.S. Appl. No. 12/966,904, dated Jan. 12, 2012, 10 pages.
Final Office Action in U.S. Appl. No. 13/445,338, dated Sep. 11, 2013, 9 pages.
Non-Final Office Action in U.S. Appl. No. 11/749,512, dated Nov. 18, 2009, 10 pages.
Non-Final Office Action in U.S. Appl. No. 12/966,904, dated May 17, 2011, 11 pages.
Non-Final Office Action in U.S. Appl. No. 13/445,338, dated Feb. 5, 2013, 7 pages.
Non-Final Office Action in U.S. Appl. No. 14/713,821 dated Mar. 15, 2016, 10 pages.
PCT International Search Report for PCT/US08/61764 dated Oct. 7, 2008, 2 pages.
Supplemental European Search Report in EP 07797506.8, dated Feb. 15, 2010, 4 pages.
Supplemental European Search Report in EP 08747020.9, dated Aug. 10, 2010, 3 pages.
Andersson, Hans C., et al., "Individualization of Long-Term Enzyme Replacement Therapy for Gaucher Disease", Genetics in Medicine, 2005, vol. 7, No. 2, pp. 105-110.
Bishop, et al., "Human Alpha-Galactosidase A: Nucleotide Seqence of a cDNA Clone Encoding the Mature Enzyme", Proc. Natl. Acad. Sci. USA vol. 83, 1986, pp. 4859-4863.

(Continued)

*Primary Examiner* — Patrick T Lewis
(74) *Attorney, Agent, or Firm* — Servilla Whitney LLC

(57) ABSTRACT

The present invention provides dosing regimens for administering pharmacological chaperones to a subject in need thereof. The dosing regimens can be used to treat disorders caused by improper protein misfolding, such as lysosomal storage disorders.

18 Claims, 46 Drawing Sheets

(56) References Cited

OTHER PUBLICATIONS

Bishop, et al., "Molecular Genetics", Am. J. Hum. Genet. vol. 37, 1985, p. A144.
Brady, et al., "Enzymatic Defect in Fabry's Disease. Ceramidetrihexosidase Deficiency", N. Engl. J. Med. vol. 276, 1967, pp. 1163-1167.
Branum, et al., "Effect of Two Anticoagulants on Leukocyte Yield and Function, and on Lysosomal Enzyme Activity", Clin. Chem. vol. 34 No. 1, 1988, pp. 110-113.
Brooks, "Getting Into the Fold", Nature Chemical Biology 2007, vol. 3, No. 2, pp. 84-85.
Brown, et al., "Strategies for Correction the Delta F508 CFTR Protein-Folding Defect", Journal of Bioenergetics and Biomembranes vol. 29 No. 5, 1997, pp. 491-502.
Butters, Expert Opin. Pharmacother., 2007, vol. 8, No. 4,, pp. 427-435.
Calhoun, et al., "Fabry Disease: Isolation of a cDNA Clone Encoding Human Apha-Calactosidase A", Proc. Natl. Acad. Sci. USA vol. 82, 1985, pp. 7364-7368.
Davies, el al., "Fabry Disease: Fourteen Alpha-Galactosidase A Mutations in Unrelated Families From the United Kingdom and Other European Countries", Eur. J. Hum. Genet. vol. 4, 1996, pp. 219-224.
Desnick, et al., "Metabolic and Molecular Bases of Inherited Disease", Scriver, et al. (eds.) 8th ed., Graw-Hill, New York, 2001, pp. 3733-3774.
Eng, et al., "Fabry Disease: Thirty-Five Mutations in the Alpha-Galactosidase A Gene in Patients with Classic and Variant Phenotypes", Mol. Med. vol. 3, 1997, pp. 174-182.
Eng, et al., "Nature and Frequency of Mutations in the Alpha-Galactosidase A Gene That Cause Fabry Disease", Am. J. Hum. Genet. vol. 53, 1993, pp. 1186-1197.
Fan, et al., "A contradictory treatment for lysosomal storage disorders: inhibitors enhance mutant enzyme activity", Trends in Pharm. Sci. vol. 24 No. 7, Jul. 2003, pp. 355-360.
Fan, et al., "Accelerated transport and maturation of lysosomal alpha-galactosidase A in Fabry lymphoblasts by an enzyme inhibitor", Nat. Med. vol. 5, No. 1 (1999), pp. 112-115.
Frustaci, et al., "Improvement in Cardiac Function in the Cardiac Variant of Fabry's Disease with Galactose-Infusion Therapy", New England Journal of Medicine, 2001, vol. 345, No. 1, pp. 25-32.
Fuller, et al., "Urinary Lipid Profiling for the Identification of Fabry Hemizygotes and Heterozygotes", Clinical Chemistry vol. 51, 2005, pp. 688-694.
Ishii, et al., "Aggregation of the Inactive Form of Human alpha-Galactosidase in the Endoplasmic Reticulum", Biochem. Biophys. Res. Comm. vol. 220, 1996, pp. 813-815.
Ishii, et al., "Transgenic mouse expressing human mutant a-galactosidase A in an endogenous enzyme deficient background: a biochemical animal model for studying active-site specific chaperone therapy for Fabry disease", Biochimica et Biophysica Acta, vol. 1690, No. 3, (2004), pp. 250-257.
Kornreich, et al., "Nucleotide Sequence of the Human Alpha-Galactosidase A Gene", Nucleic Acids Res. vol. 17, 1989, pp. 3301-3302.
Kusiak, et al., "Purification and Properties of the Two Major Isozymes of Apha-Galactosidase from Human Placenta", J. Biol. Chem. Vo. 253, 1978, pp. 184-190.
Mayes, et al., "Differential Assay for Lysosomal Alpha-Galactosidases in Human Tissues and its Application to Fabry's Diesease", Clin. Chim. Acta vol. 112 No. 2, 1981, pp. 247-251.
Nakao, et al., "An Atypical Variant of Fabry's Disease in Men with Left Ventricular Hypertrophy", N. Engl. J. Med. vol. 333, 1995, pp. 288-293.
NCT00214500 on Sep. 21, 2005: https://clinicaltrials.gov/archive/NCT00214500/2005_09_21, Sep. 21, 2005, https://clinicaltrials.gov/archive/NCT00214500/2005_09_21, 1-3.
NCT00283933 on Jan. 30, 2006: ClinicalTrials.gov Archive, Jan. 30, 2006, https://clinicaltrials.gov/archive/NCT00283933/2006_01_30, 1-3.
NCT00283959 on Jan. 30, 2006: ClinicalTrials.gov Archive, Jan. 30, 2006, https://clinicaltrials.gov/archive/NCT00283959/2006_01_30, 1-3.
NCT00304512 on Mar. 17, 2006: ClinicalTrials.gov Archive, Mar. 17, 2006, https://clinicaltrials.gov/archive/NCT00304512/2006_03_17, 1-4.
Park, et al., "Long-Term Correction of Globotriaosylceramide Storage in Fabry Mice by Recombinant Adeno-Associated Virus-Mediated Gene Transfer", Proc. Natl. Acad. Sci. USA vol. 100, 2003, pp. 3450-3454.
Sawkar, et al., "Gaucher Disease-Associated Glucocerebrosidases Show Mutation-Dependent Chemical Chaperoning Profiles", Chemistry & Biology, vol. 12, Nov. 2005, pp. 1235-1244.
Sawkar, et al., "Therapeutic Strategies to Ameliorate Lysosomal Storage Disorders—A Focus on Gaucher Disease", Cell. Mol. Life Sci. 63 (2006), pp. 1179-1192.
Shin, et al., "Prediction of Response of Mutated alpha-Galactosidase A to a Pharmacological Chaperone", Pharmacogenet Genomics, vol. 18, No. 9, Sep. 2008, pp. 773-780.
Shin, et al., "Screening for Pharmacological Chaperones in Fabry Disease", Materials and Methods vol. 359, 2007, pp. 168-173.
Steet, et al., "The iminosugar isofagomine increases the activity of N370S mutant acid beta-glucosidase in Gaucher fibroblasts by several mechanisms", PNAS, 2006, vol. 103, No. 37, pp. 13813-13818.
Tsuji, et al., "Signal Sequence and DNA-Mediated Expression of Human Lysosomal Alpha-Galactosidase A", Eur. J. Biochem. vol. 165, 1987, pp. 275-280.
Weinberg, "Effect of Shipment, Storage, Anticoagulant, and Cell Separation on Lymphocyte Proliferation Assays for Human Immunodeficiency Virus-Infected Patients", Clin. Diagn. Lab. Immunol. vol. 5 No. 6, 1998, pp. 804-807.
Weinreb, et al., "Guidance on the Use of Miglustat for Treating Patients with Type 1 Gaucher Disease", American Journal of Hematology 80, 2005, pp. 223-229.
Welch, et al., "Influence of Molecular and Chemical Chaperones on Protrein Folding", Cell Stress and Chaperones vol. 1 No. 2, 1996, pp. 109-115.
Yam, et al., "A synthetic chaperone corrects the trafficking defect and disease phenotype in a protein misfolding disorder", The FASB Journal, 2004, pp. 12-18.
Yam, et al., "Pharmacological chaperone corrects lysosomal storage in Fabry disease caused by trafficking-incompetent variants", American Journal of Physiology-Cell Physiology, vol. 290, No. 4, pp. C1076-C1082 (2006).
"Galafold Summary of Product Characteristics", May 2016, 45 pgs.
PCT Invitation to Pay Additional Fees and, Where Applicable, Protest Fee in PCT/US2017/042864 dated Feb. 28, 2018, 16 pgs.
PCT International Search Report and Written Opinion in PCT/US2017/042872 dated Jan. 3, 2018, 19 pages.
Giugliani, et al., "A Phase 2 study of migalastat hydrochloride in females with Fabry disease: Selection of population, safety and pharmacodynamic effects", Molecular Genetics and Metabolism, Academic Press, Amsterdam, NL, vol. 109, No. 1, Jan. 26, 2013, pp. 86-92.
Mizukoshi, et al., "Normal Values of Left Ventricular Mass Index Assessed by Transthoracic Three-Dimensional Echocardiography", Journal of the American Society of Echocardiography, vol. 29, No. 1, Jan. 2016, pp. 51-61.
Invitation to Pay Additional Fees and, Where Applicable, Protest Fee in PCT/US2017/042872 dated Oct. 11, 2017, 15 pages.
EU Clinical Trials Register, Feb. 13, 2006, https://www.clinicaltrialsregister.eu/ctr-search/triali2006-000181-36/GB, 1-4.
EU Clinical Trials Register, Oct. 17, 2005, Ilttps://www.clinicaltrialsregister.eu/ctr-search/trial/2005-004384-33/GB,1-4.
Guerard, Nicolas , et al., "Lucerastat, an Iminosugar for Substrate Reduction Therapy: Pharmacokinetics, Tolerability, and Safety in Subjects With Mild, Moderate, and Severe Renal Function Impairment", The Journal of Clinical Pharmacology, 2017, 1425-1431.
Guerard, Nicolas , et al., "Lucerastat, an Iminosugar for Substrate Reduction Therapy: Tolerability, Pharmacodynamics, and Pharmacokinetics in Patients With Fabry Disease on Enzyme Replacement", Clinical Pharmacology & Therapeutics, Apr. 2018, 703-711.

(56) References Cited

OTHER PUBLICATIONS

Guerard, N., et al., "Lucerastat, an iminosugar with potential as substrate reduction therapy for glycolipid storage disorders: safety, tolerability, and pharmacokinetics in healthy subjects", Orphanet Journal of Rare Diseases, Jan. 14, 2017, 1-10.
Non-Final Office Action in U.S. Appl. No. 16/011,063, dated Apr. 26, 2019, 21 pages.
Non-Final Office Action in U.S. Appl. No. 16/011,075, dated Apr. 26, 2019, 21 pages.
Molecular Genetics and Metabolism, 2015, vol. 114, No. 2, pp. S57.
Journal of Inherited Metabolic Disease, 2015, vol. 38, No. 1, Suppl, p. S56.

* cited by examiner

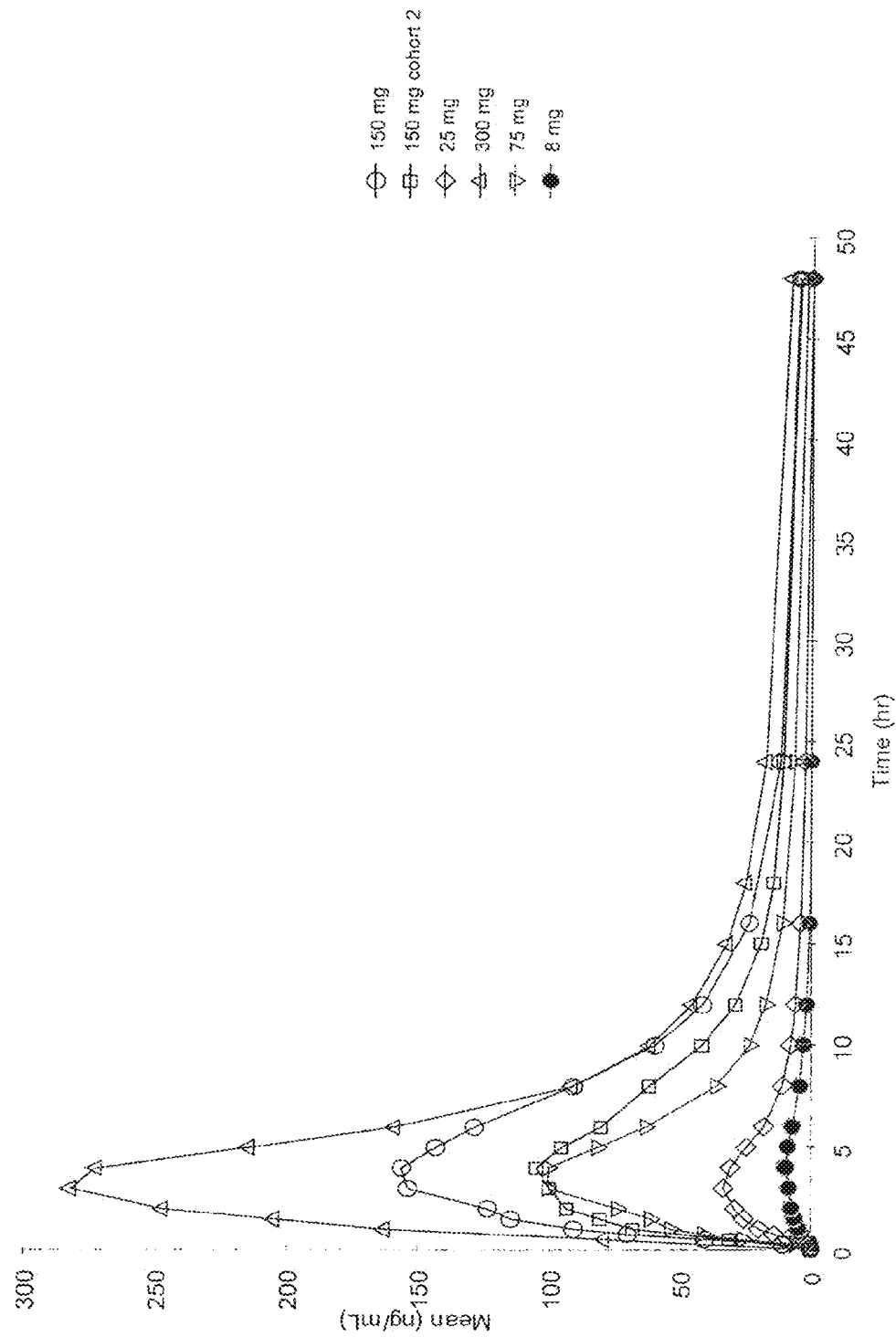

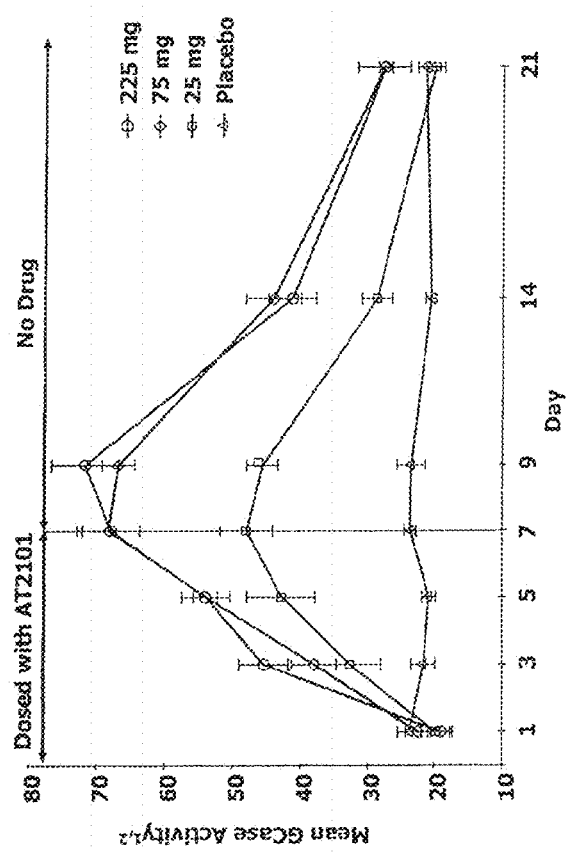

Figure 3A
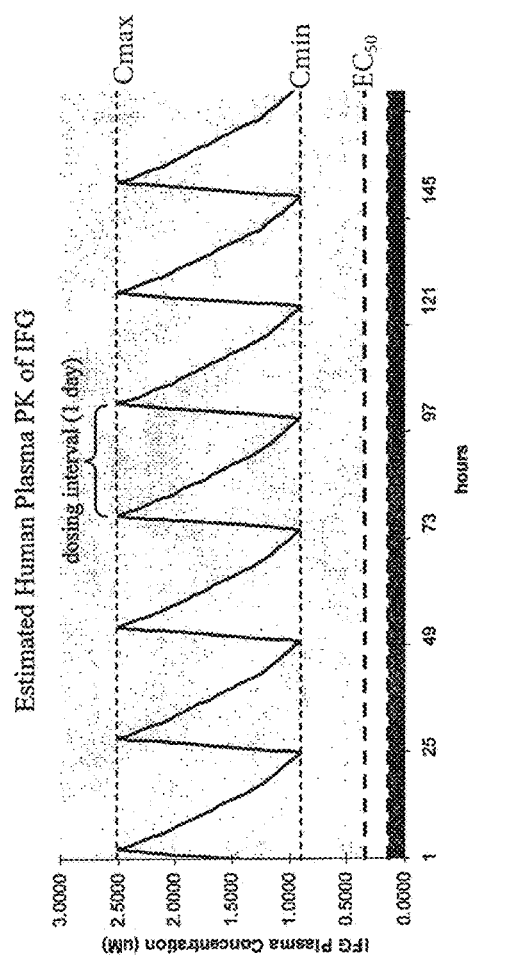
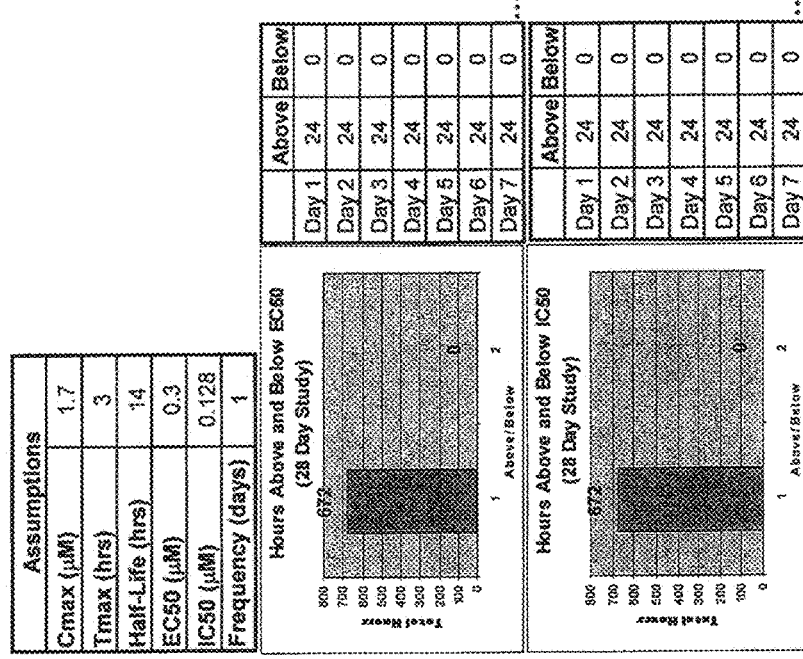

Figure 4
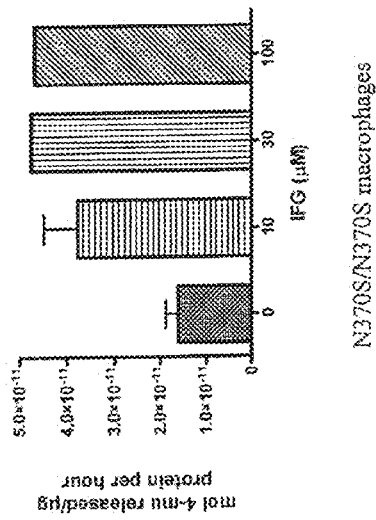
Fig. 4C.
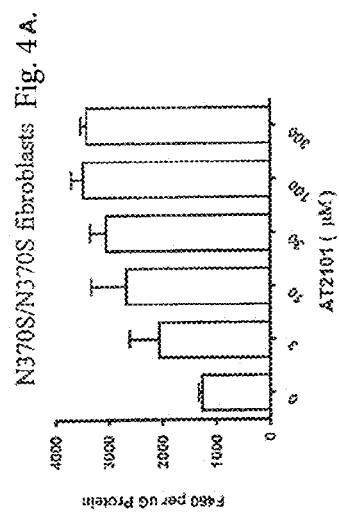
Fig. 4A.
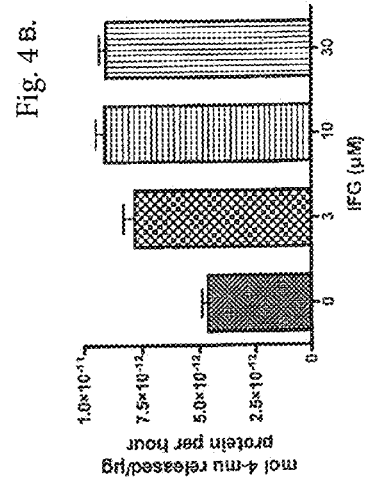
Fig. 4B.

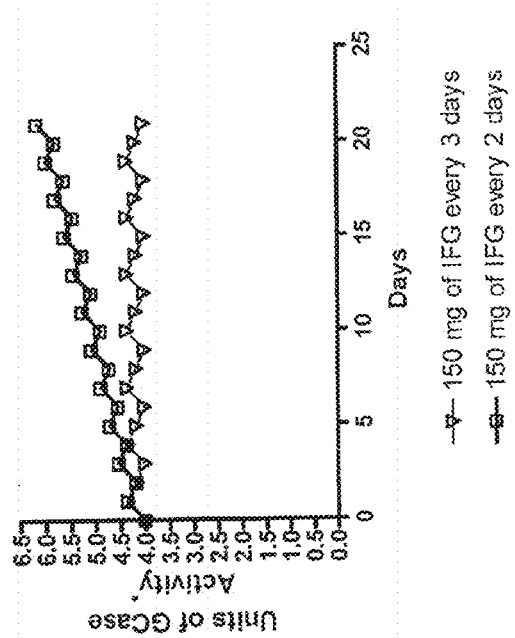

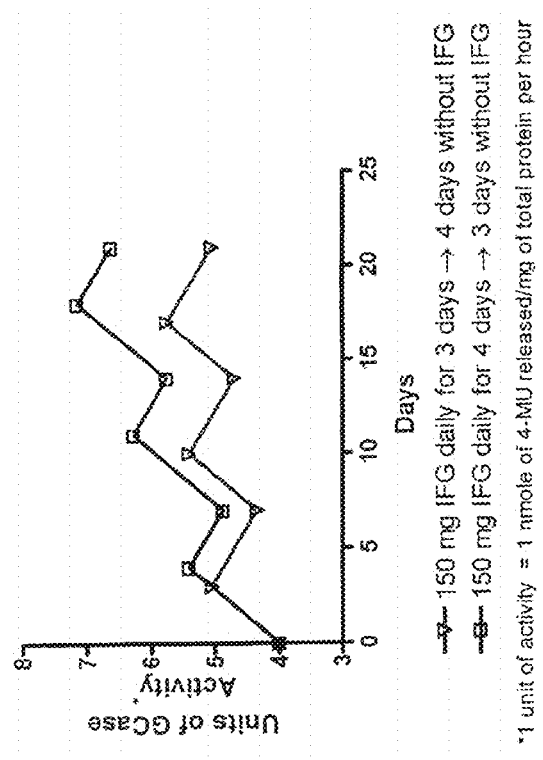

Figure 8

| Protocol | Gender | No. of Patients | Weeks | Dosing Regimen | Kidney Biopsies |
|---|---|---|---|---|---|
| Group A | Male | 9 | 12 | 25/100/250 mg bid followed by 25 mg bid and 50 mg per day | No |
| Group B | Male | 4 | 12 | 150 mg QOD | Yes |
| Group C | Male | 5 | 24 | 150 mg QOD | Yes |
| Group D | Female | 9 | 12 | 50, 150, or 250 mg QOD | Yes |

- Classic and late onset patients, ages 17-65
- 13 naïve to ERT and 14 previously on ERT (off 21-274 days)

Figure 14

Urine GL-3: Change From Baseline
Males

| WBC α-GAL response | Number with a Decrease >10% | GL-3 Change [BL to Last Visit] |
|---|---|---|
| Good | 8/11 | -38% * |
| Moderate | 1/4 | +91% |
| Non | 0/2 | +8% |

- *p < 0.05, Wilcoxon Paired Signed-Rank Test
- Fabrazyme pivotal study showed a median 23% reduction in the treated group and a 43% increase in the placebo group

Figure 15A

Kidney GL-3 (Histology) in Specific Cell Types
Males: Good Enzyme Response

| Change in Kidney Cell GL-3 from Baseline to 12 or 24 Wks | | | | |
|---|---|---|---|---|
| | Decrease | Undetectable | No change | Increase |
| Interstitial Capillaries | 1 | 1 | 1* | |
| Distal Tubules | 3 | | | 1** |
| Podocytes | | | 4 | |

- \* 1 good responder had interstitial capillary GL-3 that was scored as unchanged by EM but scored as a decrease by LM
- \*\* Patient with apparent increase in distal tubule GL-3 showed a decrease by other measures (urine GL-3, paired analysis, LC-MS on kidney biopsy)

Figure 15B

Kidney GL-3 (Histology): Paired Analysis
Males

Change in Kidney Biopsy GL-3 from Baseline to 12 or 24 Wks

|  | Decrease | No change | Increase |
|---|---|---|---|
| Males, good enzyme response | 2 | 2 |  |
| Males, moderate enzyme response | 2 |  |  |
| Males, no enzyme response | 1 |  | 1 |

- For each blinded pair, biopsies were scored as better, worse, or equivalent in terms of overall GL-3 load

Figure 16

Kidney Biopsy GL-3 (Mass Spec)
Males

| WBC α-GAL response | Number with a decrease >10% | Kidney GL-3 Change [BL to Last Visit] |
|---|---|---|
| Good | 3/4 | -28% |
| Moderate | 0/2 | 150% |
| Non | 1/2 | 3% |

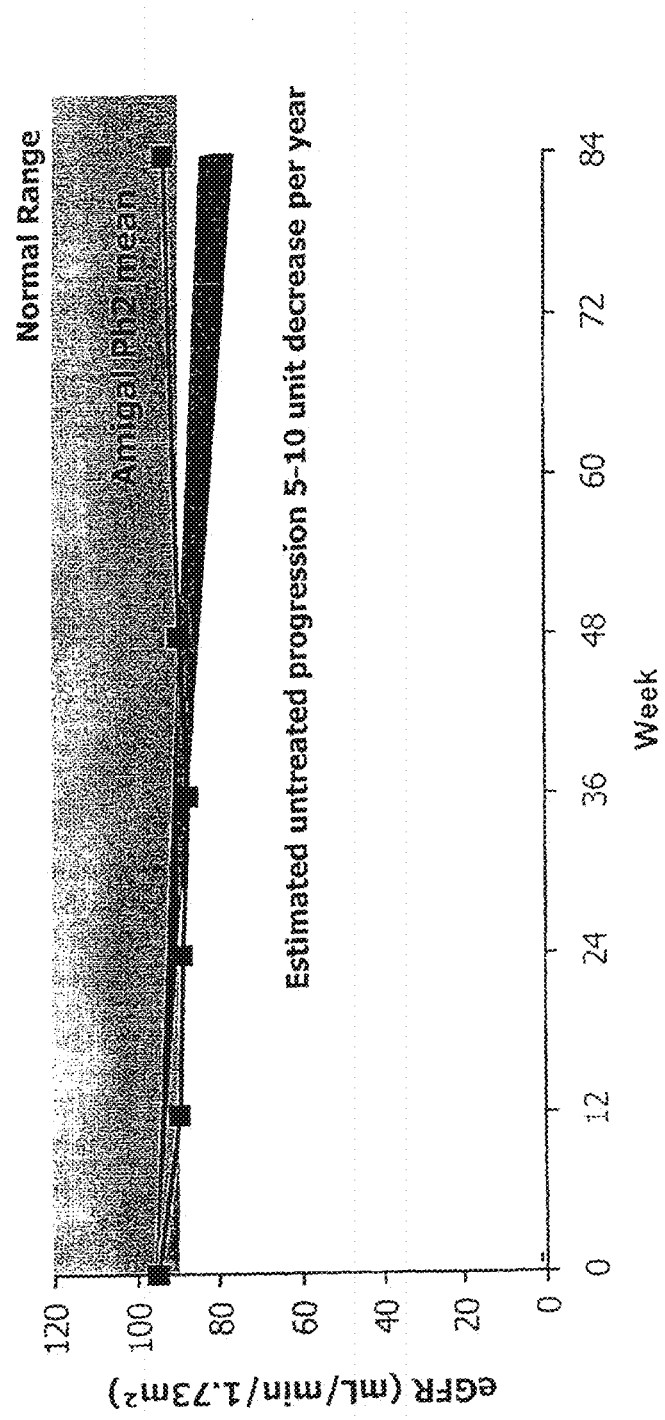

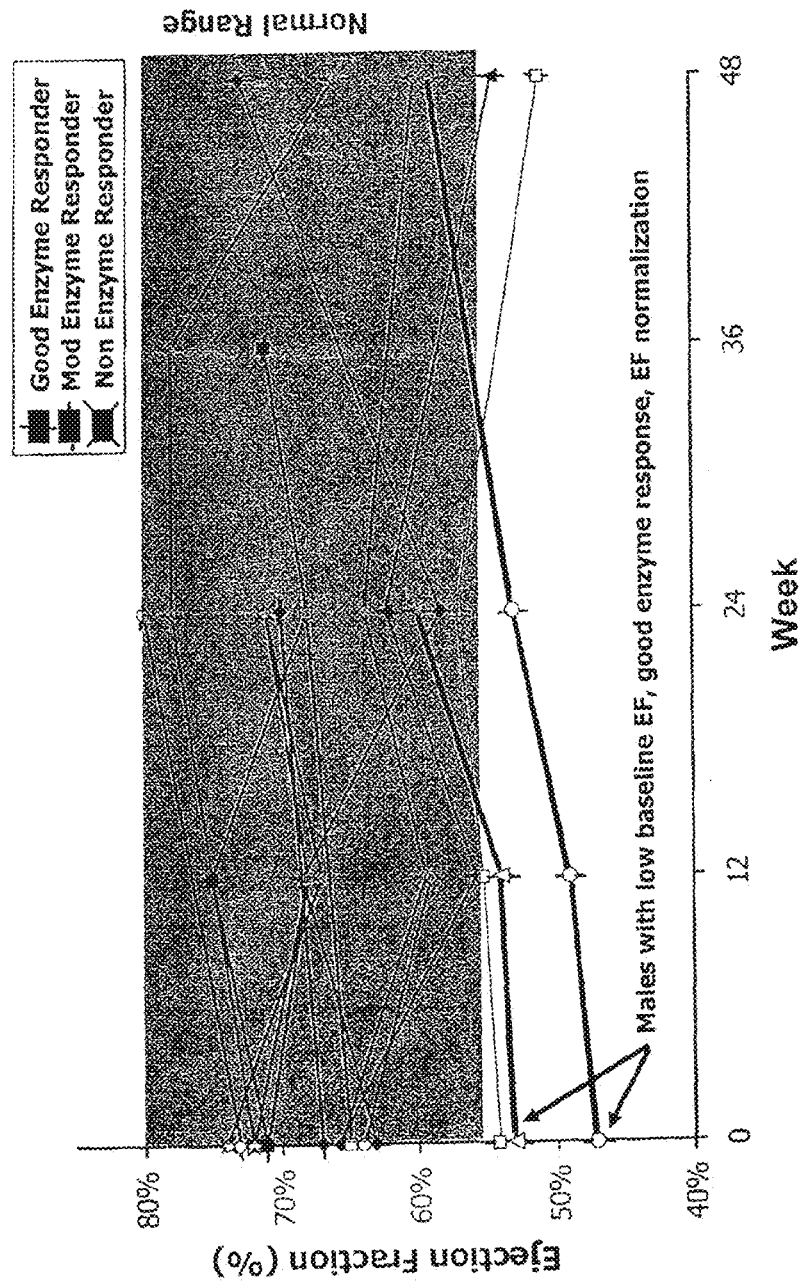

Figure 19

Self-Reported Fabry Symptoms
Males

Self-Reported Change in Fabry Symptoms
[Baseline to the Last Reported On-Treatment Value]

| | Improvement | No Change or Worsening |
|---|---|---|
| Males, good enzyme response | [7]<br>• 1 has improved GI and pain symptoms<br>• 1 reports ability to walk, drive and sleep more<br>• 1 has improved sweating and less pain<br>• 1 is feeling better than while on ERT with more energy<br>• 1 is feeling better overall<br>• 2 have increased sweating | [2]<br>• 1 reports no change and has libido concerns<br>• 1 reports no change |
| Males, moderate or no enzyme response | [1]<br>• 1 reports sweating a little more but pain still present | [3]<br>• 3 report no changes |

Figure 20

Urine GL-3: Change From Baseline Females

| WBC α-GAL response | Number with a Decrease >10% | Urine GL-3 Change [BL to Last Visit] |
|---|---|---|
| Expected Good | 3/5 | -20% |
| Expected Non | 1/4 | +184% |

Figure 21

Kidney Biopsy GL-3 (Mass Spec)
Females

| WBC α-GAL response | Number with a Decrease >10% | Urine GL-3 Change [BL to Last Visit] |
|---|---|---|
| Expected Good | 2/5 | -20% |
| Expected Non | 0/4 | +65% |

Figure 22

Self-Reported Fabry Symptoms
Females

Self-Reported Change in Fabry Symptoms
[Baseline to the Last Reported On-Treatment Value]

| | Improvement | No Change or Worsening |
|---|---|---|
| Females, expected good enzyme response | [4]<br>• 1 has less pain and more sweating<br>• 1 reports ability to walk, drive and sleep more<br>• 1 is feeling better overall<br>• 1 is feeling better overall but still has some pain | [1]<br>• 1 had no change |
| Females, no expected enzyme response | [1]<br>• 1 has less pain | [3]<br>• 1 reports being anxious, depressed and difficulty sleeping<br>• 1 says pain is still present and is not feeling as good as when on ERT<br>• 1 had no change |

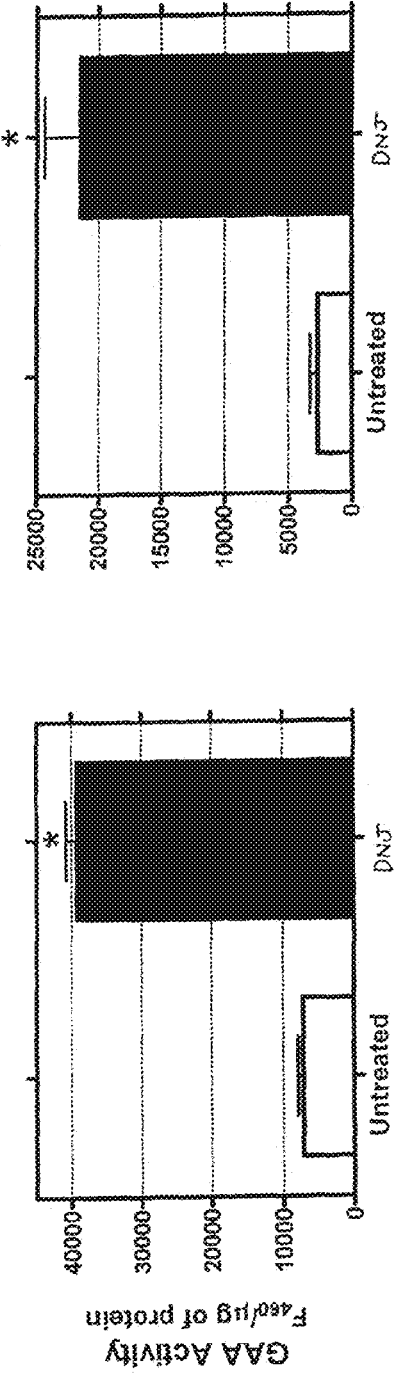

Figure 26 Cont.

| Relative GLA Increase | # of Missense Genotypes (n=69) |
|---|---|
| <1.3 | 28 (37%) |
| 1.3 – 2.0 | 3 (4%) |
| 2.0 – 3.0 | 8 (11%) |
| 3.1 – 6.0 | 12 (16%) |
| 6.1 – 10.0 | 16 (21%) |
| >10.1 | 8 (11%) |
| ≥1.3/Total | 47/75 (63%) |

- 75 missense cell lines tested
- 63% were enhanceable
- A majority associated with the classic phenotype responded (34/57; ~60%)
- 95% of mutations associated with the later-onset phenotype responded (19/20)

DOSING REGIMENS FOR THE TREATMENT OF LYSOSOMAL STORAGE DISEASES USING PHARMACOLOGICAL CHAPERONES

This application is a continuation application of U.S. application Ser. No. 15/213,920, filed Jul. 19, 2016, which is a continuation-in-part application of U.S. application Ser. No. 14/713,821, filed May 15, 2015, now abandoned, which is a divisional application of U.S. application Ser. No. 12/597,238, now U.S. Pat. No. 9,056,101, which is a National Stage Application of PCT/US2008/061764, filed Apr. 28, 2008, which claims the benefit of U.S. Provisional Application No. 60/914,288, filed Apr. 26, 2007, U.S. Provisional Application No. 61/014,744, filed Dec. 18, 2007 and U.S. Provisional Application No. 61/028,105, filed Feb. 12, 2008. The contents of each of these applications are hereby incorporated by reference in their entirety.

FIELD OF THE INVENTION

The present invention provides a dosing regimen and rationale therefore for the use of small molecule competitive inhibitors as pharmacological chaperones for the treatment of lysosomal storage diseases.

BACKGROUND

In the human body, proteins are involved in almost every aspect of cellular function. Proteins are linear strings of amino acids that fold and twist into specific three-dimensional shapes in order to function properly. Certain human diseases result from mutations that cause changes in the amino acid sequence of a protein which reduce its stability and may prevent it from folding properly. The majority of genetic mutations that lead to the production of less stable or misfolded proteins are called missense mutations. These mutations result in the substitution of a single amino acid for another in the protein. Because of this error, missense mutations often result in proteins that have a reduced level of biological activity. In addition to missense mutations, there are also other types of mutations that can result in proteins with reduced biological activity.

Proteins generally fold in a specific region of the cell known as the endoplasmic reticulum, or ER. The cell has quality control mechanisms that ensure that proteins are folded into their correct three-dimensional shape before they can move from the ER to the appropriate destination in the cell, a process generally referred to as protein trafficking. Misfolded proteins are often eliminated by the quality control mechanisms after initially being retained in the ER. In certain instances, misfolded proteins can accumulate in the ER before being eliminated.

The retention of misfolded proteins in the ER interrupts their proper trafficking, and the resulting reduced biological activity can lead to impaired cellular function and ultimately to disease. In addition, the accumulation of misfolded proteins in the ER may lead to various types of stress on cells, which may also contribute to cellular dysfunction and disease.

Lysosomal storage diseases (LSDs) are characterized by deficiencies of lysosomal enzymes due to mutations in the genes encoding the lysosomal enzymes. This results in the pathologic accumulation of substrates of those enzymes, which include lipids, carbohydrates, and polysaccharides. There are about fifty known LSDs to date, which include Gaucher disease, Fabry disease, Pompe disease, Tay Sachs disease and the mucopolysaccharidoses (MPS). Most LSDs are inherited as an autosomal recessive trait, although males with Fabry disease and MPS II are hemizygotes because the disease genes are encoded on the X chromosome. For most LSDs, there is no available treatment beyond symptomatic management. For several LSDs, including Gaucher, Fabry, Pompe, and MPS I and VI, enzyme replacement therapy (ERT) using recombinant enzymes is available. For Gaucher disease, substrate reduction therapy (SRT) also is available in limited situations. SRT employs a small molecule inhibitor of an enzyme required for the synthesis of glucosylceramide (the GD substrate). The goal of SRT is to reduce production of the substrate and reduce pathologic accumulation.

Although there are many different mutant genotypes associated with each LSD, some of the mutations, including some of the most prevalent mutations, are missense mutations which can lead to the production of a less stable enzyme. These less stable enzymes are sometimes prematurely degraded by the ER-associated degradation pathway. This results in the enzyme deficiency in the lysosome, and the pathologic accumulation of substrate. Such mutant enzymes are sometimes referred to in the pertinent art as "folding mutants" or "conformational mutants."

It has previously been shown that the binding of small molecule inhibitors of enzymes associated with LSDs can increase the stability of both mutant enzyme and the corresponding wild-type enzyme (see U.S. Pat. Nos. 6,274,597; 6,583,158; 6,589,964; 6,599,919; 6,916,829, and 7,141,582 all incorporated herein by reference). In particular, it was discovered that administration of small molecule derivatives of glucose and galactose, which are specific, selective competitive inhibitors for several target lysosomal enzymes, effectively increased the stability of the enzymes in cells in vitro and, thus, increased trafficking of the enzymes to the lysosome. Thus, by increasing the amount of enzyme in the lysosome, hydrolysis of the enzyme substrates is expected to increase. The original theory behind this strategy was as follows: since the mutant enzyme protein is unstable in the ER (Ishii et al., Biochem. Biophys. Res. Comm. 1996; 220: 812-815), the enzyme protein is retarded in the normal transport pathway (ER→Golgi apparatus→endosomes→lysosome) and prematurely degraded. Therefore, a compound which binds to and increases the stability of a mutant enzyme, may serve as a "chaperone" for the enzyme and increase the amount that can exit the ER and move to the lysosomes. In addition, because the folding and trafficking of some wild-type proteins is incomplete, with up to 70% of some wild-type proteins being degraded in some instances prior to reaching their final cellular location, the chaperones can be used to stabilize wild-type enzymes and increase the amount of enzyme which can exit the ER and be trafficked to lysosomes.

Since some enzyme inhibitors are known to bind specifically to the catalytic center of the enzyme (the "active site"), resulting in stabilization of enzyme conformation in vitro, these inhibitors were proposed, somewhat paradoxically, to be effective chaperones that could help restore exit from the ER, trafficking to the lysosomes, hydrolytic activity. These specific pharmacological chaperones were designated "active site-specific chaperones (ASSCs)" or "specific pharmacological chaperones" since they bound in the active site of the enzyme in a specific fashion. Pharmacological chaperone therapy has potential advantages over ERT since a small molecule can be orally administered and may have superior biodistribution compared to protein-based therapies.

Currently, three pharmacological chaperones are in human clinical trials for Fabry disease, Gaucher disease, and Pompe disease. Since the chaperones are competitive inhibitors of the enzymes which are deficient in these diseases, appropriate dosing regimens must be designed which will result in a net increase of cellular enzyme activity and not sustained inhibition of the already-deficient enzyme.

BRIEF DESCRIPTION OF THE DRAWINGS

FIG. 1 depicts plasma PK results following administration of isofagomine tartrate to healthy human volunteers.

FIG. 2 depicts pharmacodynamic results following administration of isofagomine tartrate to healthy human volunteers.

FIGS. 3A, 3B, and 3C shows the results of in silico modeling of drug plasma concentrations above and below the $EC_{50}$ and $IC_{50}$ over 28 days following daily administration of IFG. In FIG. 3A, 150 mg of IFG was modeled. In FIG. 3B, 25 mg of IFG was modeled. In FIG. 3C, 150 mg of IFG every 4 days was modeled.

FIGS. 4A, 4B, and 4C show in vitro increases in GCase activity as measured using an artificial substrate in cell lysates following treatment with IFG at different concentrations for 5 days. FIG. 4A depicts GCase activity in fibroblasts; FIG. 4B depicts GCase activity in lymphoblasts; and FIG. 4C depicts GCase activity in macrophages.

FIG. 5A shows the results of in silico modeling of GCase accumulation rates following administration of 150 mg of IFG every 2 or 3 days. FIG. 5C shows the expected results of daily administration of 150 mg of IFG every 3 days, followed by 4 days "drug free," and also shows the expected results of daily administration of 150 mg of IFG every 4 days, followed by 3 days "drug free."

FIG. 8 is a table summarizing four dosing regimens described in Example 6.

FIG. 14 is a table summarizing urine GL-3 change from baseline as described in Example 6.

FIGS. 15A and 15B are tables summarizing GL-3 Histology in specific cell types as described in Example 6.

FIG. 16 is a table summarizing GL-3 kidney biopsy as described in Example 6.

FIGS. 17A and 17B is a graph demonstrating eGFR levels at 48 weeks or more as described in Example 6.

FIG. 18 is graph demonstrating ejection fraction as described in Example 6.

FIG. 19 is table summarizing self-reported Fabry symptoms.

FIG. 20 is a table summarizing urine GL-3 change from Baseline for female patients as described in Example 6.

FIG. 21 is a table summarizing kidney biopsy GL-3 data in Females.

FIG. 22 is a table summarizing female self-reported Fabry symptoms.

FIG. 23 is a table demonstrating the effect of DNJ on Normal Mouse GAA Activity as described in Example 7.

FIG. 25 is a picture of renal tubule sections and cardiac sections as described in Example 8.

changes in volume fraction of GL-3 inclusions in podocytes and (C) changes in GL-3 inclusion volume, as described in Example 15.

Figure 39:
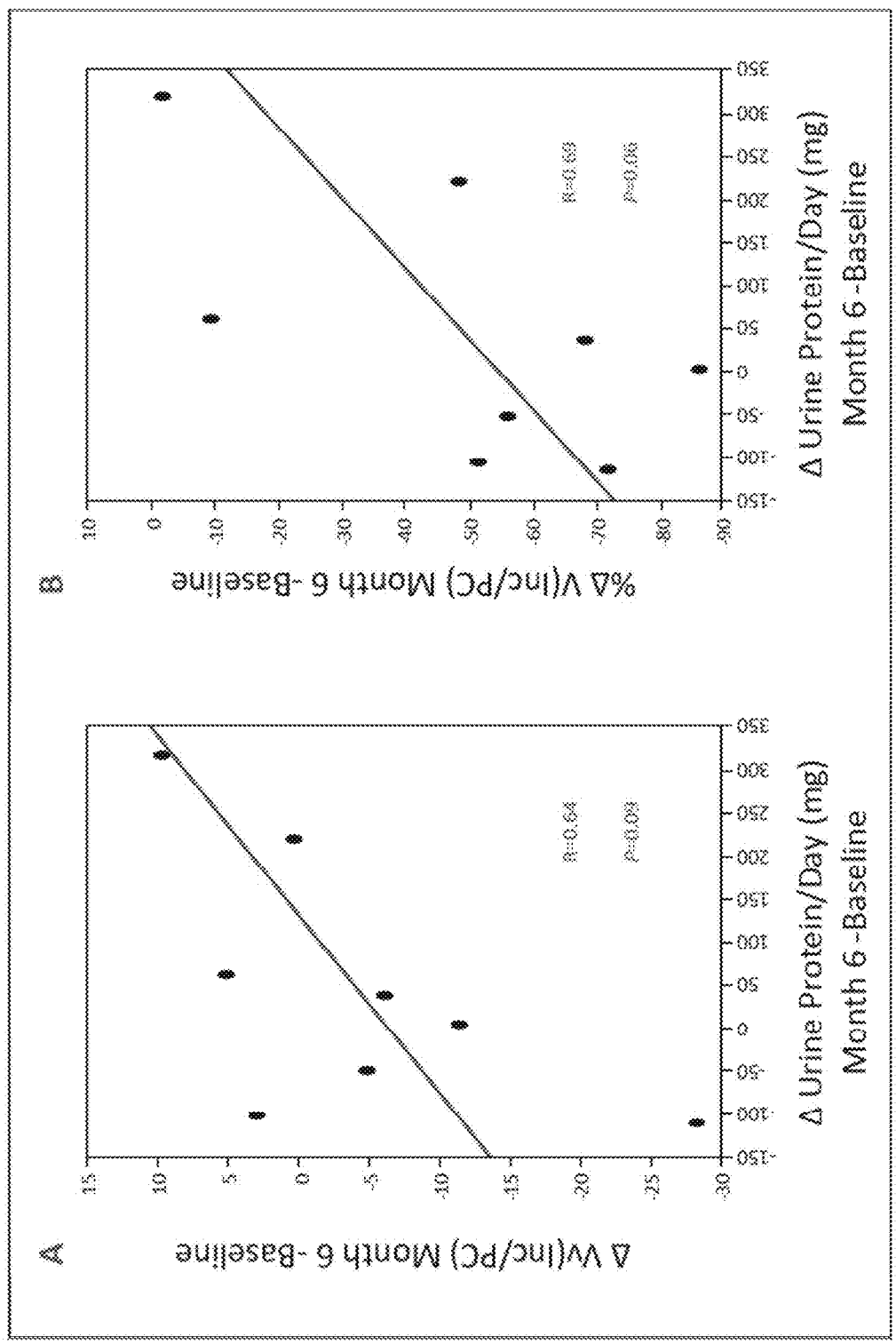

FIG. 39 shows independent comparisons of change in 24-hour urine protein with (A) change in volume fraction of GL-3 inclusions in podocytes and (B) GL-3 inclusion volume, as described in Example 15.

SUMMARY OF THE INVENTION

The present invention provides dosing regimens for administering specific pharmacological chaperones for the treatment of diseases associated with misfolded proteins (e.g. lysosomal storage disorders) and diseases which may be treated or ameliorated with the pharmacological chaperones described herein.

In a specific embodiment, dosing regimens are provided for administration of isofagomine or a pharmacologically acceptable salt of isofagomine to a patient for the treatment of Gaucher disease.

In one embodiment, from about 75 mg to about 300 mg of a pharmacological chaperone (e.g. isofagomine) is orally administered once daily for about 4 to about 10 days, followed by orally administering a maintenance dose of about 75 to 225 mg of the pharmacological chaperone once every about 3 to about 8 days.

In a further embodiment, the daily dose of pharmacological chaperone administered is about 125 to 225 mg/day (e.g. about 150 mg/day), and is administered for about 5 to about 8 days (e.g. about 7 days).

In a further embodiment, the maintenance dose of the pharmacological chaperone (e.g. isofagomine) administered is about 125 mg to about 175 mg, and is administered about every 4-7 days. In yet a further embodiment, the maintenance dose administered is about 150 mg, which is administered every 4 days. In an alternate, embodiment, the maintenance dose administered is about 150 mg, which dose is administered every 7 days.

In a specific embodiment, the present invention provides a method of administering isofagomine or a pharmacologically acceptable salt to a patient for the treatment of Gaucher disease by orally administering about 150 mg of isofagomine once daily for about 7 days, followed by orally administering a maintenance dose of about 150 mg of isofagomine about once every 7 days.

The present invention also provides a method of administering isofagomine or a pharmacologically acceptable salt to a patient in need thereof for the treatment of Gaucher disease, by orally administering between about 75 mg to about 300 mg about every 2-3 days.

In one embodiment, the dose of isofagomine administered is between about 125 mg to about 225 mg. In another embodiment, the dose of isofagomine administered is about 150 mg. In a specific embodiment, about 150 mg of isofagomine tartrate is administered about every 3 days.

In a particular embodiment of the invention, the isofagomine salt administered is isofagomine tartrate.

In one embodiment, from about 75 to about 300 mg of a pharmacological chaperone is orally administered once daily for about 4 to about 10 days, followed by a first washout period in which the pharmacological chaperone is not administered for about 1 to about 10 days, followed by orally administering a maintenance dose of about 75 to 300 mg of the pharmacological chaperone once every about 1 to about 8 days, followed by a second washout period in which the pharmacological chaperone is not administered for about 1 to about 10 days.

In a further embodiment, the daily dose administered is about 125 to 225 mg/day, and is administered for about 5 to about 8 days. In a still further embodiment, the daily dose administered is about 225 mg/day, and is administered for about 7 days.

In a further embodiment, the first washout period in which the pharmacological chaperone is not administered is about from about 2 days to about 8 days. In a specific embodiment, the first washout period in which the pharmacological chaperone is not administered is about 7 days.

In a further embodiment, the maintenance dose administered is from about 125 mg to about 275 mg, and is administered once a day for about 4-7 days. In yet a further embodiment, the maintenance dose administered is about 225 mg, which dose is administered once a day for about 3 days.

In an alternative embodiment, no maintenance dose is administered.

In a further embodiment, the second washout period in which the pharmacological chaperone is not administered is from about 2 days to about 8 days. In a specific embodiment, the second washout period in which the pharmacological chaperone is not administered is about 4 days. In an alternative embodiment, there is no second washout period in which no pharmacological chaperone is administered.

In a further embodiment, the daily dose and the first washout period occurs over a period of time from about 1 week to about 30 weeks, of from about 5 weeks to about 25 weeks.

In a further embodiment, the daily dose and the first washout period occurs over a period of time from about 5 weeks to about 25 weeks.

In a specific embodiment, the daily dose and the first washout period occurs over a period of time of about 24 weeks.

In an alternative embodiment, the daily dose and the first washout period occurs over a period of time of about 2 weeks.

In a further embodiment, the maintenance dose and the second washout period occurs over a period of time from about 1 week to about 30 weeks.

In a further embodiment, the daily dose and the first washout period occurs over a period of time from about 5 weeks to about 25 weeks.

In a specific embodiment, the maintenance dose and the second washout period occurs over a period of time of about 22 weeks.

In yet a further embodiment, the patient does not ingest any food (i.e. fasts) prior to and following the administration of a pharmacological chaperone for a period of between about 0.5 and about 24 hours, or from about 1 hour to about 12 hours (e.g. about 2 hours).

In a further embodiment, the pharmacological chaperone is isofagomine or a pharmacologically acceptable salt thereof (e.g. isofagomine tartrate).

In a specific embodiment, the present invention provides a method of administering isofagomine or a pharmacologically acceptable salt to a patient for the treatment of Gaucher disease by orally administering about 225 mg of isofagomine or a pharmacologically acceptable salt once daily for about 7 days, followed by a first washout period in which no isofagomine or pharmacologically acceptable salt is administered for about 7 days, followed by orally administering a maintenance dose of about 225 mg of isofagomine or pharmacologically acceptable salt once each day for about 3 days, followed by a second washout period in which no isofagomine or pharmacologically acceptable salt is administered for about 4 days, wherein the maintenance dose and the second washout period repeats for a period of 22 weeks.

In another specific embodiment, the present invention provides a method of administering isofagomine or a pharmacologically acceptable salt to a patient for the treatment of Gaucher disease by orally administering about 225 mg of isofagomine or a pharmacologically acceptable salt once daily for about 7 days, followed by a washout period in which no isofagomine or pharmacologically acceptable salt is administered for about 7 days, wherein the administration of the daily dose and the washout period repeats for a period of 24 weeks.

In a particular embodiment of the invention, the isofagomine salt administered is isofagomine tartrate.

The present invention also provides specific dosing regimens for the administration of 1-deoxygalactonojirimycin or salts thereof for the treatment of Fabry disease. The present invention also provides specific dosing regimens for the administration of 1-deoxygalactonojirimycin for reducing left ventricular mass index (LVMi) or podocyte globotriaosylceramide (GL-3) in a patient having Fabry disease. In particular embodiments, the patient has left ventricular hypertrophy (LVH) prior to initiating administration of the 1-deoxygalactonojirimycin or salt thereof.

In one embodiment of the invention, DGJ hydrochloride is orally administered daily from about 4 to about 10 days, or from about 5 to about 8 days, or for about 7 days, followed by administration of a maintenance dose about every 2 days to about every 3 days.

In this embodiment, the daily dose will be in a range from about 200 mg to about 500 mg per day, or from about 250 mg to about 300 mg per day, or about 250 mg per day.

In the foregoing embodiments, the maintenance dose administered every 2 to 3 days will be in a range from about 75 mg to about 225 mg, or, from about 100 mg to about 200 mg, or, in a specific embodiment, about 150 mg.

In another embodiment, 1-deoxygalactonojirimycin is administered daily from about 4 to about 14 days, or from about 5 to about 10 days, or in a particular embodiment, for about 7 days, at a dose in a range from about 200 mg to about 500 mg per day, or from about 250 mg to about 300 mg per day, or about 250 mg per day.

Following the 4-14 day period, a daily maintenance dose is administered which is in a range from about 25 to 50 mg, or about 25 mg per day.

In another embodiment, interval dosing about every 2-3 days is contemplated. In this embodiment, between about 50 mg to about 300 mg 1-deoxygalactonojirimycin or salt thereof is administered at each interval, or from about 125 mg to about 225 mg at each interval, or about 150 mg at each interval. In specific embodiments, DGJ hydrochloride will be administered at 50 mg, 150 mg or 250 mg every 2 days. In other specific embodiments, about 123 mg free base equivalent (FBE) of DGJ or a salt thereof is administered every 2 days, such as about 123 mg of DGJ or about 150 mg of migalastat hydrochloride.

In a further embodiment, 1-deoxygalactonojirimycin will be orally administered 50 mg per day for two weeks, followed by 200 mg per day for two weeks, followed by 500 mg per day for two weeks and followed by 50 mg per day for the duration of treatment.

DETAILED DESCRIPTION

The present invention provides dosing regimens for the administration of specific pharmacological chaperones for the treatment of a disease associated or caused by one or more misfolded proteins, for example, a lysosomal storage disorder. The dosing regimens described in this application may also be used to treat any disease or condition which may be treated or ameliorated with use of a pharmacological chaperone, including but not limited to, Parkinson's Disease, and Alzheimer's Disease. For example, specific dosing regimens of isofagomine and 1-deoxygalactonojirimycin are provided for the treatment of Gaucher disease and Fabry disease, respectively, and an in silico model is provide that can be used to predict dosing regimens for other diseases in which the pharmacological chaperone is a viable treatment option.

DEFINITIONS

"Gaucher disease" refers to Type 1, Type 2, and Type 3 Gaucher disease.

"Fabry disease" refers to classical Fabry disease, late-onset Fabry disease, and hemizygous females having mutations in the gene encoding α-galactosidase A.

"Pompe disease" or "glycogen storage disease type II" includes infantile-onset, non-classical infantile-onset, and adult-onset disease.

As used herein, the term "pharmacological chaperone," or sometimes "specific pharmacological chaperone" ("SPC"), refers to a molecule that specifically binds to a protein, such as an enzyme, and has one or more of the following effects: (i) inducing a stable molecular conformation of the protein; (ii) promoting trafficking of the protein from the ER to another cellular location, preferably a native cellular location, i.e., preventing ER-associated degradation of the protein; (iii) preventing aggregation of unstable proteins; (iv) restoring or increasing at least partial wild-type function and/or activity to the protein; and/or improving the phenotype or function of the cell harboring the protein. Thus, a pharmacological chaperone is a molecule that binds to a target protein, resulting in protein stabilization, trafficking, non-aggregation, and/or increasing activity of the protein. As used herein, this term does not refer to endogenous chaperones, such as BiP, or to non-specific agents which have demonstrated non-specific chaperone activity, such as glycerol, DMSO or deuterated water, which are sometimes called "chemical chaperones" (see Welch et al., *Cell Stress and Chaperones* 1996; 1(2):109-115; Welch et al., *Journal of Bioenergetics and Biomembranes* 1997; 29(5):491-502; U.S. Pat. Nos. 5,900,360; 6,270,954; and 6,541,195).

In various embodiments "pharmacological chaperone" or "specific pharmacological chaperone" ("SPC") includes only active-site specific chaperones that bind to an enzyme or other protein in a competitive manner. Unless stated otherwise, however, the "pharmacological chaperone" or "specific pharmacological chaperone" ("SPC") is understood to encompass chaperones that bind the enzyme in areas in addition to the active site and also encompasses chaperones that bind in both a competitive and non-competitive manner.

Unless specified otherwise, any reference to administration of a pharmacological chaperone shall refer to oral administration. Any reference to administration amounts of pharmacological chaperone shall refer to oral administration amounts of pharmacological chaperone.

As used herein, the terms "enhance protein activity" or "increase protein activity" refer to increasing the amount of polypeptide that adopts a stable conformation in a cell contacted with a pharmacological chaperone specific for the protein, relative to the amount in a cell (preferably of the same cell-type or the same cell, e.g., at an earlier time) not contacted with the pharmacological chaperone specific for the protein. In one embodiment, the cells do not express a mutant polynucleotide encoding a polypeptide that is deficient with respect to the folding and/or processing of a polypeptide in the ER. In another embodiment, the cells do express a mutant polynucleotide encoding a polypeptide e.g., a conformational mutant. Thus, the aforementioned terms also mean increasing the efficiency of transport of a wild-type polypeptide to its native location in a cell contacted with a pharmacological chaperone specific for the protein, relative to the efficiency of transport of a wild-type polypeptide in a cell (preferably of the same cell, e.g., at an earlier time, or the same cell type as a control) not contacted with the pharmacological chaperone specific for the protein.

The term "Vmax" refers to the maximum initial velocity of an enzyme catalyzed reaction, i.e., at saturating substrate levels. The term "Km" is the substrate concentration required to achieve ½ Vmax.

The term "AUC" represents a mathematical calculation to evaluate the body's total exposure over time to a given drug. In a graph plotting how concentration in the blood after dosing, the drug concentration variable lies on the y-axis and time lies on the x-axis. The area between a drug concentration curve and the x-axis for a designated time interval is the AUC. AUCs are used as a guide for dosing schedules and to compare different drugs' availability in the body.

The term "Cmax" represents the maximum plasma concentration achieved after dosing.

The term "Tmax" represents the time to maximum plasma concentration (Cmax).

The term "Ki" refers the dissociation constant of the enzyme-inhibitor complex, i.e., the concentration required to inhibit half-maximal enzyme activity. A low Ki means there is a high binding affinity of the drug to the enzyme.

The term "$EC_{50}$" refers to is the concentration of a drug which induces a desired response halfway between the baseline and maximum, i.e., the concentration at which 50% of its maximal effect is observed. According to the present invention, the $EC_{50}$ is the concentration at which half of the observed maximal increase in enzyme activity occurs under a specific set of conditions.

The term "$IC_{50}$" represents the concentration of a drug that is required for 50% enzyme inhibition in vitro in cells.

The terms "therapeutically effective dose" and "effective amount" refer to the amount of the specific pharmacological chaperone that is sufficient to result in a therapeutic response. A therapeutic response may be any response that a user (e.g., a clinician) will recognize as an effective response to the therapy, including the foregoing symptoms and surrogate clinical markers. Thus, a therapeutic response will generally be an amelioration of one or more symptoms of a disease or disorder, e.g., Gaucher disease, such as those known in the art for the disease or disorder, e.g., for Gaucher disease.

Non-limiting examples of improvements in surrogate markers for Gaucher disease are disclosed in U.S. Ser. No. 60/911,699, hereby incorporated by reference, and include increases in GCase levels or activity; increased trafficking of GCase from the ER to the lysosome; decreases in the presence of lipid-laden macrophages ("Gaucher macrophages"); decreased levels of chitotriosidase; decreased levels of liver enzymes; decreased levels of pulmonary chemokine PARC/CCL18; decreased levels of plasma α-synuclein; decreased levels of angiotensin converting enzyme (ACE) and total acid phosphatase; decreased splenomegaly and hepatomegaly, improvements in bone complications (including osteopenia, lytic lesions, pathological fractures, chronic bone pain, acute bone crises, bone infarcts, osteonecrosis, and skeletal deformities), improvements in immunological defects such as anemia, thrombocytopenia, leukopenia, hypergammaglobulinemia, increased amount of T-lymphocytes in the spleen, decreased B cell hyperproliferation and plasmacytosis, decreased levels of inflammatory cytokines including TNF-α, IL-1β, IL-6, IL-8, IL-17, MIP-1α and VEGF, improvements in neutrophil chemotaxis; decreased pulmonary hypertension; and decreased levels of bone-specific alkaline phosphatase, improvements in neurological symptoms such as horizontal gaze, myoclonic movements, corneal opacity, ataxia, dementia, spasticity; seizures, auditory impairment; cognitive impairment, and neurodegeneration.

Non-limiting examples of improvements in surrogate markers for Fabry disease include increases in α-GAL levels or activity in cells (e.g., fibroblasts) and tissue; reductions in of GL-3 accumulation; decreased plasma concentrations of homocysteine and vascular cell adhesion molecule-1 (VCAM-1); decreased GL-3 accumulation within myocardial cells and valvular fibrocytes; reduction in cardiac hypertrophy (especially of the left ventricle), amelioration of valvular insufficiency, and arrhythmias; amelioration of proteinuria; decreased urinary concentrations of lipids such as CTH, lactosylceramide, ceramide, and increased urinary concentrations of glucosylceramide and sphingomyelin (Fuller et al., *Clinical Chemistry*. 2005; 51: 688-694); the absence of laminated inclusion bodies (Zebra bodies) in glomerular epithelial cells; improvements in renal function; mitigation of hypohidrosis; the absence of angiokeratomas; and improvements hearing abnormalities such as high frequency sensorineural hearing loss progressive hearing loss, sudden deafness, or tinnitus. Improvements in neurological symptoms include prevention of transient ischemic attack (TIA) or stroke; and amelioration of neuropathic pain manifesting itself as acroparaesthesia (burning or tingling in extremities). Accordingly, the dosing regimens described herein can be used to improve any of these surrogate markers, such as reducing left ventricular mass index (LVMi) or reducing GL-3 accumulation in renal podocytes.

Non-limiting examples of improvements in surrogate markers for Pompe disease include increases in α-glucosidase, decreased glycogen accumulation, decreased hypotonia, improvements in muscle function and mobility, including improved exercise tolerance, decreased macroglossia, reduction in cardiomegaly and hepatosplenomegaly, improvements in respiratory function, improvements in swallowing, sucking or feeding, and amelioration of sleep apnea, The phrase "pharmaceutically acceptable" refers to molecular entities and compositions that are physiologically tolerable and do not typically produce untoward reactions when administered to a human. Preferably, as used herein, the term "pharmaceutically acceptable" means approved by a regulatory agency of the federal or a state government or listed in the U.S. Pharmacopeia or other generally recognized pharmacopeia for use in animals, and more particularly in humans. The term "carrier" refers to a diluent, adjuvant, excipient, or vehicle with which the compound is administered. Such pharmaceutical carriers can be sterile liquids, such as water and oils. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E. W. Martin, 18th Edition, or other editions.

Isofagomine (IFG) refers to the compound (2R,3R,4R)-5-(hydroxymethyl)-piperidine-3,4-diol. Isofagomine is described in U.S. Pat. Nos. 5,863,903 and 5,844,102. Isofagomine tartrate has recently been described in U.S. application Ser. No. 11/752,658, which is hereby incorporated by reference, and has been assigned CAS number 919364-56-0. Isofagomine also may be prepared in the form of other acid addition salts made with a variety of organic and inorganic acids. Such salts include those formed with hydrogen chloride, hydrogen bromide, methanesulfonic acid, sulfuric acid, acetic acid, trifluoroacetic acid, oxalic acid, maleic acid, benzenesulfonic acid, toluenesulfonic acid and various others (e.g., nitrate, phosphate, borates, citrates, benzoates, ascorbates, salicylates and the like). Such salts can be formed as known to those skilled in the art. Isofagomine also may form crystals with alkali metals such as sodium, potassium and lithium, with alkaline earth metals such as calcium and magnesium, with organic bases such as dicyclohexylamine, tributylamine, pyridine and amino acids such as arginine, lysine and the like. Such crystals can be formed as known to those skilled in the art.

Other potential chaperones for Gaucher disease are described in pending U.S. patent application Ser. Nos. 10/988,428, and 10/988,427, both filed Nov. 12, 2004). Such compounds include glucoimidazole ((5R,6R,7S,8S)-5-hydroxymethyl-5,6,7,8-tetrahydroimidazo [1,2a]pyridine-6,7,8-triol).

"1-deoxygalactonojirimycin" (DGJ) refers to (2R,3S,4R,5S)-2-(hydroxymethyl) piperdine-3,4,5-triol, also known as migalastat. This term includes both the free base and any salt forms. The hydrochloride salt of DGJ is known as migalastat hydrochloride. As used herein, the term "free base equivalent" or "FBE" refers to the amount of DGJ present in the DGJ or salt thereof. In other words, the term "FBE" means either an amount of DGJ free base, or the equivalent amount of DGJ free base that is provided by a salt of DGJ. For example, due to the weight of the chloride anion, 150 mg of DGJ HCl only provides as much DGJ as 123 mg of the free base form of DGJ. Other salts will have different conversion factors, depending on the molecular weight of the counter ion.

Other chaperones for α-GAL are described in U.S. Pat. Nos. 6,274,597, 6,774,135, and 6,599,919 to Fan et al., and include α-3,4-di-epi-homonojirimycin, 4-epi-fagomine, α-allo-homonojirimycin, N-methyl-deoxygalactonojirimycin, β-1-C-butyl-deoxygalactonojirimycin, and α-galacto-homonojirimycin, calystegine A3, calystegine B2, N-methyl-calystegine A3, and N-methyl-calystegine B2.

"1-deoxynojirimycin" (DNJ) refers to (2R,3R,4R,5S)-2-(hydroxymethyl) piperidine-3,4,5-triol. This term includes both the free base and any salt forms, particularly the hydrochloride salt.

The term "substantially equal duration" refers to a period of time that is at least within ±1 day of a given period of time. For example, 3 days is a substantially equal duration when compared to 4 days, and vice versa. Thus embodiments below that call for daily dosing for three days and a washout period of four days would be considered an example of daily dosing for a period of time followed by a washout period of substantially equal duration.

Substantially equal duration also encompasses equal duration. Thus 7 days is a substantially equal duration as 7 days. Thus embodiments below that call for daily dosing for seven days and a washout period of seven days would be considered an example of daily dosing for a period of time followed by a washout period of substantially equal duration.

Although the dosing regimens described in this application are described largely in reference to lysosomal storage diseases, it is understood that other conditions that are caused by, or aggravated by misfolded proteins may be treated using the dosing regimens described herein. Also, any disease or condition that may be treated or ameliorated with the pharmacological chaperones described in this application, including but not limited to Alzheimer's Disease and Parkinson's Disease, may be treated using the dosing regimens of the present application.

The terms "about" and "approximately" shall generally mean an acceptable degree of error for the quantity measured given the nature or precision of the measurements. Typical, exemplary degrees of error are within 20 percent (%), preferably within 10%, and more preferably within 5% of a given value or range of values. Alternatively, and particularly in biological systems, the terms "about" and "approximately" may mean values that are within an order of magnitude, preferably within 5-fold and more preferably within 2-fold of a given value. Numerical quantities given herein are approximate unless stated otherwise, meaning that the term "about" or "approximately" can be inferred when not expressly stated.

Gaucher Disease

Gaucher disease (GD) is a lysosomal storage disorder caused by diminished activity of a key metabolic enzyme, β-glucocerebrosidase (GCase). The reduced activity of GCase leads to the accumulation of glycosphingolipids called glucocerebrosides inside the lysosomes in cells, in particular, macrophages of the liver, bone marrow, and spleen. Patients with GD exhibit hematological manifestations such as anemia and thrombocytopenia, as well as hepatosplenomegaly, skeletal impairment, and in some cases neurological impairment. The symptoms, severity, and age of onset depend in part on the mutations underlying the disease; over 200 mutations in the GBA gene have been identified, but four mutations are found in the majority of patients. Two of these mutations, N370S and L444P, are amino acid substitutions that are found in more than 90% of the Gaucher population. The other two mutations (84insG and IVS2) are DNA insertion and deletion mutations, respectively.

From a clinical perspective, GD has been classified into three subtypes: type 1 (non-neuronopathic), type 2 (infantile acute neuronopathic), and type 3 (subacute neuronopathic). Type 1 disease is most often associated with the N370S mutation, but type 3 disease most often presents in patients who carry the L444P mutation. Patients with type 1 Gaucher disease, the most common subtype, display a wide range of symptoms. These symptoms include splenomegaly, hepatomegaly, anemia, thrombocytopenia, bone complications (including osteopenia, lytic lesions, pathological fractures, chronic bone pain, acute bone crises, bone infarcts, osteonecrosis, and skeletal deformities), and in a small number of patients, interstitial lung disease and pulmonary hypertension. Type 2 GD presents in infancy and is characterized by a rapid neurodegenerative course with widespread visceral involvement. Failure to thrive and stridor because of laryngospasm are commonly observed, and death caused by progressive psychomotor degeneration occurs within the first 2 to 3 years of life. Type 3 GD presents around preschool age and is characterized by visceral and bone involvement, in addition to neurological symptoms such as abnormal eye movements, ataxia, seizures, and dementia. The neurological symptoms usually appear later in life, and patients often survive until their third or fourth decade. The most prominent difference between the three types are neurological involvement, which is absent in type 1 and present in types 2 and 3. The rate of disease progression is slow in type 1, rapid in type 2, and intermediate in type 3.5.

Current treatment options for GD include enzyme replacement therapy (ERT) and substrate reduction therapy (SRT). These therapies have been shown to address the major hematological defects and reduce organ volume in most patients. However, neither is approved to treat the neurological symptoms or skeletal symptoms of Gaucher disease.

Nonclinical toxicology studies conducted in rats and monkeys have shown that repeated dosing with the pharmacological chaperone isofagomine tartrate (IFG) is generally safe and well tolerated. IFG is an iminosugar that functions as a selective pharmacological chaperone of GCase that is less stably folded as a result of missense mutations. Current data suggest that IFG may work by stabilizing mutant forms of GCase in the endoplasmic reticulum and promoting proper trafficking of the enzyme to the lysosome (Steet et al., *PNAS.* 2006; 103: 13813-18; Lieberman et al., *Nature Chem Biol.* 2007; 3(2):101-7). In the lysosome, when the pharmacological chaperone dissociates from the enzyme, the enzyme can perform its normal function, which is to catalyze the breakdown of glucosylceramide (GlcCer), the GCase substrate. Studies have shown that treatment with IFG increases GCase total cellular enzyme levels in vitro, increases GCase trafficking to the lysosome in fibroblasts of GD patients, and increases tissue GCase activity and reduces plasma levels of chitinase and immunoglobulin G (IgG) in a mouse model of GD. These results, along with results from early clinical studies in patients, strongly support the use of IFG tartrate in patients with GD resulting from missense mutations in the GBA gene.

Fabry Disease

Fabry disease is a lysosomal storage disorder resulting from a deficiency in the lysosomal enzyme α-galactosidase A (α-GAL). Symptoms can be severe and debilitating, including kidney failure and increased risk of heart attack and stroke. The deficiency of α-GAL in Fabry patients is caused by inherited genetic mutations. Certain of these mutations cause changes in the amino acid sequence of α-GAL that may result in the production of α-GAL with reduced stability that does not fold into its correct three-dimensional shape. Although α-GAL produced in patient cells often retains the potential for some level of biological activity, the cell's quality control mechanisms recognize and retain misfolded α-GAL in the endoplasmic reticulum, or ER, until it is ultimately moved to another part of the cell for degradation and elimination. Consequently, little or no α-GAL moves to the lysosome, where it normally breaks down GL-3. This leads to accumulation of GL-3 in cells, which is believed to be the cause of the symptoms of Fabry disease. In addition, accumulation of the misfolded α-GAL enzyme in the ER may lead to stress on cells and inflammatory-like responses, which may contribute to cellular dysfunction and disease.

The clinical manifestations of Fabry disease span a broad spectrum of severity and roughly correlate with a patient's residual α-GAL levels. The majority of currently treated patients are referred to as classic Fabry disease patients, most of whom are males. These patients experience disease of various organs, including the kidneys, heart and brain, with disease symptoms first appearing in adolescence and typically progressing in severity until death in the fourth or fifth decade of life. A number of recent studies suggest that there are a large number of undiagnosed males and females that have a range of Fabry disease symptoms, such as impaired cardiac or renal function and strokes, that usually first appear in adulthood. Individuals with this type of Fabry disease, referred to as later-onset Fabry disease, tend to have higher residual α-GAL levels than classic Fabry disease patients. Individuals with later-onset Fabry disease typically first experience disease symptoms in adulthood, and often have disease symptoms focused on a single organ, such as enlargement of the left ventricle or progressive kidney failure. In addition, later-onset Fabry disease may also present in the form of strokes of unknown cause.

Similar to IFG for GCase, DGJ has been show to bind in the active site of α-GAL and increase its activity in vitro and in vivo (see Example 5).

Dosing Considerations for Pharmacological Chaperones

According to the present invention, dosing is determined using a simplified model which depends on certain observable factors identified by in vitro and in vivo evaluation. Such factors include the pharmacokinetics of the candidate pharmacological chaperone in plasma and tissue, the rate of enzyme accumulation in the lysosome; the rate of enzyme turnover (half life in the lysosome); and the binding affinity of drug to enzyme as determined in vitro. The rationale for using the foregoing parameters to model dosing regimens was determined using isofagomine tartrate following preclinical studies in animals, and Phase I and Phase II trials in humans, as well as in vitro testing, as described below.

TABLE 1

| PK considerations | PD considerations |
| --- | --- |
| Cmax | Rate of enzyme accumulation |
| Tmax (plasma and tissue) | Rate of enzyme turnover (lysosomal half-life) |
| Dosing interval | Time above the $EC_{50}$ |
| Drug half-life (plasma and tissue) | Time below the $IC_{50}$ |
| | Emax |
| | Dosing interval |

Pharmacokinetics and Pharmacodynamics of IFG Tartrate.

In the Phase 1 trials to evaluate the safety of IFG, a candidate chaperone for GCase, in healthy adult subjects, single doses of up to 300 mg, and repeated doses of up to 225 mg/d for 7 days were administered orally in randomized, double-blind, placebo controlled studies. In the multiple-dose study, three cohorts of 8 subjects (6 active and 2 placebos per cohort) received daily oral doses of 25, 75, or 225 mg IFG or placebo for 7 days, with a treatment-free safety evaluation period of 7 days. Blood samples were collected for pharmacokinetic analysis before the initial drug administration on Day 1, before the 5th, 6th and 7th doses (on Days 5, 6 and 7) (for Cmin determination), and at the following times after the 1st (Day 1) and 7th (Day 7) doses: 0.5, 1, 1.5, 2, 3, 4, 5, 6, 8, 10, 12, 15, 18, and 24 hours. In addition, a single blood sample was collected 48 hours after the last dose (Day 9) and assayed for the presence of IFG. In addition, blood samples were collected for pharmacodynamic measurements, i.e., analysis of WBC GCase levels, before dosing on Day 1, Day 3, Day 5, and Day 7, and at return visits on Day 9, Day 14 and Day 21.

In the multiple-dose study, after 7 days of oral administration, the pharmacokinetic behavior was found to be linear with dose, with no unexpected accumulation of IFG. Mean plasma levels (Tmax) peaked at about 3.4 hr. (SEM: 0.6 hr.) and the plasma elimination half-life was about 14 hr. (SEM: 2 hr.) (FIG. 1).

Importantly, healthy subjects receiving IFG showed a dose-dependent increase in GCase levels in white blood cells during the 7-day treatment period, in most cases peaking on day 7 of treatment, followed by a more gradual decrease in enzyme levels upon removal of the drug and a return to near baseline levels by 14 days after the last dose (FIG. 2). The maximum increase in enzyme level achieved was approximately 3.5-fold above baseline levels. The lowest daily dose that achieved the maximum rate of GCase accumulation over 7 days was about 75 mg.

Based on results from the foregoing multiple-dose study and in vitro cell-based assays (healthy human skin fibroblasts), the following observations were made relating to the PK and PD properties of IFG.

TABLE 2

Plasma PK and PD

| | |
|---|---|
| Cmax (µM) | 1.7 (150 mg IFG) |
| | 0.31 (25 mg IFG) |
| Tmax (hrs) | 3 |
| Half-life (hrs) | 14 |
| $EC_{50}$ (µM) (cellular) | 0.3 |
| $IC_{50}$ (µM) (purified enzyme; pH 5.2) | 0.03 |

Long-Term Maintenance of Elevated Enzyme Levels.

Since pharmacological chaperones, such as IFG, are potent inhibitors of the intended target enzymes, it was hypothesized that a dosing regimen involving "peaks" and "troughs" would be necessary to prevent sustained inhibition of the target enzyme. Accordingly, the need for non-daily dosing as opposed to daily dosing appeared likely, in which the goal would be to achieve plasma concentrations of the drug that are initially above the cellular $EC_{50}$ (as determined in vitro cellular enzyme activity assays) for some period of time, so as to maximize the amount of enzyme that is trafficked to lysosomes, followed by some period of time where the concentration of drug falls below the $IC_{50}$ (as determined in vitro using cell lysate at the lysosomal pH of 5.2). Accordingly, a simple model was devised wherein certain PK and PD parameters could be used to estimate dosing regimens that would both (i) achieve a plasma concentration above the $EC_{50}$ and (ii) permit the plasma concentration to fall below the $IC_{50}$.

In brief, the above parameters were used to estimate the plasma concentration over time using different dosing regimens based on the exponential terminal elimination half-life of IFG. This was followed by a determination of if and for how long the resulting plasma concentrations would be above the $EC_{50}$ or below the $IC_{50}$.

$IC_{50}$ and $EC_{50}$ Considerations

Based on the foregoing, it was determined that a dosing regimen in which 150 mg of IFG was administered once a day would result in plasma concentrations that reach or exceed the observed $EC_{50}$ for GCase, thereby promoting chaperoning (trafficking from the ER to the lysosome) for a significant period of time. However, at this daily dose, the plasma concentration is not expected to fall below the $IC_{50}$ for GCase (FIG. 3A), which is required for maximal turnover of the accumulated substrate. Accordingly, this dosing regimen may not provide the optimal response in vivo because they it may not permit substrate clearance.

Consideration of Dose (Cmax)

Figure 3B:
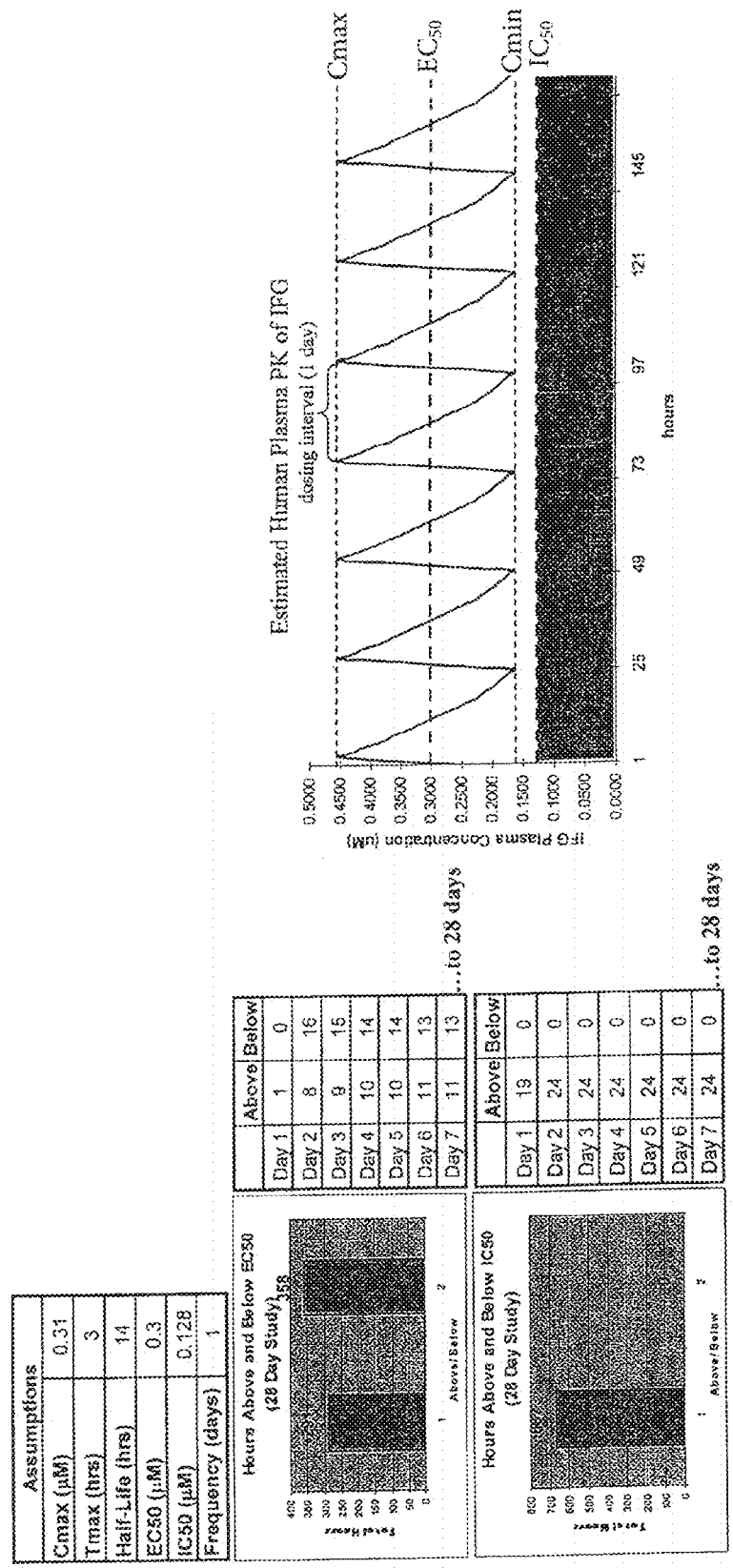

Lowering the dose to 25 mg of IFG once daily (for 28 days) is expected to reduce the time above the $EC_{50}$, but concentrations below the $IC_{50}$ are still not obtained (FIG. 3B). Thus, it was proposed that longer intervals at a higher dose should be used to maximize the time above $EC_{50}$ while allowing the concentration to drop below the $IC_{50}$ for a period of time.

Dosing Interval Considerations

Figure 3C:
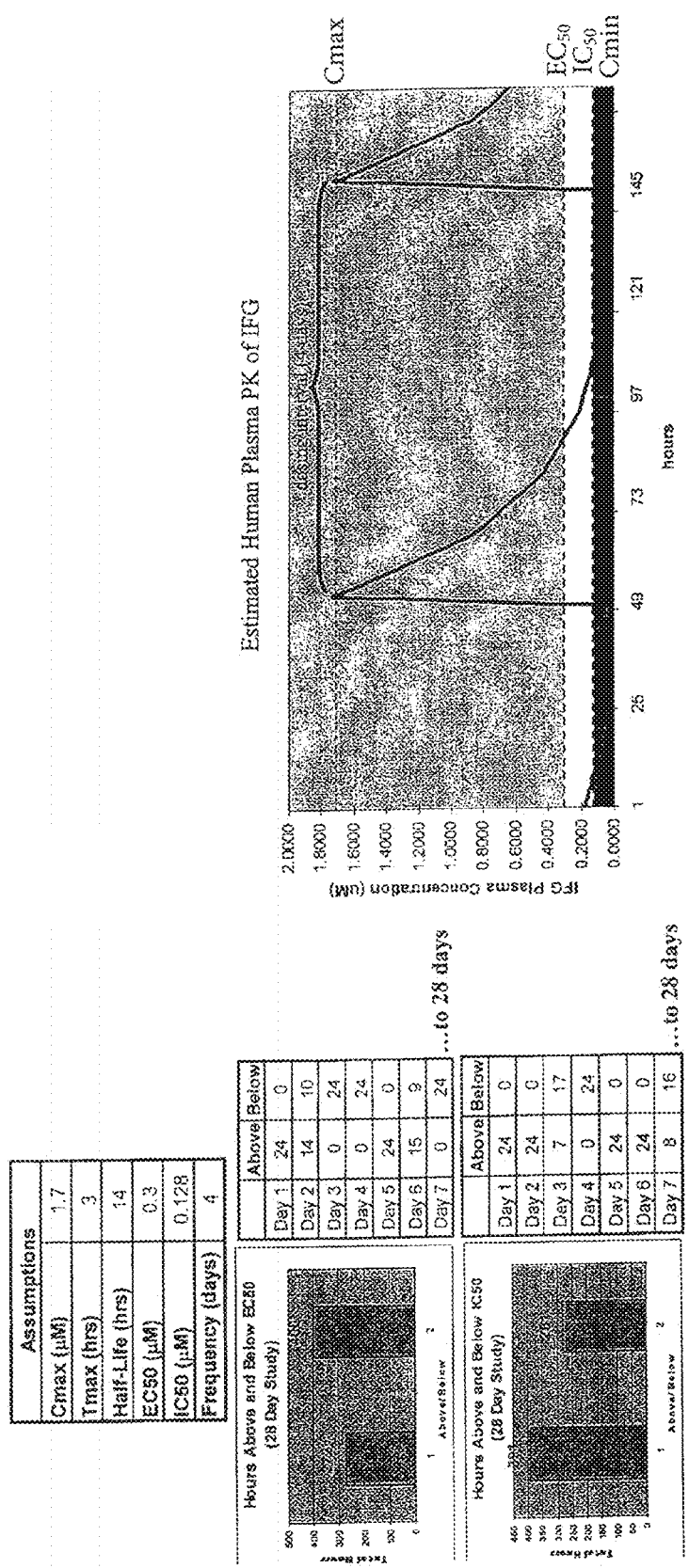

In view of the foregoing, administration of 150 mg IFG every 4 days (for 28 days) is predicted to provide plasma concentrations above and below the $EC_{50}$ and $IC_{50}$, respectively, for nearly equal periods of time (FIG. 3C). It has been determined experimentally that maximum chaperoning (Emax) in Gaucher patient-derived fibroblasts, lymphoblast and macrophages occurs in a range from about 10-100 µM IFG (FIG. 4). Thus, it is anticipated that the rate of GCase accumulation during the "above $EC_{50}$" time period will increase as Cmax approaches Emax.

Initial Enzyme Build-Up Phase

Accordingly, using the simplified model, it was discovered that administering a daily dose of IFG for an initial period of time would achieve the goal of maximizing the amount of GCase trafficking to lysosomes, i.e., the dose would result in plasma concentrations of chaperone above the $EC_{50}$. During this period, this dose would permit specific binding to the enzyme, increase its stability, and induce trafficking and localization of the enzyme to the lysosomes. This initial dose is referred to as the "Initial Enzyme Build-Up Phase."

Assuming IFG has no effect on GCase's rate of synthesis, GCase's rate of accumulation or "build up" is determined by the difference between the amount of enzyme trafficked from the ER to the lysosome and the amount of enzyme lost due to its rate of turnover in the lysosome. Thus, GCase levels in the lysosome will increase when the amount of GCase trafficked to the lysosome exceeds the amount of enzyme lost due to turnover, while lysosomal levels of GCase will decrease if the amount of enzyme trafficked to the lysosome is not sufficient to replace the amount of enzyme lost due to turnover. Since the amount of GCase trafficked to the lysosome is dependent upon the concentration of IFG (in the ER), the net change in lysosomal GCase levels is therefore a function of IFG concentration. If sufficient concentrations are reached in plasma and tissues to cause accumulation of GCase, the rate of accumulation will be at its maximum during the peaks (sometime after Cmax due to the lag time associated with penetration into the tissues, cells and ER), and at its minimum during the troughs (some time after the Cmin). Thus the time between doses, Cmax and Cmin determine the net change in GCase levels for any given dosing interval.

Our model predicts that dosing regimens that maximize trafficking during the peaks and substrate turnover during troughs, will result in a slower accumulation rate of GCase than dosing regimens that favor trafficking during both peaks and troughs. Therefore, for a given dose, the rate of accumulation of GCase will increase as the interval between doses is shortened and if the length of the dosing interval is held constant, the rate of accumulation will also increase as the dose is increased (if Cmax<Emax). Taking this into consideration, our model predicts that we could build-up enzyme levels in a relatively short period of time (1-2 weeks) by administering a dosing regimen that favors trafficking throughout the dosing interval, and maintain the elevated GCase levels by switching to a regimen that provides peaks and troughs that alternately maximize trafficking and substrate turnover.

Alternatively, initial "build-up" phases (several days long) could be repeated and separated by "drug free" phases (also several days long).

It should be noted that the foregoing was calculated based on the interaction of IFG with the wild-type GCase enzyme. However, patients with Gaucher disease will not have a wild-type enzyme, and thus the rate of enzyme turnover, residual level of enzyme activity, relative affinity of IFG for the enzyme, and dose that yields the maximum rate of accumulation will be different from that of the wild-type for each mutation. For example, the most prevalent mutation in Gaucher disease is N370S. This mutant has a lower affinity for IFG compared to the wild-type, although the half-life is similar to that of the wild-type (Steet et al., *PNAS* 2006). Accordingly, the rate of N370S turnover and the dose that will yield the maximum rate of GCase accumulation, can be estimated based on the differences in PK and PD parameters as compared with the wild-type enzyme:

TABLE 3

| Parameter | Wild-type | N370S (expected) |
|---|---|---|
| Max. rate of enzyme accumulation | ~7 Units/day | ~0.35 Units/day |
| Max. rate of enzyme loss | ~-3.5 Units/day | ~-0.17 Units/day |
| Residual level of enzyme activity | ~20 Units | ~1 Unit |
| Relative affinity for IFG | 1 | .33 |
| Daily dose that yields max rate of accumulation during Initial Enzyme Build-Up phase | ≤75 mg | ≤150-300 mg |

(1 unit = 1 nmole of 4-MU liberated per mg of total protein per hour)

Figure 5B:
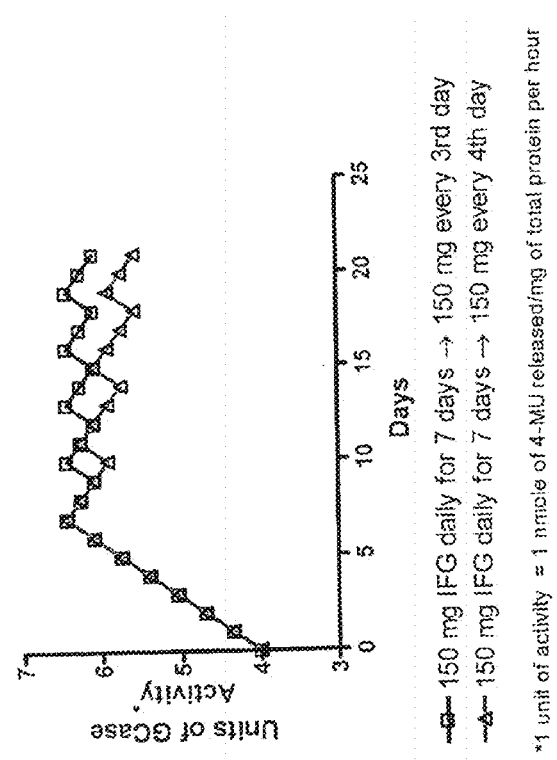
FIG. 5B shows the estimated plasma PK results following administration of 150 mg of IFG daily for 7 days, and then 150 mg every 3 or 4 days.

From the foregoing, several dosing regimens for IFG to be administered to Gaucher patients with the N370S mutation were modeled in silico (using the parameters discussed above). Specifically, the regimens were as follows:
1. Two Different Maintenance Dosing Regimens Without an Initial Enzyme Build-Up Phase
   a. Administration of 150 mg of IFG every 3 days (FIG. 5A)
   b. Administration of 150 mg of IFG every 4 days (FIG. 5A)
2. Initial Enzyme Build-Up Phase Followed by Two Different Maintenance Dosing Regimens
   a. Administration of 150 mg IFG daily for 7 days, followed by administration of 150 mg of IFG every 4 days (FIG. 5B)
   b. Administration of 150 mg of IFG daily for 7 days, followed by administration of 150 mg of IFG every 7 days (FIG. 5B)
3. Repeated Enzyme Build-Up Phases Separated by "Drug Free" Phases
   a. Administration of 150 mg of IFG daily for 4 days, followed by 3 days without administration of IFG (FIG. 5C).
   b. Administration of 150 mg of IFG daily for 3 days, followed by 4 days without administration of IFG (FIG. 5C).

The results are presented in FIG. 5. The Dosing every 2 days without an Initial Enzyme Build-Up phase, is projected to result in an increase to a sustainable maximal GCase activity, but over a longer time. This may be beneficial for people who have adverse side effects with daily administration of pharmacological chaperones and cannot tolerate an Initial Enzyme Build-Up phase.

The second regimen is expected to increase the rate of accumulation of GCase in the lysosomes during the Initial Enzyme Build-Up Phase, which is either maintained or gradually decreases over about 50 days during the Maintenance Phase. In this instance, subsequent Enzyme Build-Up Phases may need to be contemplated about every 35-40 days to permit re-accumulation of GCase in the lysosome, i.e., maximal chaperoning.

The third regimen is expected to increase the rate of GCase accumulation in the lysosome during repeated Enzyme Build-Up Phases (3-4 days), while still permitting dissociation of the chaperone and periods of maximal enzyme activity for substrate reduction during the intervening "drug free" phase (3-4 days).

As one of skill in the art will appreciate, optimizing dose and dosing interval for the treatment of patients with different mutations will be determined by specific properties of the mutant enzyme:
1. Half-life of the mutant enzyme: because some mutations result in enzymes which may have shorter half-lives than N370S GCase, shorter dosing intervals may be required for these mutants
2. Tissue half-life of chaperone: for chaperones with longer tissue half-lives than plasma half-lives, a longer interval between doses may be required
3. $EC_{50}/IC_{50}$: different mutant enzymes may have reduced affinity for IFG, so the dose may need to be increased (adjust $EC_{50}$ and $IC_{50}$ as needed).
4. Type of mutant: Many patients may have two different mutant alleles (compound heterozygotes)—if both mutations are thought to respond to IFG than a dosing regimen should be selected that will be optimal for both mutations. Dose optimization should be based on the highest $EC_{50}$ while the shortest half-life should be taken into consideration when selecting a dosing interval or duration of a Drug Free Phase. Additionally, priority for optimization should be given to the mutant that is expected to provide the greatest contribution to the total increase in GCase activity.

Rationale Applied to Model Dosing Regimens for Fabry Disease

The model described above is readily applicable to estimating dosing regimens for other specific pharmacological chaperones for other enzymes. As indicated earlier, the use of 1-deoxygalactonojrirmycin hydrochloride (DGJ) as a chaperone for α-galactosidse A (α-Gal A) for the treatment of Fabry disease is being evaluated in clinical studies.

A multiple-dose Phase I trial was conducted and consisted of a total of 16 healthy volunteers divided into two groups of eight subjects. Six subjects in each group received DGJ and two subjects received placebo. All subjects in one group received placebo or 50 mg twice a day for seven days, and all subjects in the other group received placebo or 150 mg twice a day for seven days. Subjects were evaluated at the beginning of the study, on Day 7 after seven days of treatment and on Day 14 after a seven day washout period.

The data from the multiple-dose Phase I trial showed a dose-related increase in the level of α-GAL in the white blood cells of healthy volunteers administered DGJ for seven days. At the highest dose level there was approximately a 2-fold increase in levels of α-GAL, and this increase was maintained for at least seven days after the last dose.

Results of in vitro and in vivo animal and Phase I studies using DGJ and wild-type α-GAL yielded the following PK and PD information (following oral administration of 150 mg DGJ hydrochloride):

TABLE 4

Plasma PK and PD

| | |
|---|---|
| Cmax (μM) | 9 |
| Tmax (hrs) | 3 |
| Half-life (hrs; exponential decay) | 3 |
| Ki (μM) | .04 |
| $EC_{50}$ (μM) (cellular) | 0.4 |
| $IC_{50}$ (μM) (purified enzyme) | 0.4 |

Figure 6:
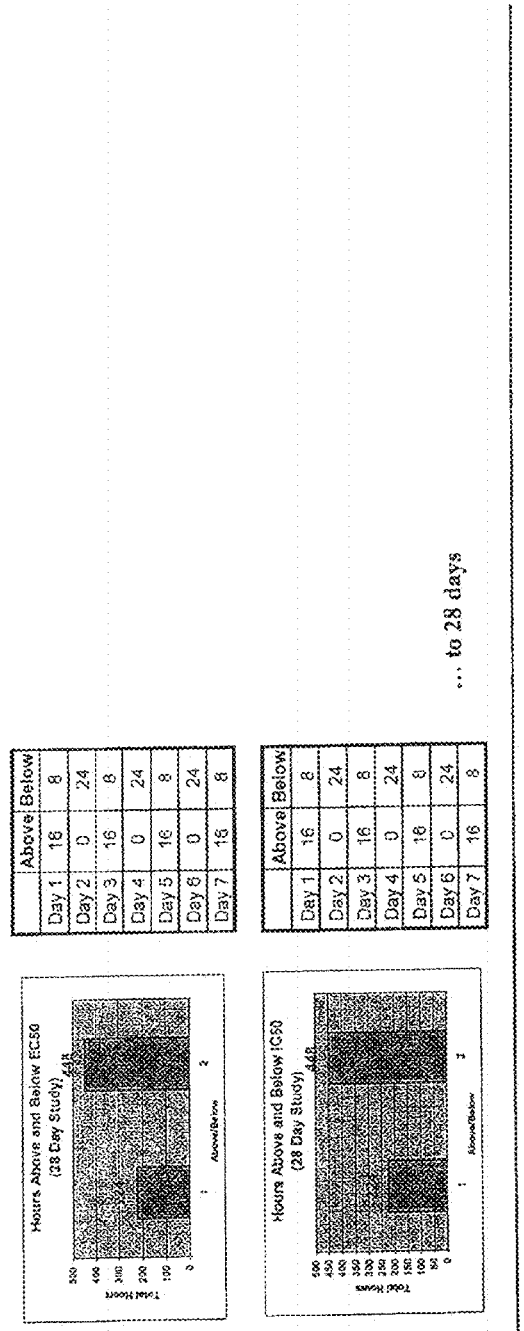
FIG. 6 shows the results of in silico modeling of drug plasma concentrations above and below the $EC_{50}$ and $IC_{50}$, respectively, following administration of 150 mg of DGJ every other day.

Since DGJ has a much shorter plasma half-life than IFG, the optimal Maintenance Dose is likely to be shorter than for IFG following the Initial Enzyme Build-Up Phase. As one example, it is predicted that administration of 150 mg DGJ every other day for 28 days will result in a plasma concentration above the $EC_{50}$ for about 16 hours on the day the dose is administered, and below the $IC_{50}$ for the remaining 8 hours (FIG. 6). On the second day when no drug is administered, the plasma concentration is expected to be below the $IC_{50}$ until the following day when the drug is administered again (FIG. 6). This pattern continues for the duration of the treatment period.

Specific Dosing Regimens for Gaucher Disease, Fabry Disease and Pompe Disease

The following dosing regimens are specifically provided for Gaucher, Fabry and Pompe disease, but they can also be used for the treatment of any lysosomal storage disorder that are amenable to treatment with the pharmacological chaperones described below.

Gaucher Disease.

In one embodiment of the invention, the Initial Enzyme Build-Up (loading) Phase, or the first phase of the dosing regimen, in which the pharmacological chaperone (e.g. IFG tartrate) is orally administered daily will be from about 4 to about 10 days, or from about 5 to about 8 days, or for about 7 days.

In this embodiment, the daily dose will be in a range from about 75 mg to about 300 mg per day, or from about 125 mg to about 225 mg, or about 150 mg of pharmacological chaperone (e.g. IFG tartrate). Alternatively, a daily dose of 225 mg of pharmacological chaperone could be administered.

Following completion of the first phase, the Maintenance Phase will begin.

In one alternative embodiment, a first washout period will take place following the first phase and prior to the maintenance phase.

In one embodiment, during the first washout period administration of the pharmacological chaperone from the first phase is stopped for a period of between about 1 and 10 days, or from about 2 to 8 days, or about 7 days.

In another embodiment, the first phase and the washout period can last for a period of about 1 week to about 30 weeks, or from about 2 weeks to about 25 weeks, or about 2 weeks, or about 24 weeks.

In one embodiment, the interval for dosing during the Maintenance Phase will be from about every 2 days to about every 8 days. In another embodiment, the interval will be from about every 4 days to about every 7 days. In a third embodiment, the interval will be about every 7 days.

In these embodiments, the dose administered during the Maintenance Phase (the "Maintenance Dose") will be in a range from about 75 mg to about 300 mg, or, in one aspect, about 150 mg per dose of pharmacological chaperone (e.g. IFG tartrate), or in another aspect 225 mg per dose. These dosages are administered once per interval described above Alternatively, the maintenance phase may consist of daily administration for a period of time. In one embodiment the maintenance phase period can be between 1 and 8 days, or about 4 and 7 days, or about three days, or about 7 day, followed by a second "washout period" of substantially equal duration. For example the maintenance phase may consist of 3 daily dosages of pharmacological chaperone (e.g. IFG tartrate) from about 75 mg to about 300 mg, or from about 125 mg to about 275 mg, or 225 mg followed by between about 1 and 10 days, or about 2 and 8 days, or about four days of washout, i.e. without any pharmacological chaperone administered.

In a further embodiment, the maintenance phase and the washout period can last for a period of between about 1 week and about 30 weeks, or between about 2 weeks and about 25 weeks, or about 22 weeks.

In another alternative embodiment, there can be no maintenance phase and second washout period.

In another embodiment, the patient does not ingest any food (i.e. "fasts") prior to and following the administration of a pharmacological chaperone for a period of between about 0.5 and about 24 hours, or between about 1 and about 12 hours, or about 2 hours.

In one specific example, 150 mg of IFG tartrate is administered daily for seven days (Enzyme Build-up Phase). After these seven days 225 mg of IFG tartrate is administered daily for 3 days (3 days on) followed by a washout period of 4 days (4 days off). The 3 days on/4 days off regimen is repeated indefinitely In another specific example, 150 mg of IFG tartrate is administered daily for seven days. After these seven days 225 mg is administered daily for 7 days (7 days on) followed by a washout period of 7 days (7 days off). The 7 days on/7 days off regimen is repeated indefinitely.

In another specific example, 225 mg of IFG tartrate is administered daily for seven days. (7 days on) followed by a washout period of 7 days (7 days off). The 7 days on/7 days off regimen is repeated for a period of 24 weeks.

In another specific example, 225 mg of IFG tartrate is administered daily for seven days. (7 days on) followed by a washout period of 7 days (7 days off). Next, 225 mg of IFG tartrate is administered daily for 3 days (3 days on) during a maintenance phase, followed by a second washout period of 4 days (4 days off). The 3 days on/4 days off regimen is repeated for a period of 22 weeks.

In another aspect of the invention, sustained low plasma concentrations may be desirable following the dose administered during the Initial Enzyme Build-Up Phase. In this embodiment, an Initial Enzyme Build-Up Phase is envisioned at a dose capable of resulting in maximum increases in enzyme level, followed by a much lower daily dose for a Maintenance Dose that is capable of sustaining an increased level of enzyme exiting the ER while also permitting dissociation of the chaperone once the enzyme is in the lysosome.

In this embodiment, the Initial Enzyme Build-Up Phase, or the first phase of the dosing regimen, in which the pharmacological chaperone (e.g. IFG tartrate) is orally administered daily will be from about 4 to about 14 days, or from about 5 to about 10 days, or for about 7 days, and the loading dose will be in a range from about 75 mg to about 300 mg per day, or from about 125 mg to about 225 mg, or about 150 mg.

Following completion of the first phase, the Maintenance Phase will begin in which the daily dose is reduced to about 25 to 50 mg, or about 25 mg of pharmacological chaperone (e.g. IFG tartrate).

In a third aspect of the invention, interval dosing about every 2-3 days is contemplated. In this embodiment, between about 75 mg to about 300 mg of pharmacological chaperone (e.g. IFG tartrate) is administered at each interval, or from about 125 mg to about 225 mg at each interval, or about 150 mg at each interval.

For all of the foregoing embodiments, if the interval during the Maintenance Phase is 3 days instead of two days, it may be more efficacious to administer higher doses.

Alternatively, the dosing regimen may consist of administration of a constant amount of pharmacological chaperone over a specific time period. For example a constant amount of pharmacological chaperone may be administered twice daily, once daily, once every 3 days, once every 4 days, once every week, once every two weeks, or once a month. This cycle may be repeated indefinitely.

In one embodiment, from about 10 mg to about 200 mg of pharmacological chaperone (e.g. IFG tartrate) is administered daily. For example, 10 mg, or 25 mg, or 50 mg, or 75 mg, or 100 mg or 125 mg or 150 mg, or 175 mg, or 200 mg of pharmacological chaperone (e.g. IFG tartrate) is administered daily.

In one specific embodiment, 25 mg/day of IFG tartrate is administered. In another embodiment, 150 mg/day of IFG tartrate is administered.

In an alternative embodiment, from about 10 mg to about 400 mg of pharmacological chaperone (e.g. IFG tartrate) is administered once every three days, once every four days, or alternatively once every week. For example, 10 mg, or 25 mg, or 50 mg, or 75 mg, or 100 mg or 125 mg or 150 mg, or 175 mg, 200 mg, 250 mg, 300 mg, 350 mg, or 400 mg of pharmacological chaperone (e.g. IFG tartrate) is administered once every three days, once every four days, or once every week.

In one specific embodiment, 150 mg of IFG tartrate is orally administered every four days. In another embodiment, 150 mg/day of IFG tartrate is orally administered once every week.

Fabry Disease.

In one embodiment of the invention, the Initial Enzyme Build-Up (loading) Phase, or the first phase of the dosing regimen, in which a pharmacological chaperone (e.g. DGJ hydrochloride) is orally administered daily will be from about 4 to about 10 days, or from about 5 to about 8 days, or for about 7 days.

In this embodiment, the daily dose of pharmacological chaperone (e.g. DGJ hydrochloride) during the first phase will be in a range from about 200 mg to about 500 mg per day, or from about 250 mg to about 300 mg per day, or about 250 mg per day. These levels may be achieved gradually in an ascending manner. For example, the dose of pharmacological chaperone (e.g. DGJ hydrochloride) may begin at 25 mg for a period of time (e.g. 2 weeks), then progressed to 100 mg for a period of time (e.g. two weeks), and then progressed to the highest dose administered for the remainder of the Build-Up Phase.

Alternatively, the maximum amount administered during the build-up phase may be administered initially, i.e. no ascending dosages.

Following completion of the first phase, the Maintenance Phase will begin. In one embodiment, the interval for dosing during the Maintenance Phase will be from about every 2 days to about every 3 days. In another embodiment, the interval will be from about every 2 days.

In these embodiments, the Maintenance Dose will be in a range from about 75 mg to about 225 mg per dose, or from about 100 mg to about 200 mg per dose, or, in a specific embodiment, about 150 mg per dose.

In another embodiment, sustained low steady-state plasma concentrations may be desirable following the Initial Enzyme Build-Up Phase. In this embodiment, a Initial Enzyme Build-Up Phase is envisioned at a dose capable of resulting in maximum increases in enzyme level, followed by a much lower daily dose that is capable of sustaining an increased level of enzyme exiting the ER while also permitting dissociation of the chaperone once the enzyme is in the lysosome.

In this embodiment, Initial Enzyme Build-Up Phase, or the first phase of the dosing regimen, in which the pharmacological chaperone (e.g. DGJ hydrochloride) is orally administered daily will be from about 4 to about 14 days, or from about 5 to about 10 days, or in a particular embodiment, for about 7 days, and the loading dose of pharmacological chaperone (e.g. DGJ hydrochloride) may be in a range from about 200 mg to about 500 mg per day, or from about 250 mg to about 300 mg per day, or about 250 mg per day.

Alternatively, the first phase may last for a period from about two weeks to about 12 weeks, for from about 4 weeks to about 8 weeks (e.g. 6 weeks). The loading dose of pharmacological chaperone (e.g. DGJ hydrochloride) may be in a range from about 200 mg to about 500 mg per day, or from about 250 mg to about 300 mg per day, or about 250 mg per day.

As noted above, the these dosage amounts during the Build-Up Phase may be achieved in an ascending manner, or the maximum amount administered during the build-up phase may be administered initially.

Following completion of the first phase, a reduction in the daily dose will begin. In this embodiment, the daily dose is reduced to about 25 to 50 mg, or about 25 mg. This is the Maintenance Dose.

In one specific embodiment, the Build-Up Phase consists of 2 weeks at 25 mg/day, 2 weeks at 100 mg/day and 2 weeks at 250 mg/day of orally administered DGJ hydrochloride, followed by a period of time (e.g. 24 weeks) at 25 mg/day, followed by a period of time (e.g. 66 weeks) of 50 mg/day or orally administered DGJ hydrochloride.

In a third aspect of the invention, interval dosing about every 2-3 days is contemplated. In this embodiment, between about 25 mg to about 300 mg of pharmacological chaperone (e.g. DGJ hydrochloride) is administered at each interval, or from about 125 mg to about 225 mg at each interval, or about 150 mg at each interval. In specific embodiments, DGJ hydrochloride will be administered at 50 mg, 150 mg or 250 mg every 2 days.

For all of the foregoing embodiments, if the interval is 3 days instead of two days, it may be more efficacious to administer higher interval doses.

Similar as for IFG described above, if a patient cannot tolerate the dose administered during the Initial Enzyme Build-Up Phase, and interval dosing without this phase will not achieve plasma concentrations at or above the $EC_{50}$, a more gradual "loading" period, followed by a low daily Maintenance Dose may be appropriate. For example, in one embodiment, DGJ will be administered 50 mg per day for two weeks, followed by 200 mg per day for two weeks, followed by 500 mg per day for two weeks and followed by 50 mg per day for the duration of treatment.

In various embodiments, during the Enzyme Build-Up Phase, the dosage may escalate upwards in dosage amount. For example, ascending dosages of 25, 100, and 250 mg may be administered for one day each, i.e. 25 mg on day 1, 100 mg on day 2, and 250 mg on day 3. Such embodiments may used to slowly acclimate the subject to higher dosage amounts during the Enzyme Build-Up Phase. Alternatively, the dosage amount during the Enzyme Build-Up Phase may be constant throughout the duration of the phase.

In one embodiment, from about 75 mg to about 800 mg per day of pharmacological chaperone, or from about 125 mg to about 600 mg, or 250 mg or 500 mg is administered once a day for a period of one to seven days, followed by a washout period of equal or substantially equal duration. For example, the dosing regimen may consist of three consecutive days of receiving a daily dosage of pharmacological chaperone (e.g. DGJ or DGJ hydrochloride), followed by four consecutive days of not receiving the dosage; or four consecutive days of receiving a daily dosage, followed by three consecutive days of not receiving the dosage.

In one specific example, a dosing regimen for Fabry Disease may call for oral administration of 250 mg, or 500 mg of DGJ hydrochloride once a day for three consecutive days, followed by four days without taking a pharmacological chaperone (i.e. DGJ hydrochloride). Alternatively, the dosing regimen may consist of 250 or 500 mg of pharmacological chaperone (e.g. DGJ or DGJ hydrochloride) once a day for seven consecutive days, followed by seven days without taking the pharmacological chaperone.

Alternatively, from about 75 mg to about 300 mg per day, or from about 125 mg to about 225 mg, or 150 mg may be administered for one to seven days followed by a washout period of unequal duration. For example, the dosing regimen may call for one day of receiving a dosage, followed by six consecutive days of not receiving the dosage; two consecutive days of receiving a daily dosage, followed by five consecutive days of not receiving the dosage; five consecutive days of receiving a daily dosage, followed by two consecutive days of not receiving the dosage; or six consecutive days receiving a daily dosage, followed by one day of not receiving the dosage.

Pompe Disease.

In one embodiment, from about 1000 mg to about 8000 mg per day of pharmacological chaperone (e.g. DNJ), or from about 2000 mg to about 6000 mg, or 2500 mg or 5000 mg of pharmacological chaperone is orally administered once a day for a period of one to seven days, followed by a washout period of equal or substantially equal duration. For example, the dosing regimen may consist of 3 or 4 days "on" (daily administration of the pharmacological chaperone), followed by 4 or 3 days "off" (not administering the pharmacological chaperone). Alternatively, the dosing regimen may consist of seven days on and seven days off.

In one specific embodiment, 2500 mg of DNJ (including pharmaceutically acceptable salts thereof) is orally administered daily for three consecutive days, followed by four consecutive days of not administering a pharmacological chaperone. In an alternative embodiment, 5000 mg of DNJ (including pharmaceutically acceptable salts thereof) is orally administered daily for three consecutive days, followed by four consecutive days of not administering a pharmacological chaperone. In an alternative embodiment, 5000 mg of DNJ (including pharmaceutically acceptable salts thereof) is orally administered daily for seven consecutive days, followed by seven consecutive days of not administering a pharmacological chaperone.

The above dosage amounts may be achieved in an ascending fashion. For example, the dosage amount in the first cycle (i.e. the first three days or first seven days) may be 500 mg, 1000 mg during the second cycle, 2500 mg during the third cycle and 5000 during the fourth cycle.

A person of ordinary skill in the art will be able to apply this strategy to estimate appropriate dosing regimens for other pharmacological chaperones which are competitive inhibitors of lysosomal enzymes to treat other lysosomal storage diseases, based on the specific PK and PD for each enzyme and candidate chaperone.

Formulation and Administration

Isofagomine can be administered in a form suitable for any route of administration, including e.g., orally in the form tablets, capsules, or liquid, or in sterile aqueous solution for injection. It can be administered orally in the form of tablets, capsules, ovules, elixirs, solutions or suspensions, gels, syrups, mouth washes, or a dry powder for constitution with water or other suitable vehicle before use, optionally with flavoring and coloring agents for immediate-, delayed-, modified-, sustained-, pulsed- or controlled-release applications. Solid compositions such as tablets, capsules, lozenges, pastilles, pills, boluses, powder, pastes, granules, bullets, or premix preparations may also be used. Solid and liquid compositions for oral use may be prepared according to methods well known in the art. Such compositions may also contain one or more pharmaceutically acceptable carriers and excipients which may be in solid or liquid form. When the compound is formulated for oral administration, the tablets or capsules can be prepared by conventional means with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art.

The pharmaceutically acceptable excipients also include microcrystalline cellulose, lactose, sodium citrate, calcium carbonate, dibasic calcium phosphate and glycine, disintegrants such as starch (preferably corn, potato or tapioca starch), sodium starch glycolate, croscarmellose sodium and certain complex silicates, and granulation binders such as polyvinylpyrolidone, hydroxypropyl ethylcellulose (HPMC), hydroxypropyl cellulose (HPC), sucrose, gelatin, and acacia. Additionally, lubricating agents such as magnesium stearate, stearic acid, glyceryl behenate and talc may be included.

Solid compositions of a similar type may also be employed as fillers in gelatin capsules. Preferred excipients in this regard include lactose, starch, a cellulose, milk sugar, or high molecular weight polyethylene glycols. For aqueous suspensions and/or elixirs, the agent may be combined with various emulsifying and/or suspending agents and with diluents such as water, ethanol, propylene glycol and glycerin, and combinations thereof.

Liquid preparations for oral administration may take the form of, for example, solutions, syrups or suspensions, or they may be presented as a dry product for constitution with water or another suitable vehicle (for example, ethanol or a polyol such as glycerol, propylene glycol, and polyethylene glycol, and the like, suitable mixtures thereof, and vegetable oils) before use. Such liquid preparations may be prepared by conventional means with pharmaceutically acceptable additives such as suspending agents (e.g., water, sorbitol syrup, cellulose derivatives or hydrogenated edible fats); emulsifying agents (e.g., lecithin or acacia); non aqueous vehicles (e.g., almond oil, oily esters, ethyl alcohol or fractionated vegetable oils); and preservatives (e.g., methyl or propyl-p-hydroxybenzoates or sorbic acid). Preparations for oral administration may be suitably formulated to give controlled or sustained release of the ceramide-specific glucosyltransferase inhibitor.

The proper fluidity can be maintained, for example, by the use of a coating such as lecithin, by the maintenance of the required particle size in the case of dispersion and by the use of surfactants. Prevention of the action of microorganisms can be brought about by various antibacterial and antifungal agents, for example, parabens, chlorobutanol, phenol, benzyl alcohol, sorbic acid, and the like. In many cases, it will be reasonable to include isotonic agents, for example, sugars or sodium chloride. Prolonged absorption of the injectable compositions can be brought about by the use in the compositions of agents delaying absorption, for example, aluminum monosterate, and gelatin.

The pharmaceutical formulations of isofagomine suitable for parenteral/injectable (for example, by intravenous bolus injection or infusion or via intramuscular, subcutaneous or intrathecal routes) use generally include sterile aqueous solutions, or dispersions and sterile powders for the extemporaneous preparation of sterile injectable solutions or dispersion. The isofagomine tartrate may be presented in unit dose form, in ampoules, or other unit-dose containers, or in multi-dose containers, if necessary with an added preservative. The compositions for injection may be in the form of suspensions, solutions, or emulsions, in oily or aqueous vehicles, and may contain formulatory agents such as suspending, stabilizing, solubilizing, and/or dispersing agents. Alternatively, the active ingredient may be in sterile powder form for reconstitution with a suitable vehicle, e.g., sterile, pyrogen-free water, before use. In all cases, the form must be sterile and must be fluid to the extent that easy syringability exists. It must be stable under the conditions of manufacture and storage and must be preserved against the contaminating action of microorganisms such as bacteria and fungi. The preparation of suitable parenteral formulations under sterile conditions is readily accomplished by standard pharmaceutical techniques well known to those skilled in the art.

Sterile injectable solutions are prepared by incorporating isofagomine in the required amount in the appropriate solvent with various of the other ingredients enumerated above, as required, followed by filter or terminal sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

Preservatives, stabilizers, dyes, and even flavoring agents may be provided in the pharmaceutical composition. Examples of preservatives include sodium benzoate, ascorbic acid, and esters of p-hydroxybenzoic acid. Antioxidants and suspending agents may be also used.

Additional pharmaceutically acceptable carriers which may be included in the formulation are buffers such as citrate buffer, phosphate buffer, acetate buffer, and bicarbonate buffer, amino acids, urea, alcohols, ascorbic acid, phospholipids, proteins, such as serum albumin, collagen, and gelatin; salts such as EDTA or EGTA, and sodium chloride; liposomes polyvinylpyrolidone; sugars such as dextran, mannitol, sorbitol, and glycerol; propylene glycol and polyethylene glycol (e.g., PEG-4000, PEG-6000); glycerol, glycine or other amino acids and lipids. Buffer systems for use with the formulations include citrate, acetate, bicarbonate, and phosphate buffers. Phosphate buffer is a preferred embodiment.

The formulations can also contain a non-ionic detergent. Preferred non-ionic detergents include Polysorbate 20, Polysorbate 80, Triton X-100, Triton X-114, Nonidet P-40, Octyl α-glucoside, Octyl β-glucoside, Brij 35, Pluronic, and Tween 20.

The routes for administration (delivery) include, but are not limited to, one or more of: oral (e.g., as a tablet, capsule, or as an ingestible solution), topical, mucosal (e.g., as a nasal spray or aerosol for inhalation), nasal, parenteral (e.g., by an injectable form), gastrointestinal, intraspinal, intraperitoneal, intramuscular, intravenous, intrauterine, intraocular, intradermal, intracranial, intratracheal, intravaginal, intracerebroventricular, intracerebral, subcutaneous, ophthalmic (including intravitreal or intracameral), transdermal, rectal, buccal, epidural and sublingual.

Administration of the above-described parenteral formulations of isofagomine may be by periodic injections of a bolus of the preparation, or may be administered by intravenous or intraperitoneal administration from a reservoir which is external (e.g., an i.v. bag) or internal (e.g., a bioerodable implant). See, e.g., U.S. Pat. Nos. 4,407,957 and 5,798,113, each incorporated herein by reference. Intrapulmonary delivery methods and apparatus are described, for example, in U.S. Pat. Nos. 5,654,007, 5,780,014 and 5,814,607, each incorporated herein by reference. Other useful parenteral delivery systems include ethylene-vinyl acetate copolymer particles, osmotic pumps, implantable infusion systems, pump delivery, encapsulated cell delivery, liposomal delivery, needle-delivered injection, needle-less injection, nebulizer, aeorosolizer, electroporation, and transdermal patch. Needle-less injector devices are described in U.S. Pat. Nos. 5,879,327, 5,520,639, 5,846,233 and 5,704,911, the specifications of which are herein incorporated by reference. Any of the formulations described above can be administered using these methods. Furthermore, a variety of devices designed for patient convenience, such as refillable injection pens and needle-less injection devices, may be used with the formulations of the present invention as discussed herein.

In a specific embodiment, isofagomine tartrate is administered as a powder-filled capsule, with lactose and magnesium stearate as excipients.

Combination Therapy.

The pharmaceutical composition may also include other biologically active substances in combination with the candidate compound (pharmacological chaperone) or may be administered in combination with other biologically active substances. Such combination therapy includes, but is not limited to, combinations with replacement enzymes such as Cerezyme®, Fabrazyme®, Aldurazyme®, Myozyme® and Replagal®; combinations with substrate reduction therapies (also known as substrate depravation therapy), such as Zavesca® or those molecules disclosed, for example, in U.S. Pat. Nos. 6,916,802 and 6,051,598, hereby incorporated by reference; and combinations with gene therapy vectors or cells containing a gene for GCase.

EXAMPLES

Example 1: Dosing Regimen for the Treatment of Gaucher Disease Using Isofagomine Tartrate The primary objective of the study is to evaluate the safety, tolerability and pharmacodynamics of two dose regimens of orally administered IFG tartrate in patients with type 1 GD. As indicated above, the prevalent mutation in Type 1 GD is N370S.

This will be a Phase 2, randomized, two dose group, open-label study to assess the safety and tolerability of isofagomine tartrate. The study will be conducted in treatment-naïve patients with type 1 GD between the ages of 18 and 65 years. Approximately 16 subjects will be enrolled.

This study will consist of a 7-day screening period, followed by randomization for qualifying subjects, a 24-week treatment period, which will be followed by a 14-day follow-up period.

Visits are scheduled at Day −7 (±3 days), Day 1 (±3 days), Day 7 (±3 days), Day 14 (±3 days), Day 28 (±3 days), Day 56 (±3 days), Day 84 (±3 days), Day 112 (±3 days), Day 140 (±3 days), Day 168 (±3 days) and Day 182 (±3 days). If a subject is withdrawn from the study after Day 1 and prior to study completion, the subject will be encouraged to undergo all procedures scheduled at Day 168 (visit 10).

At Day 1, subjects will be randomized in equal proportions to one of the two following groups:
1. Isofagomine tartrate, 150 mg orally every day for 1 week followed by 150 mg every 4 days for 23 weeks
2. Isofagomine tartrate, 150 mg orally every day for 1 week followed by 150 mg every 7 days for 23 weeks IFG tartrate is administered in 25 mg capsules. Since a food effect is anticipated, patients will have no food for two hours prior and two hours following drug administration.

The secondary objective of the study is to assess pharmacodynamic effects of two dose groups of orally administered isofagomine tartrate in treatment-naïve patients with type 1 Gaucher disease. Secondary endpoints which will be evaluated are as follows:

β-glucocerebrosidase (GCase) levels in white blood cells
Glucocerebroside (GlcCer) levels in white blood cells
α-synuclein levels in plasma
Bone-specific alkaline phosphatase activity in plasma (BAP) activity in plasma
Chitotriosidase activity in plasma
Interleukin 8 levels in plasma
Interleukin 17 levels in plasma
Macrophage Inflammatory Protein 1α (MIP-1α) level in plasma
Pulmonary and activation regulated chemokine (PARC) activity in plasma
Tartrate-resistant acid phosphatase 5b (TRACP 5b) activity in plasma
Vascular Endothelial Growth Factor (VEGF) levels in plasma
Change in liver volume from baseline
Change in spleen volume from baseline
Change in hemoglobin level from baseline
Change in hematocrit level from baseline
Change in platelet count from baseline
Change in bone mineral density of left or right femoral bones from baseline
Change in bone mineral density of the spine from baseline
Change in radiographic findings of the left or right femoral bones from baseline
Change in radiographic findings of spine from baseline The post-baseline pharmacodynamics parameters will be compared with baseline values by a two-tailed paired t-test procedure at the 95% confidence level. A repeated measure analysis of variance model will be invoked to determine the treatment effects on the values of pharmacodynamic parameters. In this analysis model, genotype and subject within genotype will be random effects, treatment, visit and visit-by-treatment interaction will be fixed effects and baseline value will be the covariate. An autoregressive model will be used to model the covariance structure among different time points. The treatment comparison will be assessed at the 5% significance level. In addition, the 95% confidence interval for the treatment difference will be provided.

It is anticipated that one or both of these loading/interval dosing regimens using IFG will be therapeutically effective for the treatment of Gaucher disease. Some genotypes anticipated to respond to this dosing regimen include but are not limited to the following: N370S/N370S, N370S/L444P, N370S/84insG, N370S/R163X, N370S/Y212H, L444P/del 136T, L444P/F216Y, L444P/L174F, G202R/R463C, L444P/L444P, and K79N/complex B exon 9/10 (type 3 GD).

Example 2: Dosing Regimen for the Treatment of Gaucher Disease Using Isofagomine Tartrate The primary objective of the study is to evaluate the safety, tolerability and pharmacodynamics of one dose regimen of orally administered IFG tartrate in patients with type 1 GD.

This will be a Phase 2, randomized, two dose group, open-label study to assess the safety and tolerability of isofagomine tartrate. The study will be conducted in patients with type 1 GD between the ages of 18 and 65 years. Approximately 16 subjects will be enrolled.

Visits are scheduled at Day −7 (±3 days), Day 1 (±3 days), Day 7 (±3 days), Day 14 (±3 days), Day 28 (±3 days), Day 56 (±3 days), Day 84 (±3 days), Day 112 (±3 days), Day 140 (±3 days), Day 168 (±3 days) and Day 182 (±3 days). If a subject is withdrawn from the study after Day 1 and prior to study completion, the subject will be encouraged to undergo all procedures scheduled at Day 168 (visit 10).

This study will consist of a 7-day screening period, followed by randomization for qualifying subjects, a 24-week treatment period, which will be followed by a 14-day follow-up period.

At Day 1, subjects will be randomized in equal proportions to placebo or Isofagomine tartrate, 150 mg orally every 3 days for the entire treatment period. IFG tartrate is administered in 25 mg capsules. Since a food effect is anticipated, patients will fast for two hours prior and two hours following drug administration.

Evaluation of secondary objectives will be performed as outlined above for Example 1.

It is anticipated that this dosing regime will be therapeutically effective for the treatment of Gaucher disease.

Example 3: Administration of Single Dose DGJ to Evaluate Safety, Tolerability and Pharmacokinetics, and Affect on α-Galatosidase A Enzymatic Activity This example describes a randomized, double blind, placebo controlled Phase Ib study of twice daily oral doses of DGJ to evaluate the affects of DGJ on safety, tolerability, pharmacokinetics, and α-Galatosidase A (α-GAL) enzymatic activity in healthy volunteers.

Study Design and Duration.

This study was first-in-man, single-center, Phase Ib, randomized, double-blind, twice daily-dose, placebo controlled study to evaluate the safety, tolerability, pharmacokinetics, and α-GAL enzymatic activity affects of DGJ following oral administration. The study tested two groups of of 8 subjects (6 active and 2 placebo) who received a twice daily-dose of 50 or 150 mg b.i.d. of DGJ or placebo administered orally for seven consecutive days, accompanied by a seven day follow up visit. Subjects were housed in the treatment facility from 14 hours prior to dosing until 24 hours after dosing. Meals were controlled by schedule and subjects remained ambulatory for 4 hours post drug administration Pharmacokinetic parameters were calculated for DGJ in plasma on Day 1 and Day 7. In addition, the cumulative percentage of DGJ excreted (12 hours post dose) in urine was calculated. α-GAL activity was calculated in white blood cells (WBC) before dosing began, and again at 100 hours, 150 hours, and 336 hours into the trial.

Study Population.

Subjects were healthy, non-institutionalized, non-smoking male volunteers between 19 and 50 years of age (inclusive) consisting of members of the community at large.

Safety and Tolerability Assessments.

Safety was determined by evaluating vital signs, laboratory parameters (serum chemistry, hematology, and urinalysis), ECGs, physical examination and by recording adverse events during the Treatment Period.

Pharmacokinetic Sampling.

Blood samples (10 mL each) were collected in blood collection tubes containing EDTA before dosing and at the following times thereafter: 0.25, 0.5, 0.75, 1, 1.5, 2, 3, 4, 5, 6, 7, 8, 9, 10, 11 and 12 hours. Blood samples were cooled in an ice bath and centrifuged under refrigeration as soon as possible. Plasma samples were divided into two aliquots and stored at 20±10° C. pending assay. At the end of the study, all samples were transferred to MDS Pharma Services Analytical Laboratories (Lincoln) for analysis. The complete urine output was collected from each subject for analysis of DGJ to determine renal clearance for the first 12 hours after administration of DGJ on days 1 and 7.

WBC α-GAL Enzymatic Activity Sampling.

Blood samples (10 mL each) were collected in blood collection tubes containing EDTA and WBC extracted before dosing and at the following times thereafter: 100 hours, 150 hours, and 336 hours. Samples were treated as described above, and WBC α-GAL enzymatic activity levels were determined as described in Desnick, R. J. (ed) *Enzyme therapy in genetic diseases*. Vol 2. Alan R Liss, New York, pp 17-32. Statistical Analysis. Safety data including laboratory evaluations, physical exams, adverse events, ECG monitoring and vital signs assessments were summarized by treatment group and point of time of collection. Descriptive statistics (arithmetic mean, standard deviation, median, minimum and maximum) were calculated for quantitative safety data as well as for the difference to baseline. Frequency counts were compiled for classification of qualitative safety data. In addition, a shift table describing out of normal range shifts was provided for clinical laboratory results. A normal-abnormal shift table was also presented for physical exam results and ECGs.

Adverse events were coded using the MedDRA version 7.0 dictionary and summarized by treatment for the number of subjects reporting the adverse event and the number of adverse events reported. A by-subject adverse event data listing including verbatim term, coded term, treatment group, severity, and relationship to treatment was provided. Concomitant medications and medical history were listed by treatment.

Pharmacokinetic parameters were summarised by treatment group using descriptive statistics (arithmetic means, standard deviations, coefficients of variation, sample size, minimum, maximum and median).

Results

No placebo-treated subjects had AEs and no subject presented with AEs after receiving 50 mg b.i.d. or 150 mg b.i.d. DGJ. DGJ appeared to be safe and well tolerated by this group of healthy male subjects as doses were administered at 50 mg b.i.d. and 150 mg b.i.d.

Laboratory deviations from normal ranges occurred after dosing, but none was judged clinically significant. There were no clinically relevant mean data shifts in any parameter investigated throughout the course of the study. No clinically relevant abnormality occurred in any vital sign, ECG, or physical examination parameter.

Pharmacokinetic Evaluation.

The following table summarizes the pharmacokinetic data obtained during the study.

TABLE 5

| | 50 mg bid dose | | 150 mg bid dose | |
| --- | --- | --- | --- | --- |
| | Day 1 | Day 7 | Day 1 | Day 7 |
| Cmax (μM) | 2.3 ± 0.3 | 3.9 ± 0.5 | 11.3 ± 1.5 | 10.8 ± 1.4 |
| tmax (h) | 2.9 ± 0.4 | 2.5 ± 0.4 | 3.1 ± 0.4 | 2.9 ± 0.4 |
| t½ (h) | 2.5 ± 0.1 | | 2.4 ± 0.05 | |
| Cmin (μM) | | 0.4 ± 0.03 | | 1.2 ± 0.1 |
| 12 h cumulative renal excretion (%)[a] | 16 ± 6 | 48 ± 7 | 42 ± 7 | 60 ± 5 |

[a]Cumulative percentage of DGJ excreted over the 12-hour post dose period.

The pharmacokinetics of DGJ were well characterized in all subjects and at all dose levels. On average, peak concentrations occurred at approximately 3 hours for all dose levels. $C_{max}$ of DGJ increased in a dose-proportional manner when doses were increased from 50 mg to 150 mg.

The mean elimination half-lives ($t_{1/2}$) were comparable at dose levels of 50 and 150 mg on Day 1 (2.5 vs. 2.4 hours).

The mean percentage of DGJ excreted over the 12-hour post dose period was 16% and 42% at dose levels of 50 and 150 mg, respectively, on Day 1, increasing to 48% and 60%, respectively, on Day 7.

α-Galactosidase A (α-GAL) Enzymatic Activity.

The α-GAL enzymatic activity data obtained during the study is shown in FIG. 1. DGJ did not inhibit WBC α-GAL enzymatic activity in subjects at dosages of 50 mg b.i.d. or 150 mg b.i.d. Furthermore, DGJ produced a dose-dependent trend of increased WBC α-GAL activity in healthy volunteers. α-GAL enzymatic levels were measured in WBC of subjects administered placebo, 50 mg b.i.d. DGJ, and 150 mg b.i.d. DGJ. Placebo had no affect on WBC α-GAL enzymatic levels. Variations in enzymatic levels in response to placebo were not clinically significant. Both 50 mg b.i.d. and 150 mg b.i.d. DGJ increased normalized WBC α-GAL enzymatic levels. In response to 50 mg b.i.d. DGJ, WBC α-GAL enzymatic activity increased to 120%, 130%, and 145% pre-dose levels at 100 hours, 150 hours, and 336 hours post-dose, respectively. In response to 150 mg b.i.d. DGJ, WBC α-GAL enzymatic activity increased to 150%, 185%, and 185% pre-dose levels at 100 hours, 150 hours, and 336 hours post-dose, respectively.

Example 4: Dosing Regimen for the Treatment of Fabry Disease Using DGJ Hydrochloride This example describes a dosing regiment using DGJ that is contemplated for the treatment of Fabry patients.

Patient Enrollment.

Fabry patients with known missense mutations in α-GAL (verified by genotype); patients currently receiving ERT (Fabrazyme®) who are willing to stop ERT for up to 6 months; or newly diagnosed patients who have never been treated with ERT.

Study Design.

Patients will be orally administered DGJ hydrochloride or a placebo daily for 7 days at a dose of 250 mg/day. This is the Initial Enzyme Build-Up Phase. Following completion of the first phase, the Maintenance Phase will begin wherein DGJ or a placebo is administered at a Maintenance dose of 150 mg every other day.

GL-3 Deposits.

Skin, kidney and heart biopsies will be performed at baseline, 3 months and six months and evaluated for GL-3 deposits in skin fibroblasts, cardiac myocytes, and various renal cells. It is anticipated that clearance of GL-3 will be observed in all cells. Clearance in cardiac myocytes or renal podocytes or skin tissue has not previously been shown upon treatment with ERT (although changes in urinary sediment at 6 and 18 months of ERT suggested that accumulations of glycosphingolipids in renal tissues were cleared by enzyme replacement; *Clin Chim Acta.* 2005; 360(1-2):103-7).

α-Gal Activity.

In addition, α-GAL activity will be assessed in fractionated tissue obtained from biopsies and in blood leukocytes and plasma (from blood collected at baseline and every month). It is anticipated that DGJ treatment as monotherapy and in combination with ERT will increase α-GAL activity from about 2-fold to 10-fold above baseline in leukocytes, fibroblasts and plasma. It is also anticipated that increases in α-GAL activity will be observed in tissue, which has not been demonstrated with ERT treatment.

Urinalysis.

Urine and urinary sediment will be analysed at baseline and monthly for α-GAL and GL-3. In addition, the abnormal presence of other lipids, such as CTH, lactosylceramide, ceramide, and abnormal decrease or absence of glucosylceramide and sphingomyelin will also be evaluated Urine will also be analyzed for the presence of protein including albumin (proteinuria) and creatine to monitor the status of renal disease.

It is anticipated that DGJ treatment will reduce proteinurea and reduce GL-3 sediment.

Cardiac Analysis.

In addition to the biopsies described above, MRIs and echocardiogram with strain rate evaluations will be performed at baseline, 3 and 6 months to assess cardiac morphology (e.g., left ventricular hyertrophy) and cardiac function (e.g., congestive heart failure, ischemia, infarction, arrhythmia). Direct reduction in left ventricular hypertrophy, or increase in left ventricular ejection fraction, has never been demonstrated by other treatments. Hypertension will also be evaluated since hypertension (associated with renal dysfunction) can increase the risk for hemorrhagic stroke.

Electrocardiograms will be performed at baseline and at every visit for analysis of improvement in any conduction abnormalities, arrhythmias, bundle branch blocks, or tachy or bradycardia. Previous treatments have not shown improvements in patients presenting with these symptoms.

Renal Analysis.

Renal podocytes will be evaluated using light and electron microscopy for clearance of GL-3.

Brain Analysis.

MRI and MRA will be performed at baseline and at the end of the study to assess for a reduction in ischemic arease, which can cause ischemic strokes. The reduction in GL-3 buildup by DGJ is anticipated to reduce the incidence of strokes. Since replacement enzyme cannot cross the blood brain-barrier, improvements in brain ischemia has never been achieved with ERT.

Opthamology.

Opthalmologic exams will be performed to assess reduction in corneal and lens opacities such as cataracts.

Neuropathic Pain.

Subjective patient questionnaires will be administered to patients at baseline and at each monthly visit to evaluate reduction in acroparaesthesia. This may be evidence of clearance of GL-3 in the microvasculature of peripheral nerve cells.

Neuropathy.

Quantitative Sensory Testing (CASE study) will be used to evaluate peripheral neuropathy.

Hypohidrosis.

Sweat glands will be evaluated using quantitative sudomotor axon reflex test (QSART), which assesses the small nerve fiblers that are linked to the eccrine sweat glands. Improvements in the sweat glands should correlate with an increase in sweating, and may also be evidence of clearance of GL-3 in the microvasculature of peripheral nerve cells. This analysis will be performed at baseline and at 3 and 6 months.

It is anticipated that this dosing regime will be therapeutically effective for the treatment of Fabry disease. Some specific missense mutations expected to respond to treatment with DGJ include, but are not limited to, L32P, N34S, T41L, M51K, E59K, E66Q, 191T, A97V, R100K, R112C, R112H, F113L, G132R, A143T, G144V, S148N, D170V, C172Y, G183D, P205T, Y207S, Y207C, N215S, R227X, R227Q, A228P, S235C, D244N, P259R, N263S, N264A, G271C, S276G, Q279E, M284T, W287C, I289F, F295C, M296I, M296V, L300P, R301Q, V316E, N320Y, G325D, G328A, R342Q, R356W, E358A, E358K, R363C, R363H, and P409A.

Example 5: Dosing Regimens for the Treatment of Fabry Disease Using DGJ Hydrochloride This example describes a Phase II study of DGJ in Fabry patients.

Patient Enrollment.

Fabry patients with known missense mutations in α-GAL (verified by genotype); patients currently receiving ERT (Fabrazyme®) who are willing to stop ERT for up to 6 months; or newly diagnosed patients who have never been treated with ERT.

Study Design.

Eight patients in the study received an ascending dose of 25, 100, and then 250 mg b.i.d. over 6 weeks, followed by 50 mg/day for the remainder of the study. Three patients in the study received 150 mg of DGJ every other day throughout the entire study.

Some of the same surrogate markers as described for Example 4 will be monitored during the study.

Results

α-GAL Activity.

Figure 7:
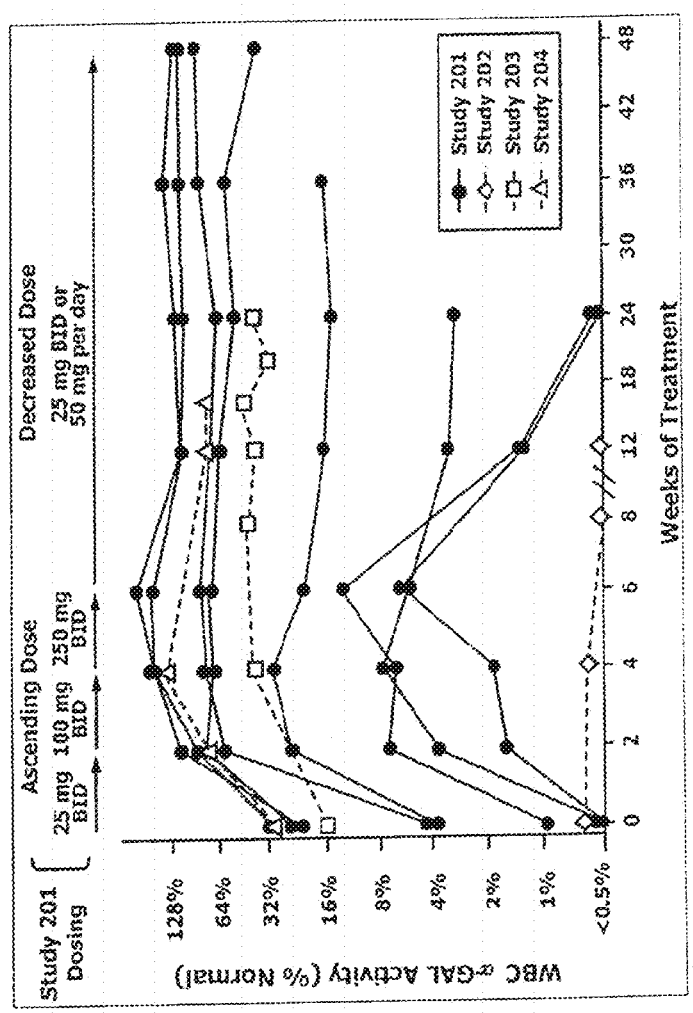
FIG. 7 shows results from 11 Fabry patients treated with DGJ according to two specific dosing regimens.

The available data from the first eleven patients treated with DGJ for at least 12 weeks suggest that treatment with DGJ leads to an increase in the activity of the enzyme deficient in Fabry disease in 10 of the 11 patients. Eight patients in the study received an ascending dose of 25, 100, and then 250 mg b.i.d. over 6 weeks, followed by 50 mg/day for the remainder of the study (represented by closed circles) (FIG. 7) Three patients in the study received 150 mg of DGJ every other day throughout the entire study (represented by closed circles). For purposes of calculating the percentage of normal in the table, the level of α-GAL that is normal was derived by using the average of the levels of α-GAL in white blood cells of 15 healthy volunteers from the multiple-dose Phase I study. The 11 patients represented 10 different genetic mutations and had baseline levels of α-GAL that ranged from zero to 30% of normal.

GL-3 Levels.

Kidney GL-3 levels were assessed by an independent expert using electron microscopy. Data available for two patients to date showed an observed decrease in GL-3 in multiple cell types of the kidney of one patient after 12 weeks of treatment (mesangial cells and cells of the glomerular endothelium and distal tubules). A second patient showed a decrease of GL-3 levels in the same kidney cell types after 24 weeks of treatment, but these decreases were not independently conclusive because of the patient's lower levels of GL-3 at baseline. Both patients showed a decrease of GL-3 levels in other kidney cell types including cells of the interstitial capillaries, but the decreases were less than 1 unit and, thus, even though the post-treatment. These initial results are consistent with the GL-3 reductions observed after oral administration of Amigal to mice that produce defective human α-GAL.

Skin GL-3 levels at baseline and after treatment as assessed by light and electron microscopy are available for 10 patients. Seven patients had skin GL-3 levels that were normal or near normal both before and after treatment. Results for the three other patients were difficult to interpret because they showed evidence of a decrease in GL-3 in some skin cell types and an increase in GL-3 in other skin cell types, with variability over time.

Example 6: Dosing Regimens for the Treatment of Fabry Disease Using DGJ Hydrochloride This example describes a study of DGJ (1-Deoxygalactonorjirimycin) in Fabry patients.

Patient Enrollment.

Eighteen male and nine female Fabry patients with known missense mutations in α-GAL (verified by genotype) were enrolled. (One of the male patients did not complete the study). Thirteen of these patients were naive to ERT, while fourteen patients previously received ERT (Fabrazyme®), but had discontinued ERT for 21-274 days prior to the study. The Fabry disease of the patients enrolled in this study was caused by one of the following missense mutations in the Fabry gene: A143T, T411, A97V, M51K, G328A, S276G, L300P, L415P, P259R, R301Q, N215S, P205T, F295C, C94S, or R112C.

Study Design.

Nine male patients in the study (one male did not complete the study) received an ascending dose of 25, 100, and then 250 mg b.i.d. for 6 weeks (2 weeks at each dosage level), followed by six weeks of 25 mg b.i.d. or 50 mg/day for the remainder of the study (Group A). Four male patients received a single 150 mg Q.O.D for 12 weeks (Group B); while five male patients received 150 mg Q.O.D. for 24 weeks (Group C). Finally nine female patients were randomized to receive one of three dosages: 50, 150 or 250 mg Q.O.D for 12 weeks (Group D) (FIG. 8).

α-Gal Activity.

Enzymatic activity of α-Gal in leukocytes (white blood cells; WBCs) of the patients was measured as a percentage of the average α-Gal activity in white blood cells of 15 healthy volunteers. α-GAL activity was assessed in fractionated tissue obtained from biopsies, and in blood leukocytes and plasma (from blood collected at baseline and every month).

GL-3 Deposits.

Kidney biopsies were performed at baseline, 12 weeks and 24 weeks post-treatment and evaluated for GL-3 deposits in various renal cells. GL-3 presence in the tissue was examined histologically as well as through the use of mass spectroscopy. Light microscopic analysis of kidney biopsies was performed, wherein the accumulation of GL-3 in the tissue was classified in a manner similar to the classification analysis performed in *Kidney International*, Vol. 62 (2002), pp. 1933-1946 which is hereby incorporated by reference. Cells were classified as containing no GL-3 accumulation ("0"); mild GL-3 accumulation ("1"); moderate GL-3 accumulation ("2"); or severe GL-3 accumulation ("3").

Urinalysis.

Urine was analysed at baseline and periodically every 2-6 weeks for GL-3.

Cardiac Analysis.

In addition to the biopsies described above, MRIs, electrocardiograms and echocardiograms with strain rate evaluations was performed at baseline and periodically throughout the study to assess cardiac morphology (e.g., left ventricular hyertrophy) and cardiac function (e.g., ejection fraction and conduction/rhythm abnormalities).

Renal Analysis.

Renal function was evaluated using glomerular filtration rate (GFR).

Neuropathic Pain.

Patients self-reported changes in symptoms at the end of 12 or 24 week treatment period to evaluate, inter alia, reduction in acroparaesthesia. This may be evidence of clearance of GL-3 in the microvasculature of peripheral nerve cells.

Results

Male Patients

α-GAL Activity.

Figure 9:
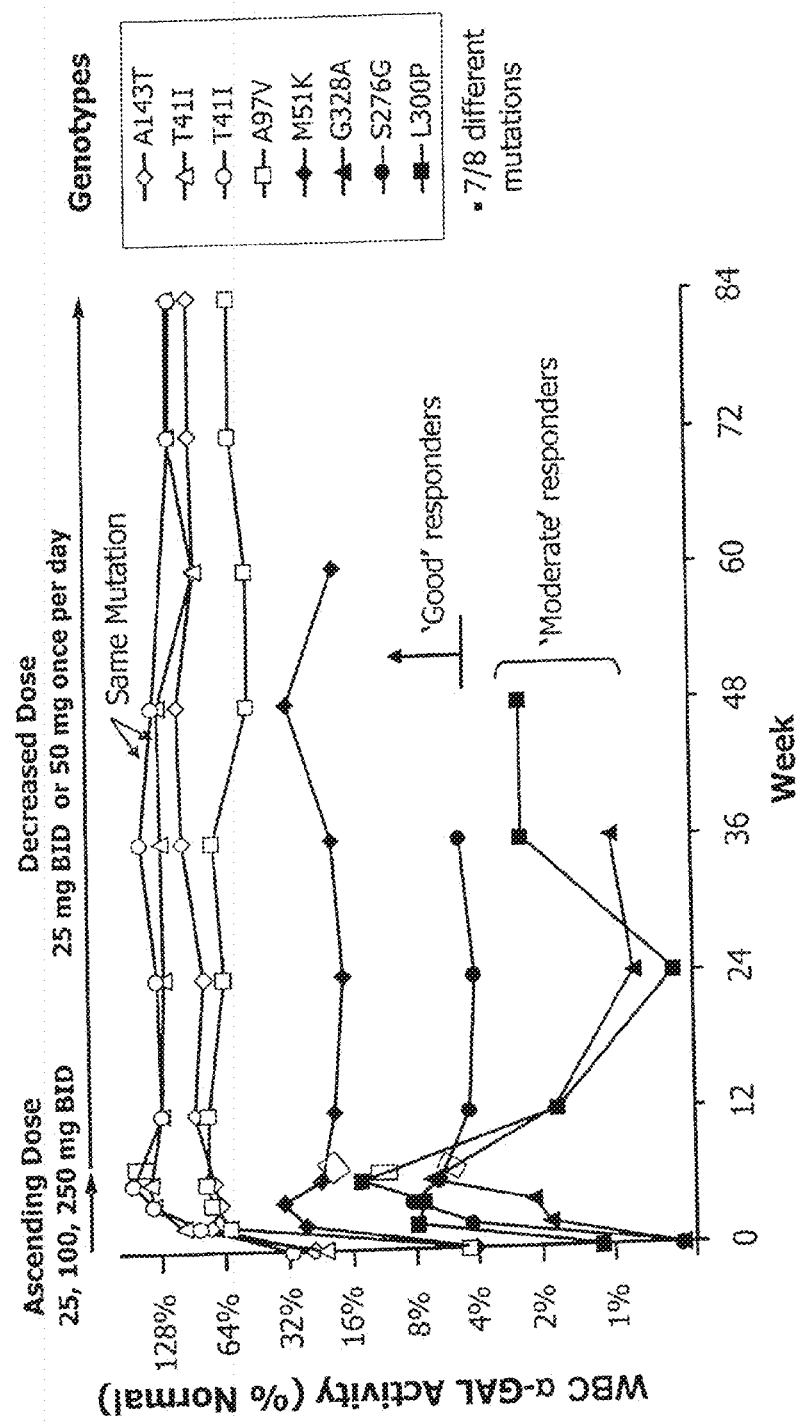
FIG. 9 is a graph of the α-GAL activity in white blood cells for 8 male patients having particular missense mutations.

The α-Gal activity data from the eight male patients receiving treatment according to the Group A protocol is shown in FIG. 9. Patients were classified as "good" responders if, following treatment, they exhibited an absolute increase in enzyme activity that was greater than 3% of normal α-GAl activity and further, such increase was greater than 33% relative to the mutant's pre-treatment α-GAL activity level. Patients were classified as "moderate" responders if they exhibited an absolute increase greater than 1-3% of normal α-GAL activity that was also greater than 33% relative to the mutant's pre-treatment α-GAL activity level.

Figure 10:
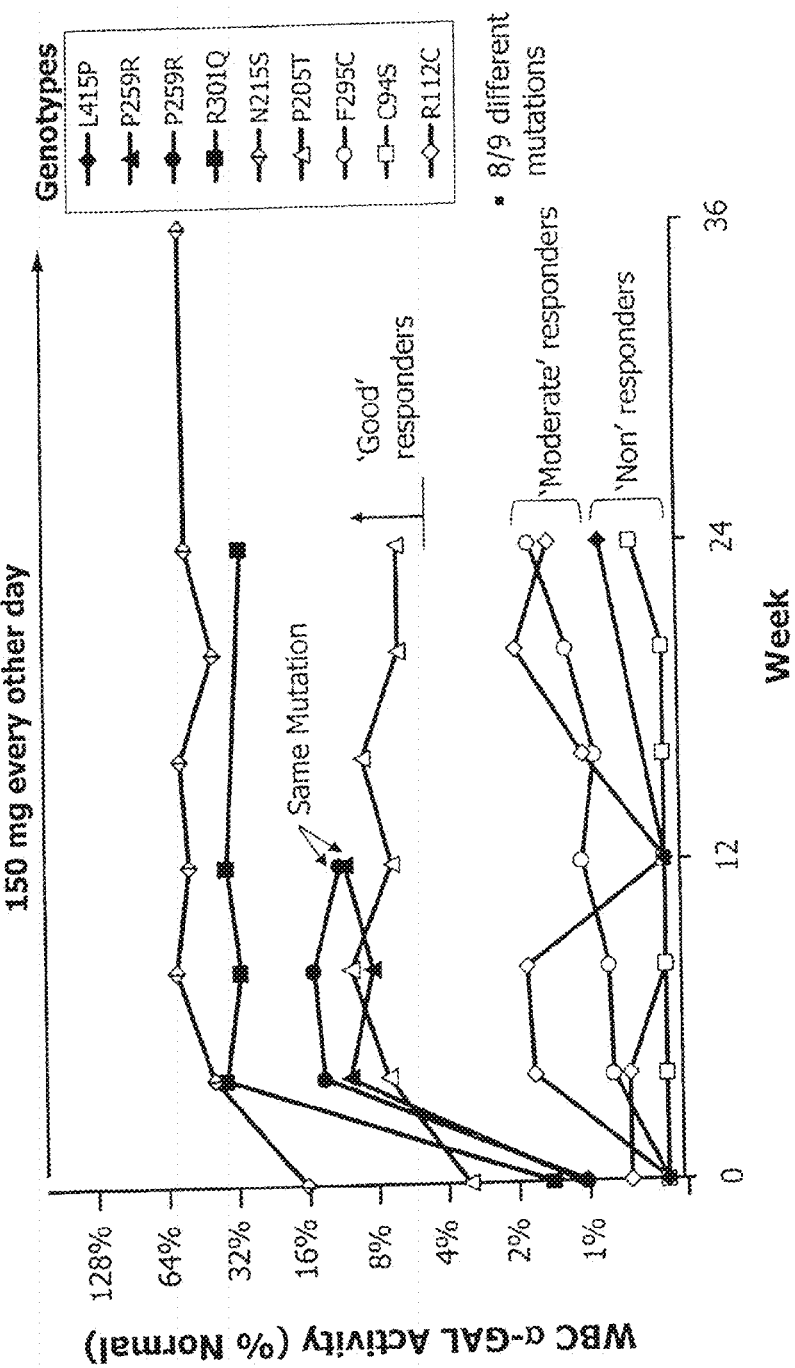
FIG. 10 is a graph of the α-GAL activity in white blood cells for 9 male patients having particular missense mutations.

The data from the nine male patients receiving treatment according to protocols Group B and Group C are shown in FIG. 10. "Good" responders where characterized by an increase in α-Gal activity to about 8% of normal enzyme activity by week 12 of the treatment. "Moderate" responders were those patients that exhibited an increase in α-Gal activity to about 1.5% normal enzyme activity by 24 weeks post-treatment. "Non" responders were those patients that never exhibited an increase in α-Gal activity above 1% normal enzyme activity during treatment.

Figure 11:
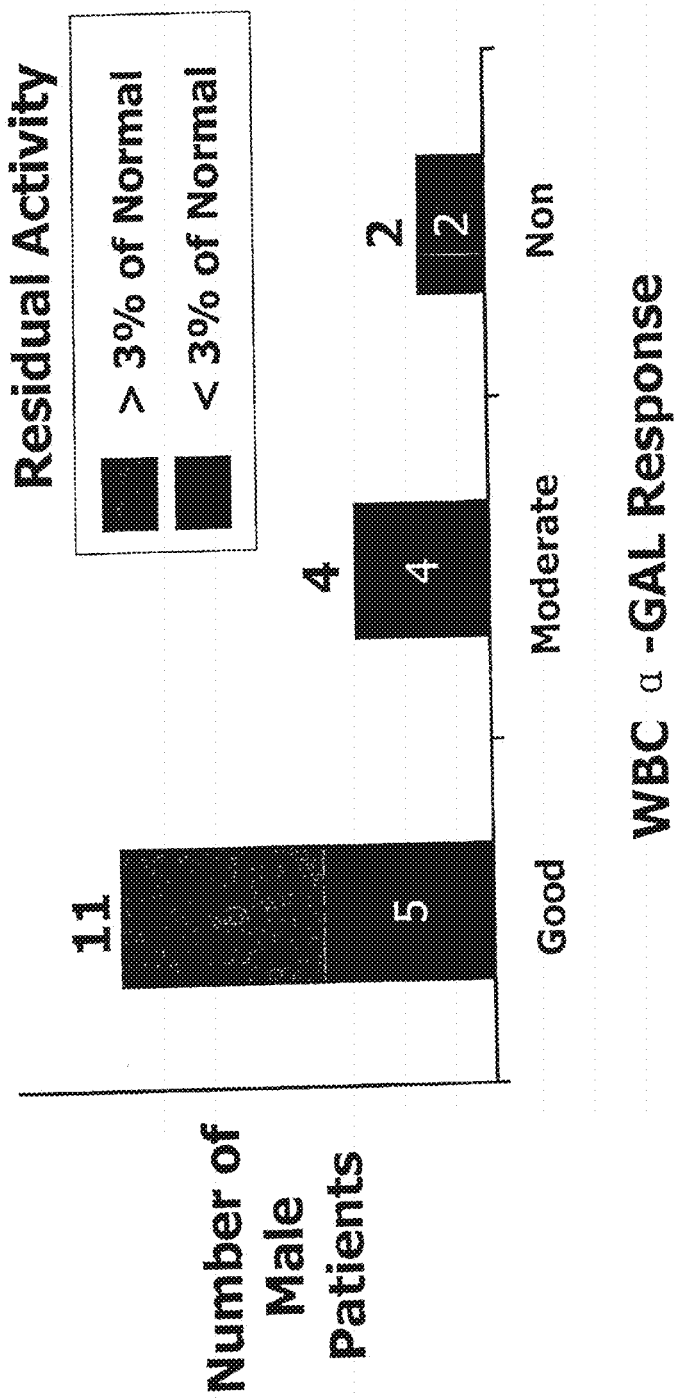
FIG. 11 is a response summary for the dosing regimen described in Example 6.

There were eleven "good" responders in the study, while four patients were "moderate" responders and two patients were "non" responders. Of the good responders, six patients had a residual α-Gal activity of greater than 3% of normal enzyme activity prior to initiation of the study, while five of the good responders and all of the moderate and non-responders exhibited a residual α-Gal activity of less than 3% normal level (FIG. 11).

Figure 12:
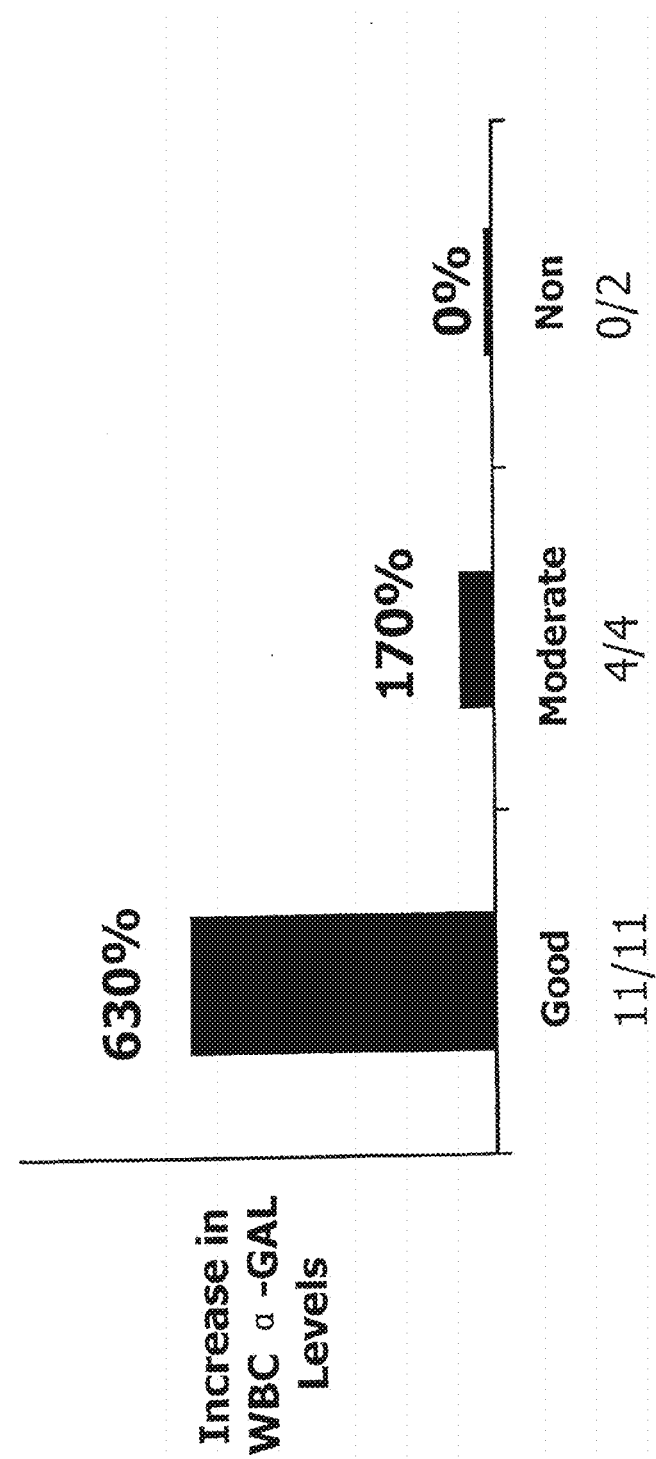
FIG. 12 is graph demonstrating the increase in α-GAL activity in white blood cells for the three groups designated in Example 6.
Figure 13:
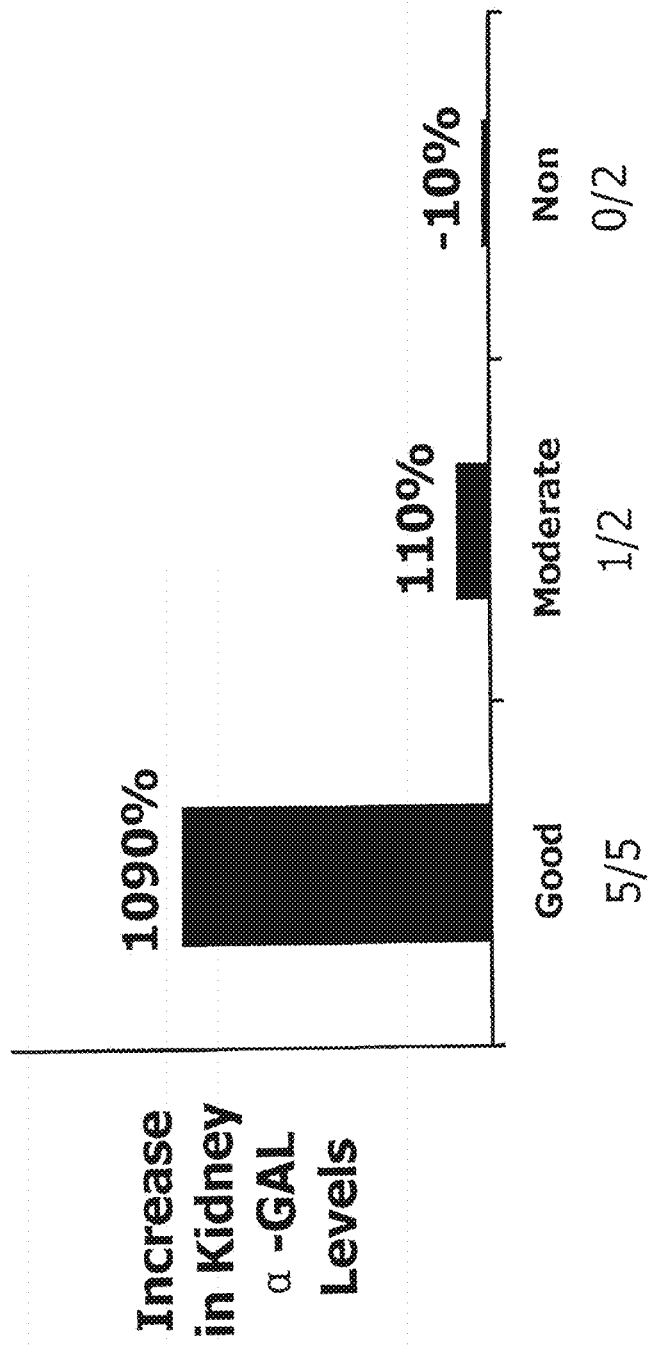
FIG. 13 is graph demonstrating the increase in α-GAL activity in kidney tissue for the three groups designated in Example 6.

As shown in FIGS. 12 and 13, the eleven "good" responders exhibited a mean 630% increase in WBC α-Gal activity when pre and post treatment activity levels of each patient were compared. Six of the good responders also showed a mean 1090% increase in kidney α-Gal activity. All four "moderate" responders displayed a mean 170% increase in leukocyte α-Gal activity during treatment, and one moderate responder exhibited a mean 100% increase in kidney α-Gal activity. None of the "non" responders exhibited any overall increase in either leukocyte or kidney α-Gal activity following treatment.

Urinalysis of GL-3.

GL-3 in the urine of treated patients results primarily from tubule cells shed from the kidneys. Elevated levels of GL-3 are detectable in all Fabry patients. In the male patients who were characterized as "good" responders, patients displayed a 38% mean decrease in urine GL-3 levels following treatment, while eight of the eleven good responders experienced a decrease that was greater than 10%. While both the "moderate" responders and "non" responders showed overall increases in urine GL-3 following treatment, one patient in the moderate group displayed a decrease in GL-3 levels that was greater than 10% following treatment (FIG. 14).

Kidney Analysis.

Kidney GL-3 levels were assessed using histological and mass spectroscopic analysis. Kidney biopsies were examined in four of the "good" responders, two of the "moderate" responders, and two of the "non" responders. Accumulation of GL-3 was examined in three different kidney cell types: interstitial capillaries, distal tubules, and podocytes. With respect to the good responders, one patient displayed a decrease in interstitial capillary GL-3, one patient experienced an undetectable change in interstitial capillary GL-3, and one patient experienced no change in interstitial capillary GL-3. With regard to distal tubules, three of the good responders experienced a decrease in GL-3, and one good responder experienced an increase in GL-3. As for podocyte cell GL-3 levels following treatment, all four good responders experienced no change GL-3 levels (See FIG. 15A).

With regard to overall GL-3 levels in the kidney biopsies, two of the good responders showed a decrease in GL-3 following treatment, while two good responders showed no change in GL-3 levels. As for the moderate responders, two patients showed a decrease in GL-3 levels. One non-responders showed a decrease in GL-3 levels, while one non-responding patient exhibited an increase in GL-3 (See FIG. 15B).

Additionally, as was seen in the urinalysis, mass spectroanalysis of kidney biopsies revealed that the good responders experienced a mean decrease in kidney GL-3 levels (28%) following treatment, with 3 of the good responders exhibiting a decrease of greater than 10% (FIG. 16).

Figure 17A:
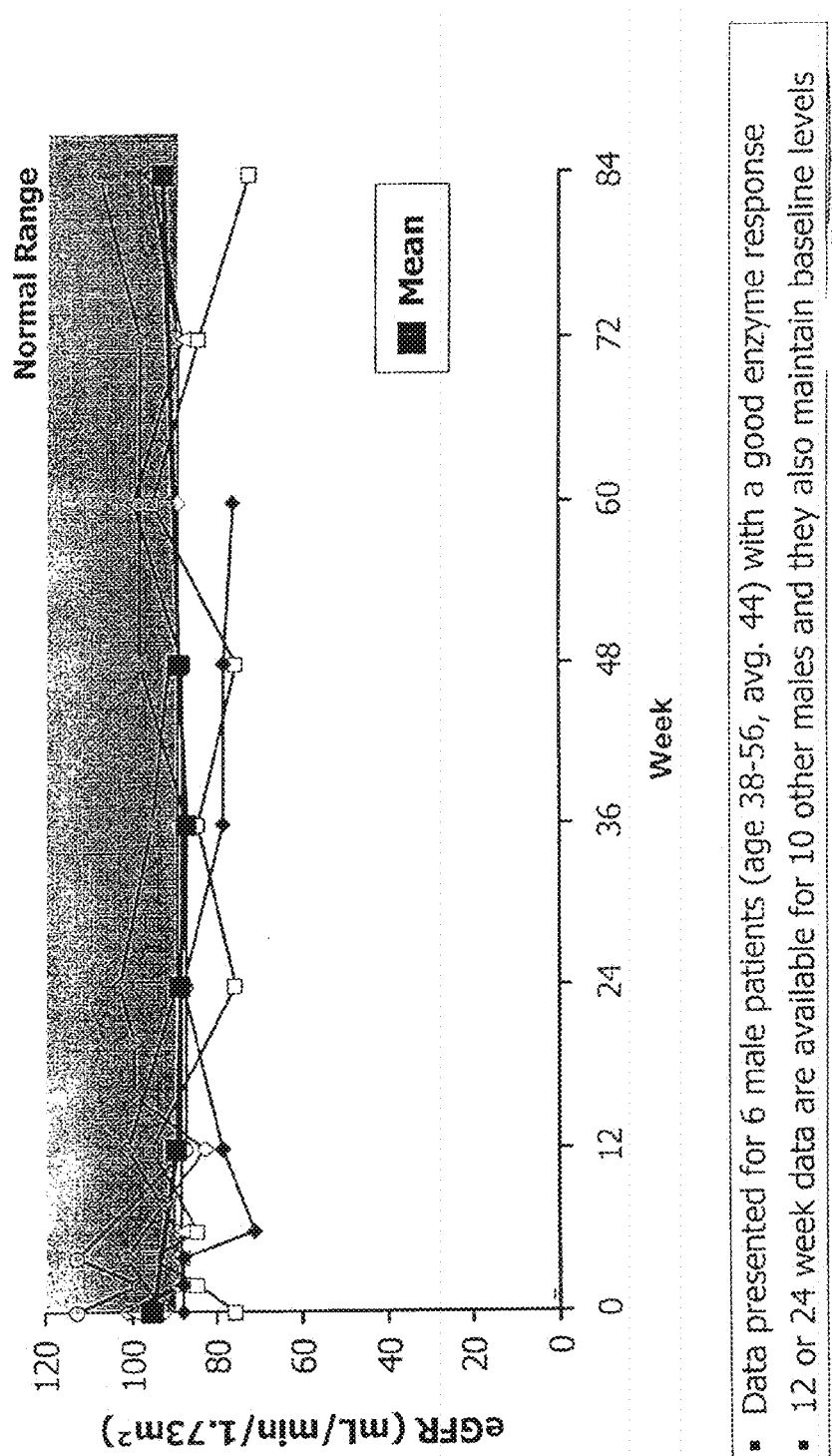

Renal function was measured using glomerular filtration rate (GFR) (MDRD equation was used to estimate GFR using serum creatinine adjusted for age, gender and race). Approximately half of all Fabry patients have an abnormally low GFR (<90 ml/min/1.73 m$^2$). Natural history studies suggest that Fabry patients exhibit a progressive decline in GFR at a rate of about 5-15 units per year depending on age and kidney disease stage. As shown in FIG. 17A-B, the good responders maintained a mean eGFR within the normal eGFR range of 90-120 ml/min/1.73 m$^2$ during the entire treatment procedure (FIG. 17A), while the predicted mean eGFR level of untreated individual is projected to continue declining below 90 ml/min/1.73 m$^2$ (FIG. 17B).

Cardiac Function.

Prior to treatment, about half of all the patients had conduction/rhythm abnormalities as assessed via ECG at baseline prior to treatment, and at the last visit following treatment (the last visit was between 12-24 weeks after the study began)(data not shown). Three of the "good" responders had an abnormally high left ventricle mass prior to treatment. One of these patients displayed an 8% decrease in left ventricle mass following 12 weeks of treatment, while 2 exhibited no change in left ventricle mass after 48 weeks of treatment (data not shown). Both decreases in and maintenance of left ventricle mass is of interest since Fabry patients typically exhibit an increase in left ventricle mass over time. Furthermore, three of the good responders presented an abnormal ejection fraction prior to treatment, wherein two of the patients displayed an ejection fraction in the normal range (>55%) following treatment (FIG. 18).

Self-Reported Analysis.

Patients self-reported changes in symptoms, such as acroparaesthesias associated with Fabry disease, at end of the 12 or 24 week treatment period, and every 12 weeks in extension. Seven of the "good" responders reported improved gastrointestinal function and a decrease in pain; increases in the ability to walk, drive and sleep; and improved sweating. Two of the good responders reported no change in Fabry symptoms. Of the "moderate" and "non" responders, one person reported increased sweating with a persistence of pain, and three reported no changes in Fabry symptoms (FIG. 19).

Female Patients

Because of X-chromosome inactivation in female cells, the phenotype of a diseased cell in a tissue sample expressing a mutant Fabry gene will be masked by healthy cells in the sample. Therefore, to assess the expected enzyme responses in diseased cells, each mutation the female patients exhibited was constructed and tested in vitro. Thus, based on the in vitro analysis, the different mutations were classified as "expected good responders" and "expected non-responders." Five of the patients were classified as expected good responders while four patients were classified as expected non-responders (data not shown).

α-GAL Activity.

All nine of the female patients treated in the study exhibited an increase in WBC α-Gal activity following treatment according to the Group D treatment protocol (mean increase of 146% compared to baseline enzyme levels prior to treatment) (data not shown).

Urinalysis of GL-3.

In the female patients who were characterized as "expected good" responders, the patients displayed a 20% mean decrease in urine GL-3 levels following treatment, while 3 of the 5 expected good responders experienced a decrease that was greater than 10%. The "non" responders showed an overall increases in urine GL-3 levels following treatment, although one patient displayed a decrease in GL-3 that was greater than 10% following treatment (FIG. 20).

Kidney Analysis.

Similar to the results observed in the urinalysis, mass spectoanalysis of kidney biopsies from the "expected good" responders displayed a mean decrease in kidney GL-3 levels (20%) following treatment, wherein two of the five expected good responders presented a decrease of greater than 10% following treatment (FIG. 21).

Self-Reported Analysis.

Patients self-reported changes in symptoms, such as acroparaesthesias associated with Fabry disease, at end of the 12 or 24 week treatment period, and every 12 weeks in extension. Four of the "expected good" responders reported decreases in pain; increases in the ability to walk, drive and sleep; and improved sweating. One of the expected good responders reported no change in Fabry symptoms. Of the "non" responders, one person reported a decrease in pain, while three reported no changes in Fabry symptoms or the appearance of symptoms such as anxiety, depression, or sleep difficulties (FIG. 22).

Example 7: Treatment of Pompe Disease Using 1-Deoxynorjirimycin 100 mg/kg of 1-Deoxynorjirimycin is administered ad libitum to mice for 28 days. α-glucosidase activity (GAA) in the heart is shown in FIG. 23 for whole tissue lysates (left) and based on immunoprecipitated GAA (right). This data appears similar preliminary results from gastrocnemius muscle analysis in response to 1-Deoxynorjirimycin.

1-Deoxynorjirimycin has been shown to be well tolerated in short-term safety studies in rats and monkeys at doses currently believed to be well above levels to be encountered in future clinical studies. For example, 1-Deoxynorjirimycin appears to be safe and well tolerated at single doses up to 600 mg. Repeat doses up to 2 grams per day for 2 weeks. All adverse events in patients receiving drug were mild or moderate in severity, and none were considered definitely or probably related to the study drug. 1-Deoxynorjirimycin is believed to have high oral bioavailability with a terminal half-life in plasma of approximately 4-8 hours.

GAA response to 1-Deoxynorjirimycin will be determined in freshly isolated leukocytes. GAA response will also be determined in patient-derived cell lines, skin fibroblasts and EBV-transformed lymphoblasts. DNA sequencing will be performed to confirm genotype information. Urinary tetra-saccharide levels in patients will also be assessed. Plasma cytokines and chemokines will be measured to identify potential markers of disease to monitor in clinical trials.

Example 8: DGJ (1-Deoygalactonorjirimycin Hydrochloride) Increases the Activity of α-galactosidase A (α-GAL)

This example describes a study of DGJ (1-Deoxygalactonorjirimycin) transgenic mice expressing a missense Fabry mutation. The example also describes the study of DGJ's affect on cell lines expressing various Fabry missense mutations.

Figure 24:
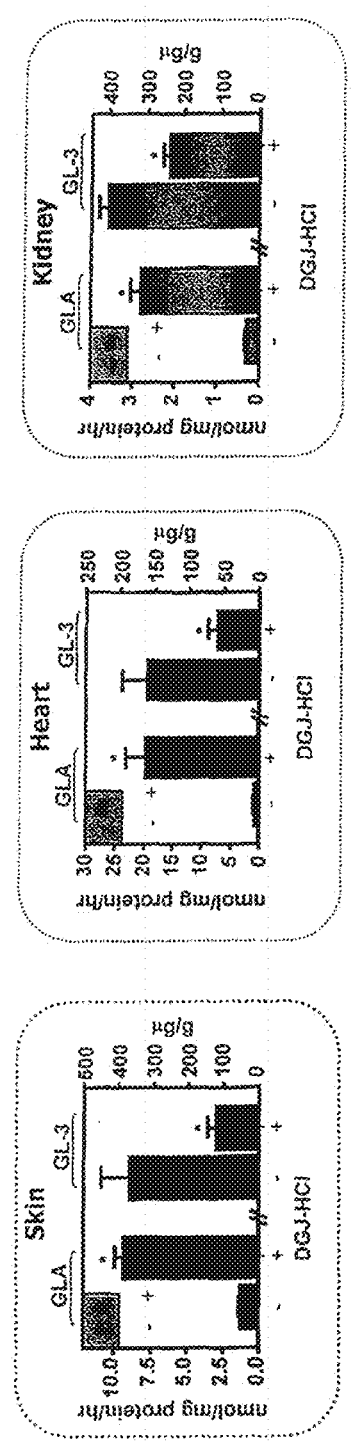
FIG. 24 is a graph demonstrating FLA and GL-3 results in the skin, heart and kidney as described in Example 8.
Figure 25:
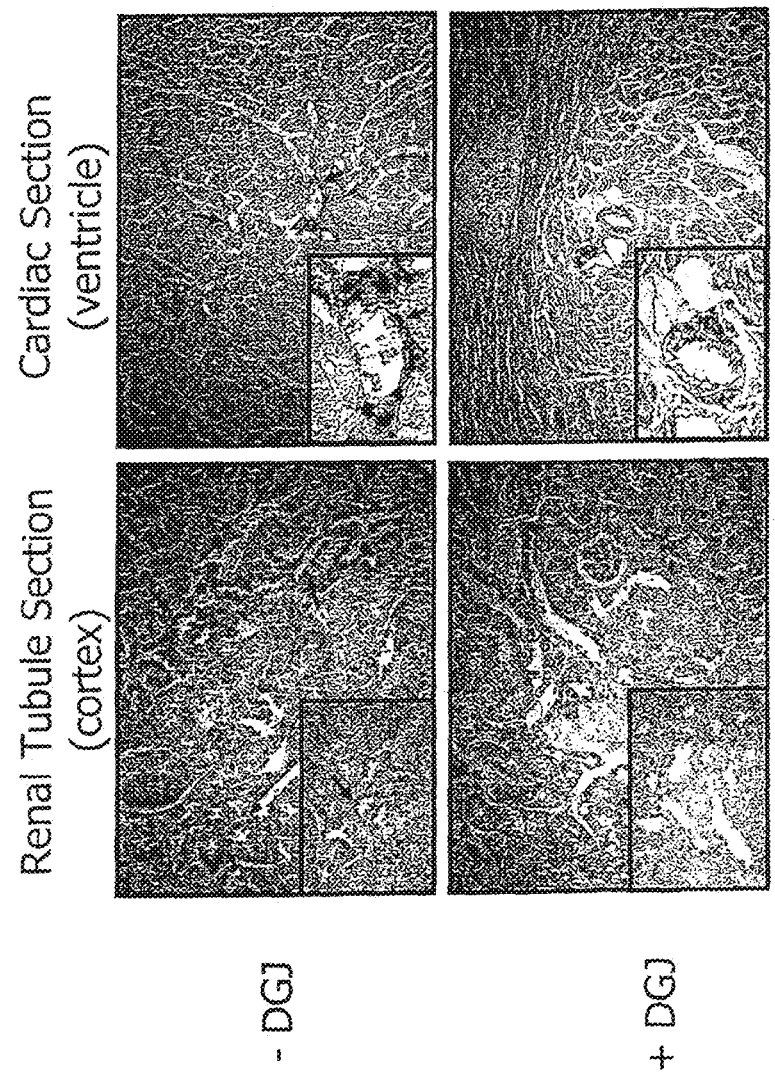

Transgenic mice expressing the R301Q Fabry missense mutation were administered DGJ ad libitum at 100 mg/kg for four weeks. Following the DGJ treatment, biopsies were taken of the skin, liver and kidney of the treated animals. α-GAL expression was measured in the tissue biopsies, as was the concentration of GL-3. As shown in FIG. 24, α-GAL expression was increased in the skin, heart and kidney following treatment with DGJ. Additionally, the concentration of GL-3 in the sampled tissues was reduced following DGJ treatment. Furthermore, as shown in FIG. 25, histological examination of renal tube sections and cardiac section showed that the presence of GL-3 aggregates was reduced following treatment with DGJ.

Figure 26:
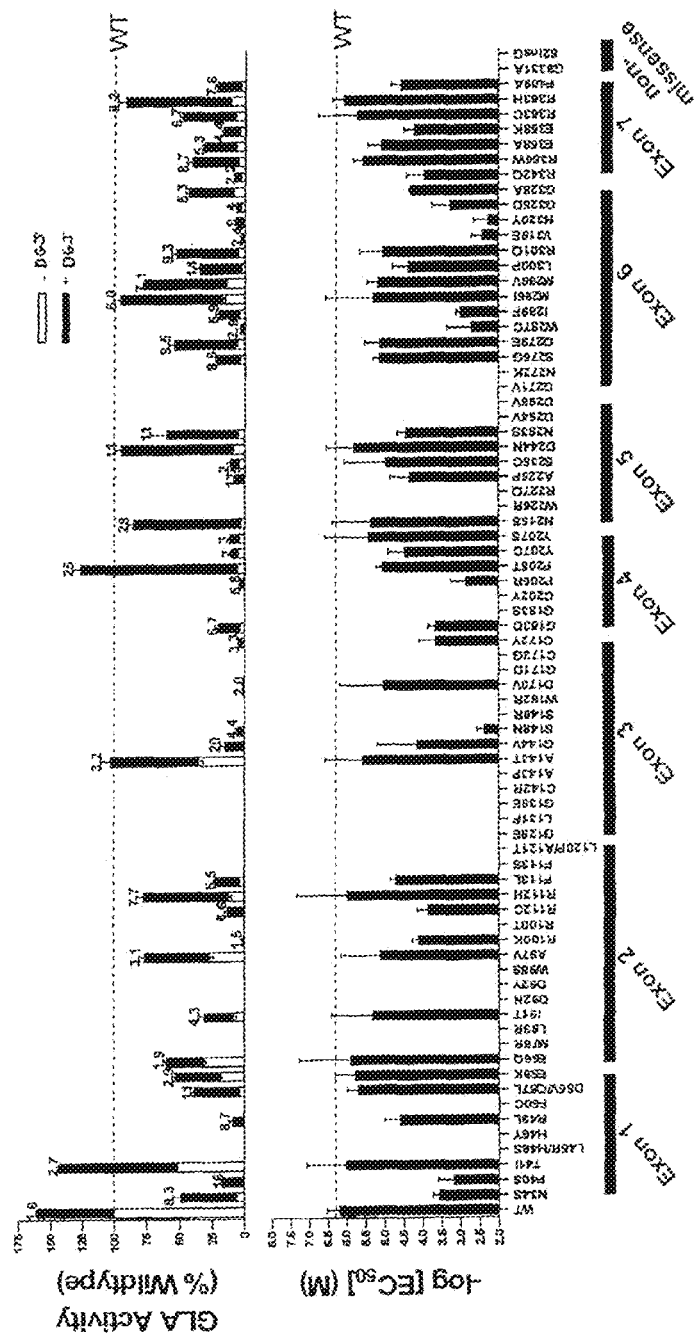
FIG. 26 is a graph of DGJ effect on GLA for various missense mutations as described in Example 8.

Cell lines were constructed to express one of 75 Fabry missense mutations. DGJ was administered to each cell line, and α-GAL activity was measured to determine if DGJ increased the activity of the mutant enzyme. As shown in FIG. 26, DGJ enhanced α-GAL activity in 47 of the 75 cell lines (63%). Furthermore, of the 57 cell lines expressing a Fabry missense mutation associated with "classic" Fabry disease, 34 of the cell lines (60%) exhibited an increase in enzymatic activity following treatment. 20 of the 75 cell lines expressed a missense mutation corresponding to later-onset Fabry disease. Of these 20 cell lines, 19 (95%) displayed an increase in α-GAL activity following treatment.

Figure 27:
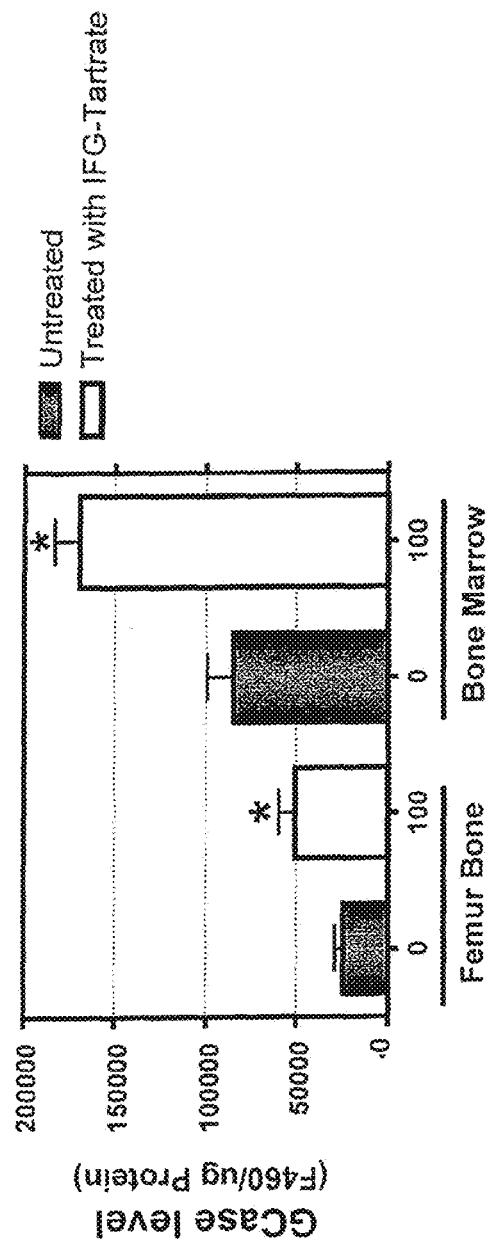
FIG. 27 is a graph of demonstrating Gcase levels in Femur Bone and Bone Marrow as described in Example 9.

Example 9: GCase Response with Isofagomine Tartrate in Bone and Bone Marrow in Normal Mice A single dose of 100 mg/kg of isofagomine tartrate was administered to normal mice. GCase activity (F460/μg protein) was measured in the femur bone and in bone marrow for both the study group and an untreated control group. Results are shown in FIG. 27.

Example 10: Pharmacokinetic/Tissue Distribution of Isofagomine in Rats

Figure 28:
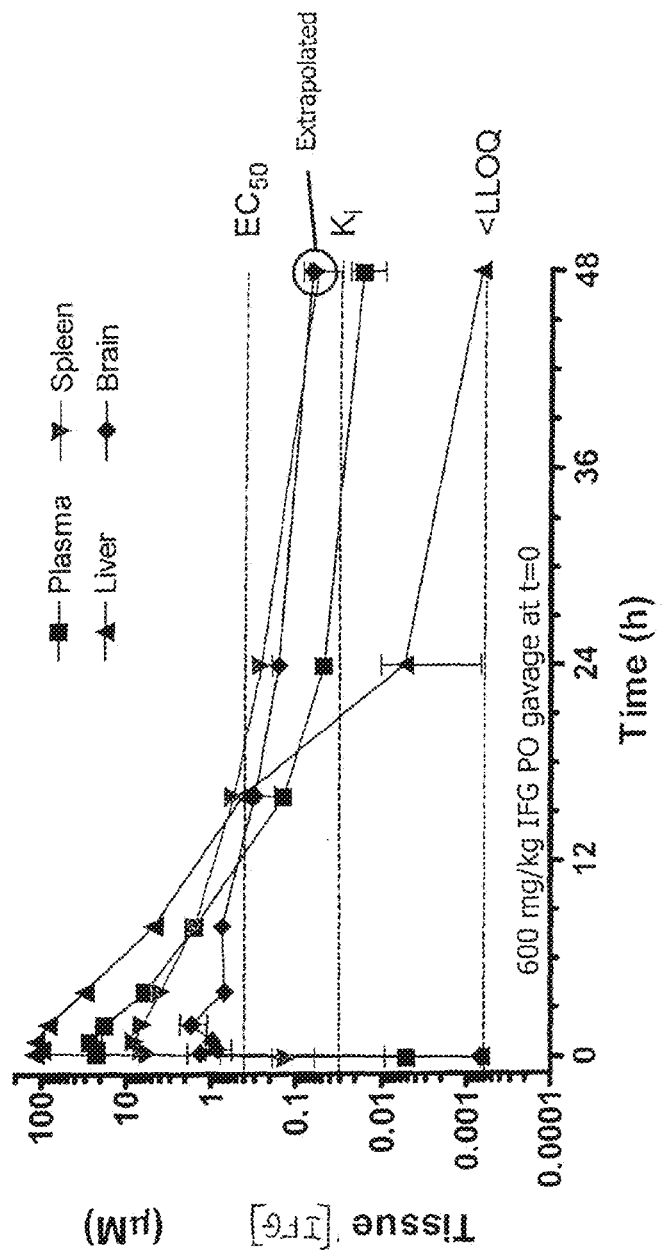
FIG. 28 is a graph demonstrating IFG-tartrate distribution in various tissue over time as described in Example 10.

A single dose of 600 mg/kg of isofagomine was administered to rats via PO gavage. The concentration of isofagomine (μM) in plasma, liver, spleen and brain tissue was ascertained at regular time intervals at dosing (t=0) through 48 hours after dosing. The results are shown in FIG. 28.

All tissues attained isofagomine levels exceeding the GCase enhancement $EC_{50}$ of about 400 μM within 15 minutes. Isofagomine levels fall below the GCASE Ki value after 48 hours in liver and plasma; spleen and brain tissue showed a slower clearance.

Example 11: Comparison of DGJ Dosing Regimens in Male HR301Q GLA Tg/KO Mice

Figure 29:
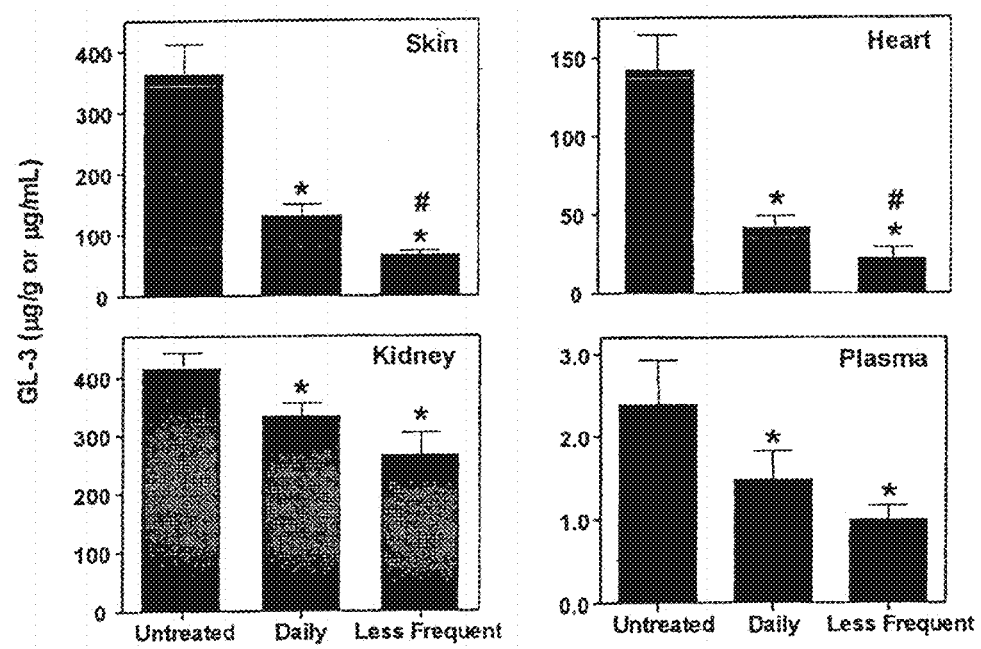
FIG. 29 is a graph comparing GL-3 amounts in rat skin, kidney, heart and plasma samples after 4 weeks of administering DGJ according to the dosing regimens described in Example 11.

Eight-week old male hR301Q GLA Tg/KO mice were treated for 4 weeks with 300 mg/kg of DGJ in drinking water either daily (without washout period) or "less frequent" (4 days on/3 days off). Lysates were prepared from skin, heart, kidney and plasma. GL-3 levels were measured by LC-MS/MS (expressed in mg/g tissue weight or mg/mL plasma). The results are shown in FIG. 29. LC-MS/MS data showed a greater reduction in GL-3 levels (* $p<0.05$ vs. untreated; # $p<0.05$ daily vs. less frequent, t-test) with less frequent DGJ dosing in tissues as well as plasma. Each bar represents the mean±SEM of 10-16 mice/group.

Figure 30:
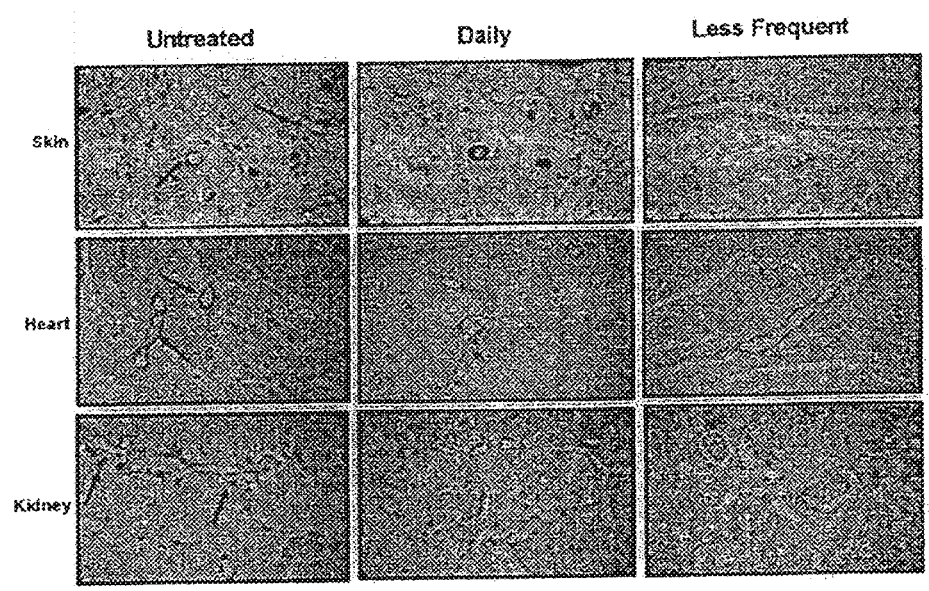
FIG. 30 is a picture of skin, heart and kidney samples that have undergone immunohistochemical staining after 4 weeks of administering DGJ according to the dosing regimens described in Example 11 in order to visually access GL-3 reduction.

Immunohistochemical staining with a monoclonal anti-GL-3 antibody (nuclei counterstained with methyl green) was also performed. Results are shown in FIG. 30 and shows GL-3 signal as dark red/brown spots (black arrows) in skin (fibroblasts and smooth muscle cells of blood vessel wall), heart (smooth muscle cells of blood vessel wall), and kidney (distal tubular epithelial cells). Both daily and "less frequent" DGJ treatment reduced the amount and intensity of GL-3 signal in each tissue (20×). Similar to LC-MS/MS, a greater GL-3 reduction was seen in each tissue with less frequent DGJ dosing. Data shown are representative pictures from 7-8 mice/group.

Example 12: Comparison of DGJ Dosing Amounts in Male HR301Q GLA Tg/KO Mice

Figure 31:
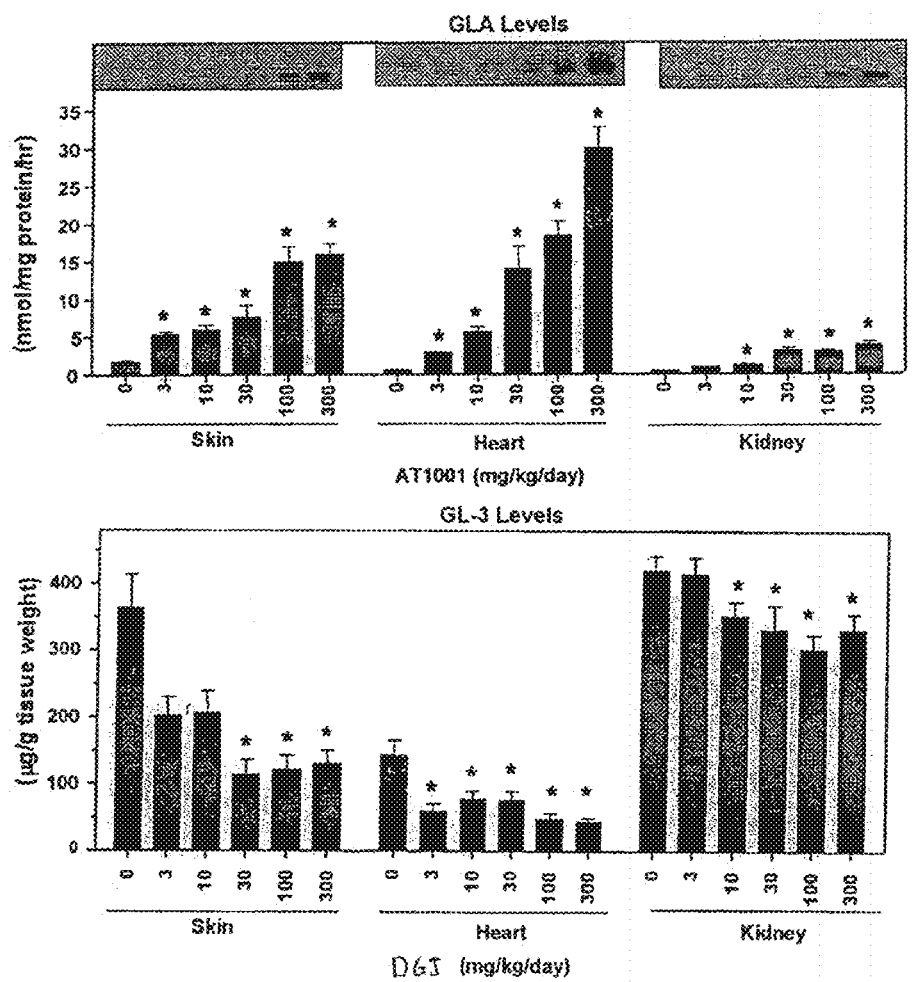
FIG. 31 is graph of GLA and GL-3 levels in rat skin, heart and kidney samples after 4 weeks of administering DGJ according to the dosing regimens described in Example 12.

Eight-week old male hR301Q GLA Tg/KO mice were treated for 4 weeks with 3, 10, 30, 100, or 300 mg/kg/day of DGJ in drinking water. Tissue lysates from skin, heart, and kidney were prepared and tested for GLA activity (using 4-MUG as substrate, expressed in nmol/mg protein/hr), GLA protein (using immunoblotting of 50 mg tissue lysate with anti-human GLA antibody) and GL-3 levels (using LC-MS/MS, expressed in mg/g of tissue weight). Results are shown in FIG. 31. A significant and dose-dependent increase in GLA activity (* $p<0.05$ vs. untreated, ANOVA) and GLA protein (inset, GLA runs as ~45 kD band) and a significant reduction in GL-3 levels (* $p<0.05$ vs. untreated, ANOVA) were seen after DGJ treatment. Each bar represents the mean±SEM of n=7-8 mice/group. Each lane in the Western blots represents one mouse from each group.

Figure 32:
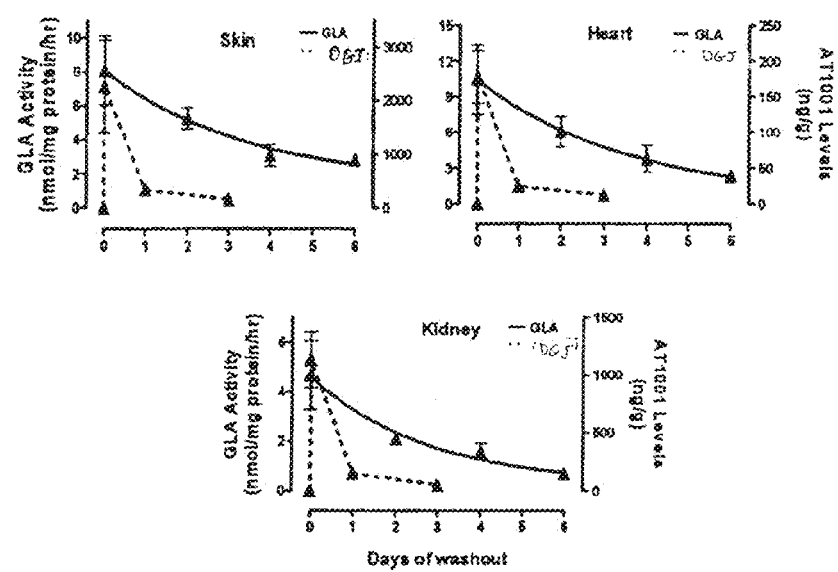
FIG. 32 is a graph of GLA Activity in rat skin, heart, and kidney samples 0 to 7 days after withdrawal from DGJ as described in Example 13.

Example 13: Half-Life Determination of DGJ and Elevated HR301Q GLA in Male HR301Q GLA Tg/KO Mice Half-lives of elevated hR301Q GLA and DGJ were estimated by dosing hR301Q GLA Tg/KO male mice for 4 weeks with 100 mg/kg/day of DGJ (drinking water), followed by 7 day washout (without DGJ in drinking water). Mice were euthanized at 0, 1, 3, 5, and 7 days after DGJ withdrawal and GLA levels (solid line in skin, heart and kidney) were measured using 4-MUG. Concentrations of DGJ were measured by LC-MS/MS (dotted line in skin, heart, and kidney) simultaneously. The results are shown in FIG. 32.

Using exponential decay curves, the half-life of elevated tissue hR301Q GLA levels was estimated as 2-2.5 days, while that of DGJ was estimated at 6-7 hours. Each data point represents the mean±SEM of 6-7 mice/group.

Figure 33:
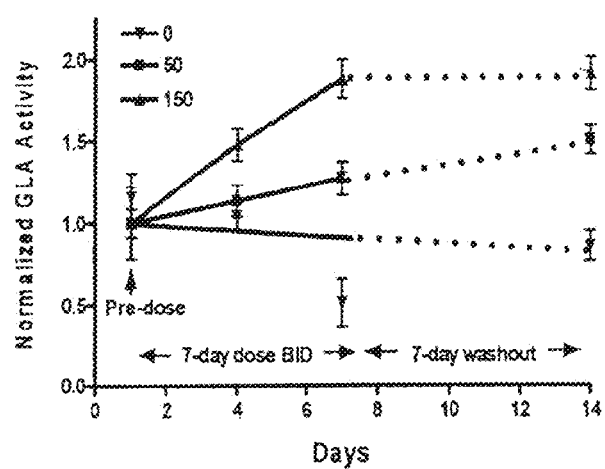
FIG. 33 is a graph of GLA Activity in healthy males during 7 days of twice daily administration of 50 and 150 mg of DGJ, and during a 7-day washout period as described in Example 14.

Example 14: Half-Life Determination of DGJ and Elevated HR301Q GLA in Male HR301Q GLA Tg/KO Mice Oral administration of DGJ to healthy male volunteers (50 and 150 mg twice daily for 7 days; n=6 for treatment groups, n=4 for all placebo) resulted in increased GLA levels, as measured by 4-MUG in white blood cell lysates. DGJ was orally available and was generally well-tolerated at all doses, with no serious adverse events occurring in any treatment group. Data were normalized to the predose values of each group (predose values are 24.6, 23.3, and 14.1 nmoles/mg protein/hr for placebo, 50 and 150 mg respectively). Results are shown in FIG. 33.

Example 15: Dosing Regimens for the Treatment of Fabry Disease Using DGJ Hydrochloride This example describes a study of DGJ (1-deoxygalactonorjirimycin) in Fabry patients.

Patient Enrollment.

Eligible patients were 16-74 years old and had genetically-confirmed Fabry disease, had either never received or had not received enzyme replacement therapy for ≥6-months, had a GLA mutation that resulted in a mutant protein that would respond to DGJ, based on the human embryonic kidney-293 (HEK) assay used at the time of enrollment, had an eGFR>30 ml/minute/1.73 m$^2$, and had a urinary GL-3≥R4 times the upper limit of normal.

Study Design.

Following eligibility-baseline assessments (2-months), patients were randomized to Stage 1—6 months of double-blind administration of 150 mg DGJ HCl or placebo every other day. All patients completing Stage 1 were eligible to receive open-label DGJ in Stage 2 (months 6-12) and for an additional year (months 13-24) thereafter (AT1001-011/NCT00925301). The primary objective was to compare the effect of DGJ to placebo on kidney GL-3 as assessed by histological scoring of the number of inclusions in interstitial capillaries after 6 months of treatment. The secondary objectives of Stage 1 were to compare the effect of DGJ to placebo on urine GL-3 levels, on renal function, 24-hours urinary protein, and on safety and tolerability. The tertiary objectives were cardiac function, patient-reported outcomes, exploratory kidney analyses, and white blood cell α-galactosidase activity. Study completers were eligible to enroll in the open-label study-AT1001-041/NCT01458119—for up to 5 years.

Kidney Histology Assessment.

Each patient underwent a baseline kidney biopsy, as well as repeat kidney biopsies at 6 and 12 months. The number of GL-3 inclusions per kidney interstitial capillary per patient at baseline, and at 6 and 12 months was quantitatively assessed in 300 capillaries by 3 independent pathologists blinded to treatment and visit. All values for each individual biopsy at a given time were averaged prior to statistical analysis.

GL-3 changes in podocytes, endothelial cells, and mesangial cells, and glomerular sclerosis, were assessed qualitatively by the same 3 pathologists blinded to treatment/visit.

Globotriaosylceramide and Globotriaosylsphingosine.

Plasma lyso-Gb3 and 24-hour urine GL-3 were analyzed by liquid chromatography-mass-spectroscopy using a novel stable isotope-labeled internal standard, 13C6-lyso-Gb3 (lower-limit-of-quantification: 0.200 ng/mL, 0.254 nmol/L).

Renal Function Assessment.

Annualized rates of change (mL/min/1.73 m$^2$/year) were calculated using Chronic Kidney Disease Epidemiology Collaboration-eGFRCKD-EPI) and measured iohexol clearance-mGFRiohexol).

Echocardiography.

Left ventricular mass index, left posterior wall thickness, diastolic, interventricular septum thickness, diastolic and other parameters were assessed through blinded, centralized evaluation. The baseline visit of extension study AT1001-041/NCT01458119 was used as the last assessment.

Patient-Reported Outcomes.

Patient-reported outcomes were assessed using the Gastrointestinal-Symptoms-Rating-Scale (GSRS), Short Form-36v2™ and Brief-Pain-Inventory-Pain-Severity-Component.

Safety Analysis and Adverse Events.

Randomized patients receiving ≥1 dose were included in the safety analysis, which comprised vital signs, physical exams, electrocardiograms, clinical labs, and adverse events.

Statistical Analyses for Kidney Interstitial Capillary GL-3 Substrate.

The primary Stage 1 (6 month) endpoint (ITT population with baseline biopsies, n=64) was the proportion of patients in the DGJ and placebo groups with a ≥50% reduction in GL-3 inclusions per interstitial capillary. Two other Stage 1 endpoints were assessed (modified-ITT population: randomized patients with paired baseline and month 6 biopsies; n=60): percent change in GL-3 inclusions per interstitial capillary, and percent of interstitial capillaries with zero GL-3 inclusions.

Efficacy analyses for GL-3 inclusions per interstitial capillary and other pre-specified endpoints in Stage 2 (months 6-12) and the open-label-extension (months 12-24) were based on the modified intention to treat (mITT)—population consisting of randomized patients with mutant α-galactosidase enzyme shown to be suitable for DGJ treatment by the validated assay; n=50).

Results

Baseline Characteristics.

Sixty-seven patients (16-74 years-old; 64% female) with potentially responsive mutant α-galactosidase were randomized (ITT population). Table 6 provides the baseline characteristics for the 50 patients in the ITT population with suitable mutant α-galactosidase. There were no statistically significant differences in baseline parameters.

TABLE 6

| Parameter | DGJ HCl (N = 28) | Placebo to DGJ HCl (N = 22) | Total (N = 50) |
|---|---|---|---|
| Age (year) (n) | 28 | 22 | 50 |
| Mean ± SD | 41.5 ± 13 | 45.1 ± 8.0 | 43.1 ± 11 |
| Median | 37.0 | 45.5 | 45.0 |
| Weight (kg) (n) | 28 | 22 | 50 |
| Mean ± SD | 72.6 ± 15.35 | 76.1 ± 16.52 | 74.1 ± 15.81 |
| Median | 72.3 | 74.0 | 72.8 |
| Number of Years of Diagnosis of Fabry Disease (n) | 28 | 21 | 49 |
| Mean ± SD | 5.6 ± 6.89 | 7.3 ± 8.80 | 6.3 ± 7.73 |
| Median | 4.1 | 4.1 | 4.1 |
| Number of patients previously on ERT (>6-months prior to baseline) (%) | 4 (14.3%) | 7 (31.8%) | 11 (22.0%) |
| Use of ACEi/ARB/Ri at Baseline | | | |
| Yes (%) | 9 (32.1%) | 12 (54.5%) | 21 (42.0%) |
| No (%) | 19 (67.9%) | 10 (45.5%) | 29 (58.0%) |
| Proteinuria >150 mg/24 h (%) | 17 (60.7%) | 18 (81.8%) | 35 (70.0%) |
| Proteinuria >300 mg/24 h (%) | 8 (28.6%) | 11 (50.0%) | 19 (38.0%) |
| Proteinuria >1000 mg/24 h (%) | 3 (10.7%) | 3 (13.6%) | 6 (12.0%) |
| $mGFR_{Iohexol}$ (mL/min/1.73 m$^2$) (n) | 27 | 21 | 48 |
| Mean ± SD | 79.95 ± 30.9 | 83.12 ± 22.8 | 81.34 ± 27.5 |
| Median | 84.90 | 82.20 | 83.40 |
| $eGFR_{CKD-EPI}$ (mL/min/1.73 m$^2$) | 28 | 22 | 50 |
| Mean ± SD | 94.4 ± 27.0 | 90.6 ± 17.1 | 92.7 ± 23.0 |
| Median | 96.6 | 93.5 | 94.0 |
| Lyso-Gb$_3$ (n) | 18 | 13 | 31 |
| Mean (nmol/L) ± SD | 47.3 ± 62 | 41.9 ± 39 | 45.0 ± 53 |

Published reports of clinical phenotype(s) associated with the genotypes of patients with suitable mutations (n=50) indicate that 30 (60%) had mutations associated with the classic phenotype of Fabry disease, one (2%) with the non-classic phenotype, three (6%) with both phenotypes, and 16 (32%) not yet classified. Residual WBC α-galactosidase activity <3% was found in 14 of 16 (87%) males; 29 of 31 (94%) males and females had elevated plasma lyso-Gb3, and 47 of 50 (94%) males and females had multi-organ system disease.

DGJ and Kidney Interstitial Capillary GL-3.

In the 6-month primary outcome analysis (ITT), 13 of 32 (41%) DGJ and 9 of 32 (28%) placebo-treated patients achieved a response (≥50% reduction in GL-3 inclusions per interstitial capillary) (p=0.30). The median change in interstitial capillary GL-3 from baseline was −40.8% for DGJ versus −5.59% for placebo (p=0.097). The mean difference for the change in % of interstitial capillaries with zero GL-3 inclusions was 7.3% in favor of DGJ (p=0.042).

In Stage 1 (6-month post hoc) and Stage 2 (12-month prespecified) analyses (mITT-suitable population; n=45), 6 months of DGJ was associated with a significantly greater reduction in interstitial capillary GL-3 (±SEM) compared to placebo: −0.250±0.103 versus +0.071±0.126; p=0.008. The reduction in interstitial capillary GL-3 at 6 months remained stable following an additional 6 months of treatment. A significant reduction in interstitial capillary GL-3 (±SEM) was observed at 12-months in patients switching from placebo to DGJ at 6 months (−0.330±0.152; p=0.014). Patients with mutant α-galactosidase that was not suitable for DGJ therapy according to the validated assay did not show any treatment effect in interstitial capillary GL-3.

DGJ and GL-3 in Glomerular Cells.

Based on qualitative assessments on 23 kidney biopsies, following 12 months of DGJ, patients with responsive mutant α-galactosidase showed decreases in glomerular podocyte (5 of 23 biopsies; 22%), endothelial cell (6 of 23 biopsies; 26%), and mesangial cell GL-3 (11 of 23 biopsies; 48%). None of the samples had increases; the remaining samples showed no change.

DGJ and Plasma Lyso-Gb3 Levels.

Six months of DGJ (mITT-suitable) was associated with a significant reduction in plasma lyso-Gb3 levels compared to placebo (p=0.0033). Plasma lyso-Gb3 remained stable without further reduction following 6 additional months of DGJ. A significant reduction in plasma lyso-Gb3 was found in patients (ITT-suitable) switching from placebo to DGJ between 6 and 12-months (p<0.0001). Plasma levels in patients with mutant α-galactosidase that was not suitable were unchanged.

DGJ and Urine GL-3 Substrate.

In patients with suitable mutant α-galactosidase, mean changes in 24-hour urine GL-3 substrate (±SEM) concentration for DGJ and placebo (baseline to month 6) were: −361±169 (to 555±151) and −147±217 (to 1017±218) ng/mg creatinine, respectively (p=0.44).

DGJ and Kidney Function.

There were no statistically significant differences between the DGJ and placebo arms in eGFRCKD-EPI, or mGFRIohexol changes from baseline to month 6 (mITT-suitable).

In patients followed for up to 24 months of DGJ (mITT-suitable), the annualized changes in eGFRCKD-EPI and mGFRiohexol (±SEM) were −0.30±6.6, and −1.51±1.33 mL/min/1.73 m$^2$, respectively. Male gender and higher baseline proteinuria were associated with higher rate of annual decline. There were no statistically significant differences in baseline levels or changes from baseline between treatment groups for 24-hour urine protein.

DGJ and Echocardiographic Parameters.

At baseline, left-ventricular-mass-index was comparable between groups with no significant differences in Stage 1.

In patients (ITT-suitable), who received DGJ for up to 24 months, a statistically significant decrease in left-ventricular-mass-index (LVMi) (p<0.05 based on the 95% CI not including 0) was observed overall with a trend toward a larger reduction in patients with baseline LV hypertrophy. Table 7 shows the echocardiographic-derived LVMi changes from baseline to month 18/24 for ITT-suitable patients.

TABLE 7

| Patients with Suitable Mutant α-galactosidase[1] | Baseline[2] Mean ± SEM (g/m²) | Change from Baseline to Month 18/24[3] Mean ± SEM (95% CI) |
|---|---|---|
| All | 96.5 ± 5.0 n = 44 | −7.69 ± 3.7 (−15.4, −0.009)[4] n = 27 |
| Patients with LVH at baseline | 138.9 ± 11 n = 11 | −18.6 ± 8.3 (−38.2, 1.04) n = 8 |

LVMi, Left-ventricular-mass-index (g/m²): Normal: 43-95 (female), 49-115 (male);
LVH, left ventricular hypertrophy;
[1]Includes patients with a baseline and post-baseline ECHO, who received ≥18-months DGJ.
[2]Month 6 used as baseline for placebo patients switching to DGJ; Baseline used if no month 6.
[3]Baseline of extension study used as month 18/24.
[4]Statistically significantly different from baseline based on 95% CIs not overlapping with 0; p < 0.05

Interventricular septal wall thickness decreased by 0.061 cm±0.051 (5.2%) from baseline (1.17 cm±0.057) (95% CI: −1.67, 0.045); the left ventricular posterior wall thickness was stable for up to 24 months. The changes in left-ventricular-mass-index correlated with changes in IVSWT (R2=0.26, p=0.006) but not with changes in left ventricular posterior wall thickness (R2=0.06, p=0.230).

Figure 34:
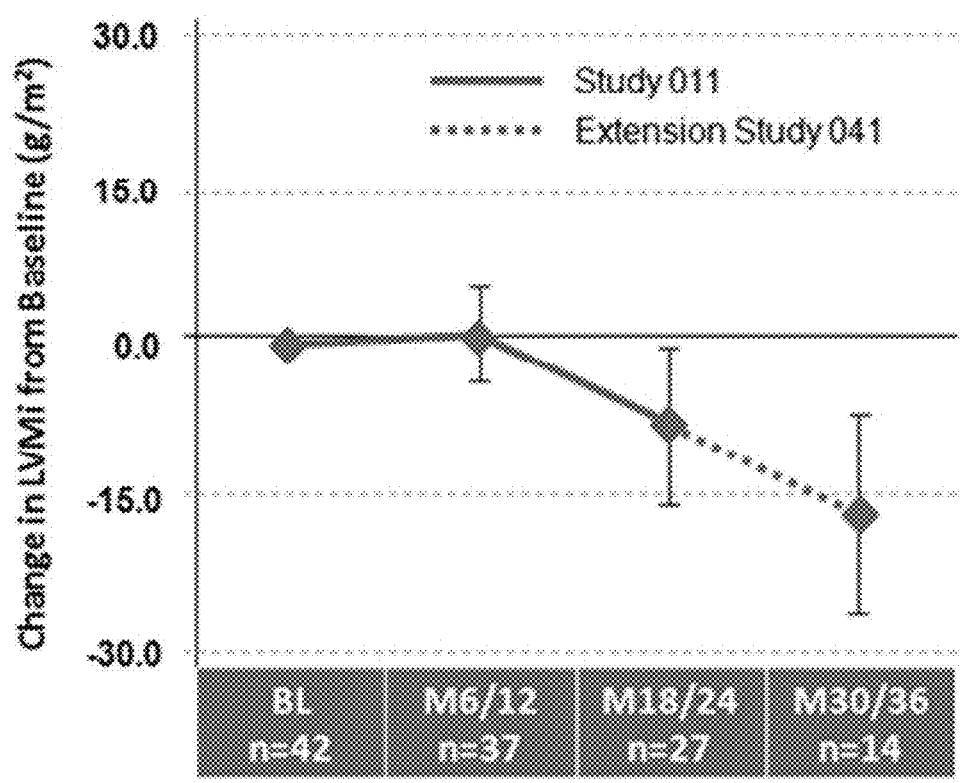
FIG. 34 shows the average LVMi changes from baseline to after 6/12, 18/24 and 30/36 months of DGJ therapy, as described in Example 15.

LVMi continued to decrease over 30/36 months of treatment in an extension of this study [change from baseline (±SD): −7.8 g/m²±21.5]. In patients with baseline LVH (n=4), the change from baseline was larger, −30.0±17.5 g/m². The LVMi changes from baseline to after 6/12, 18/24 and 30/36 months of DGJ therapy are shown in FIG. 34.

Gastrointestinal Symptoms Rating Scale.

Gastrointestinal symptoms improved in 3 of 5 domains (diarrhea, reflux, indigestion) in DGJ-treated ITT-suitable patients, as shown in Table 8 below.

For the diarrhea domain, between baseline and month 6 (Stage 1), there was a statistically significant decrease (p=0.03; ITT-suitable); a nonsignificant decrease was also observed for ITT-suitable patients with baseline symptoms (p=0.06). Statistically significant changes over 24 months were found for ITT-suitable patients and ITT-suitable patients with baseline symptoms (p<0.05, based on the 95% CI not including 0).

There was a statistically significant improvement in the reflux domain in Stage 1 in ITT-suitable patients with baseline symptoms (p=0.047). Statistically significant changes over 24 months were found in the indigestion domain for ITT-suitable patients and ITT-suitable patients with baseline symptoms (p<0.05 based on the 95% CI not including 0). There was a trend toward improvement in the constipation domain.

TABLE 8

Changes in Gastrointestinal Symptoms Rating Scale[1] (ITT-Suitable)

| | \multicolumn{10}{c}{GSRS Domain} |
|---|---|---|---|---|---|---|---|---|---|---|

| | Diarrhea | | Reflux | | Indigestion | | Constipation | | Abdominal Pain | |
|---|---|---|---|---|---|---|---|---|---|---|
| Treatment Group | DGJ | Placebo | DGJ | Placebo | DGJ | Placebo | DGJ | Placebo | DGJ | Placebo |
| Mean Baseline Values (n) | | | | | | | | | | |
| All patients | 2.3 (28) | 2.1 (22) | 1.4 (28) | 1.4 (22) | 2.5 (28) | 2.4 (22) | 1.9 (28) | 2.0 (22) | 2.1 (28) | 2.3 (22) |
| Patients with Symptoms at BL | 3.2 (17) | 3.1 (11) | 2.1 (10) | 2.6 (6) | 2.8 (23) | 2.7 (19) | 2.5 (17) | 2.4 (15) | 2.4 (22) | 2.9 (15) |
| Change from Baseline to Month 6 (Stage 1, Double-Blind) | | | | | | | | | | |
| All Patients | −0.3*[2] | +0.2 | −0.1 | +0.2 | −0.1 | −0.1 | +0.1 | +0.2 | 0.0 | 0.0 |
| Patients with Symptoms at BL | −0.6 | +0.2 | −0.6*[3] | +0.6 | −0.2 | −0.2 | +0.2 | +0.1 | −0.1 | −0.1 |
| Change from Baseline (DGJ) or Month 6 (Placebo) to Month 24 (OLE DGJ Treatment) | | | | | | | | | | |
| All Patients | −0.5 (−0.9, −0.1)*[4] | −0.2 (−0.5, 0.2) | | | −0.4 (−0.7, −0.04)*[4] | −0.4 (−0.7, +0.0)*[5] | | | −0.2 (−0.5, +0.1) | |
| Patients with Symptoms at BL | −1.0 (−1.5, −0.4)*[4] | −0.6 (−1.5, 0.2) | | | −0.5 (−0.8, −0.06)*[4] | −0.5 (−1.1, +0.0)*[5] | | | −0.2 (−0.6, 0.1) | |

*Indicates significant or borderline significant changes from baseline.
[1]Least squares means for change from baseline (BL) |
[2]p = 0.03 and
[3]p = 0.047 using ANCOVA |
[4]Statistically significant or
[5]Trend based on 95% CIs with the upper bound of 0.

DGJ and Podocyte GL-3.

Figure 35:
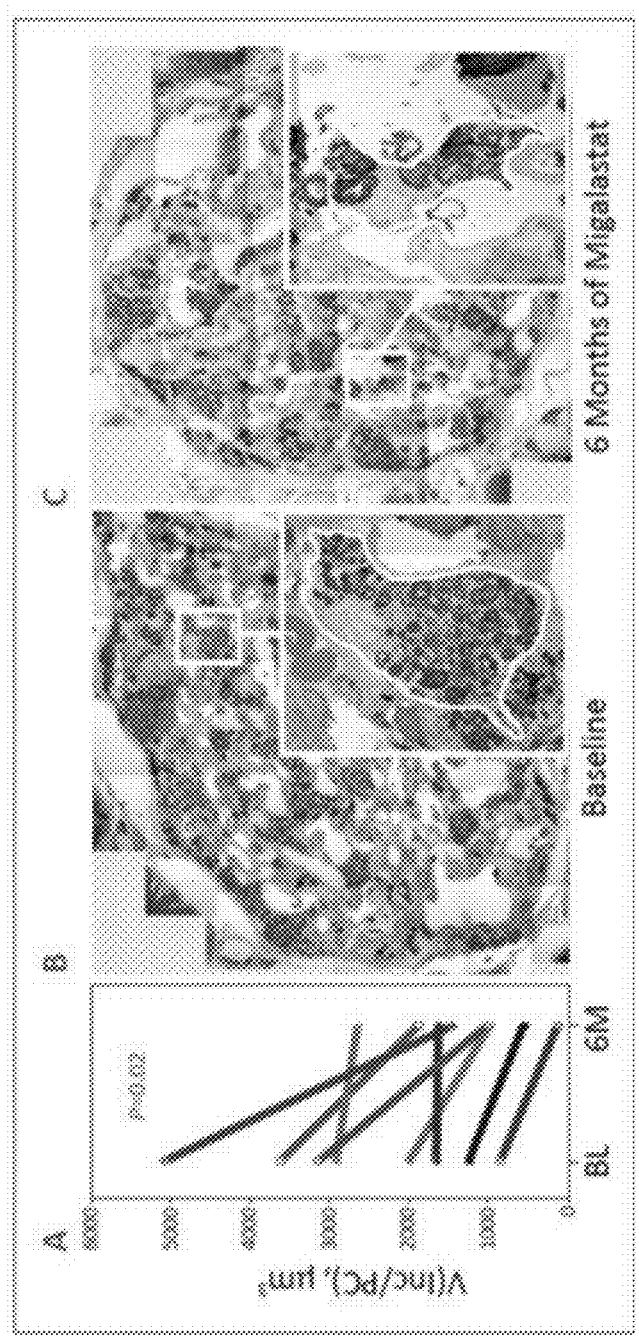
FIG. 35 shows (A) individual changes in GL-3 inclusion volume per podocyte from baseline to after 6 months of DGJ treatment; (B) glomerulus from a patient with Fabry disease at baseline and (C) after 6 months of treatment, as described in Example 15.
Figure 36:
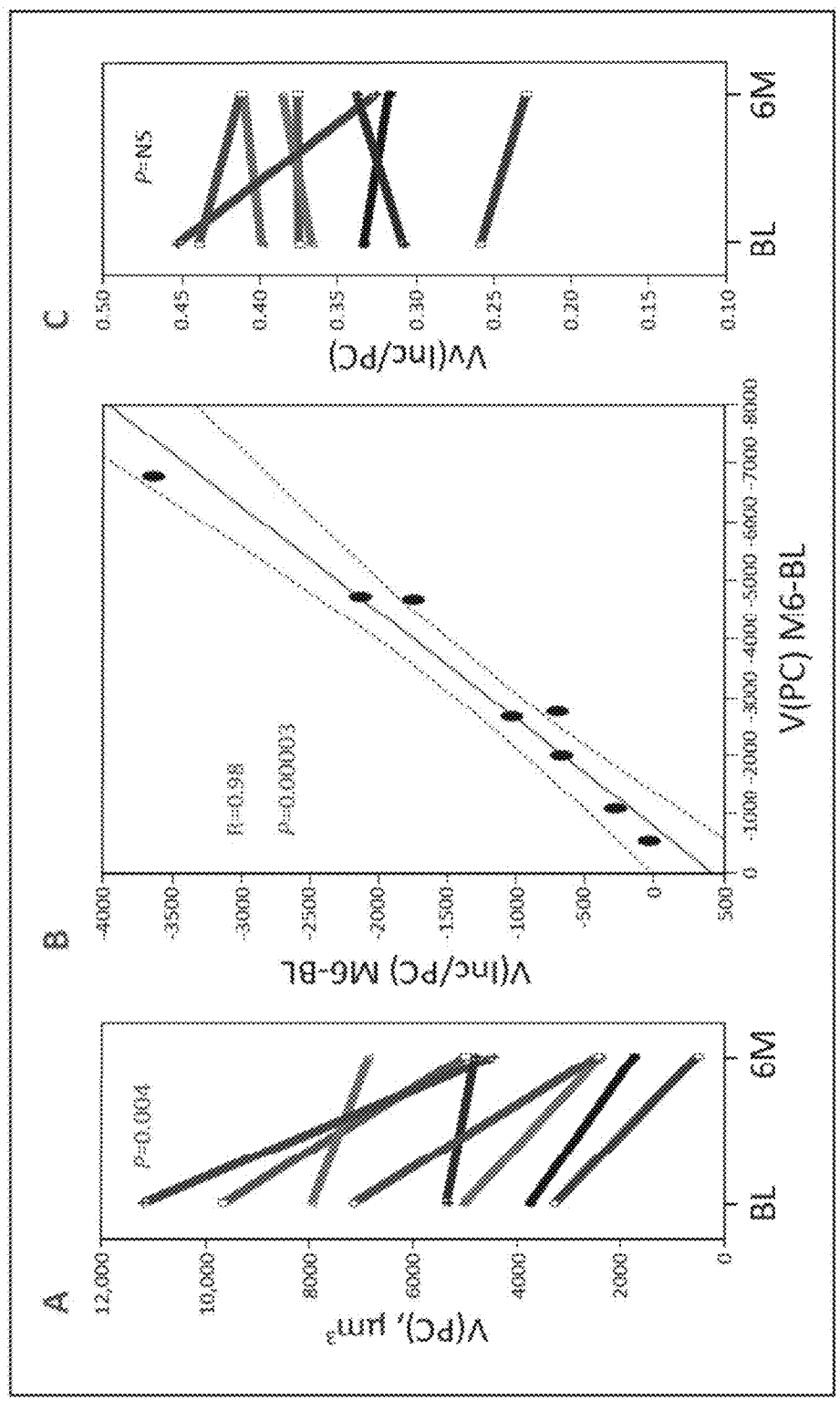
FIG. 36 shows (A) individual changes in podocyte volume from baseline to after 6 months of DGJ treatment; (B) correlation between podocyte volume and podocyte inclusion volume after 6 months of treatment; (C) volume fraction of GL-3 inclusions in podocytes (podocyte inclusion volume/podocyte volume) at baseline and after 6 months of treatment, as described in Example 15.
Figure 37:
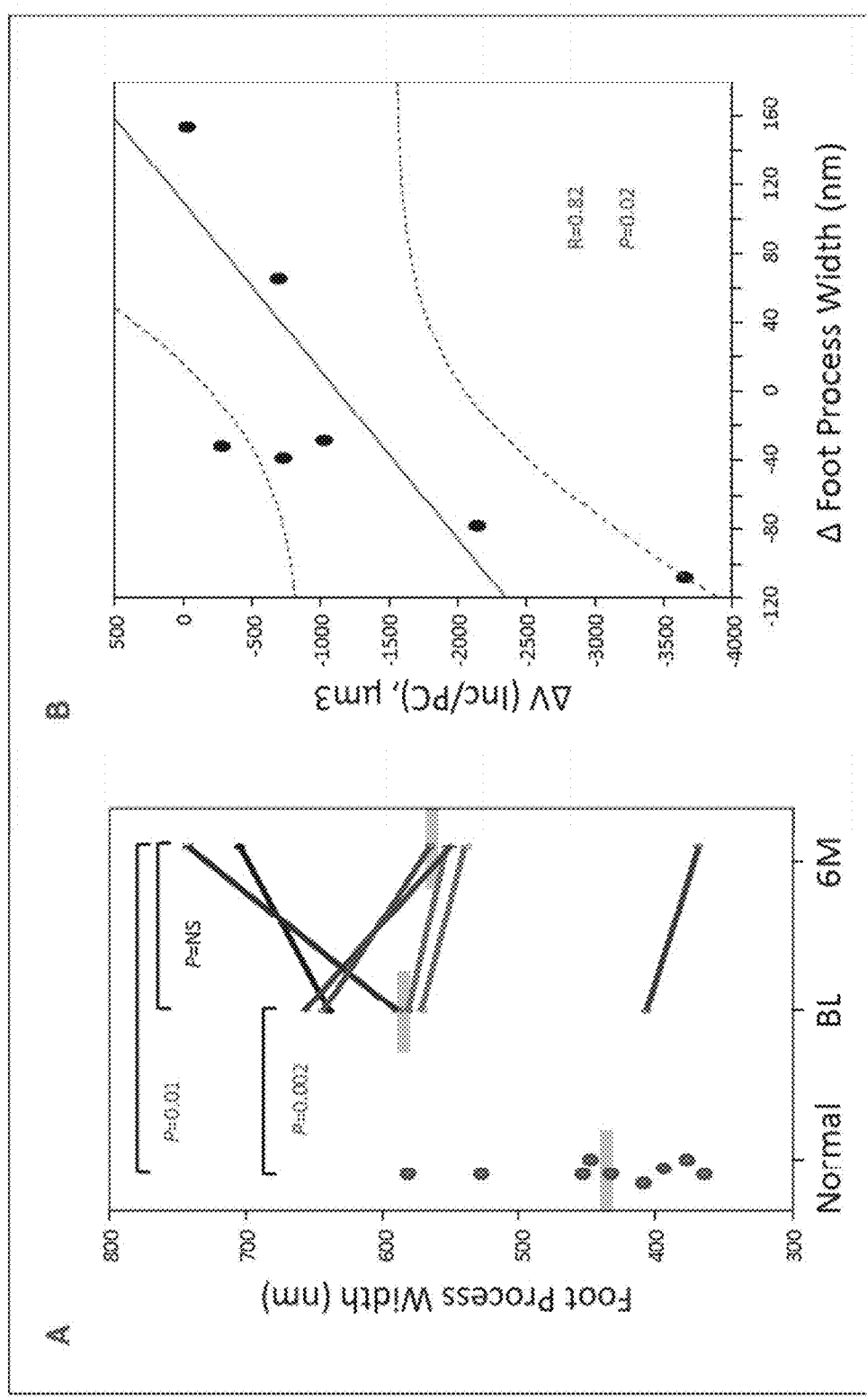
FIG. 37 shows (A) average foot process width in patients with Fabry disease at baseline or after 6 months of DGJ treatment compared with 9 healthy controls; (B) correlation between change in foot process width and change in GL-3 inclusions volume per podocyte, as described in Example 15.
Figure 38:
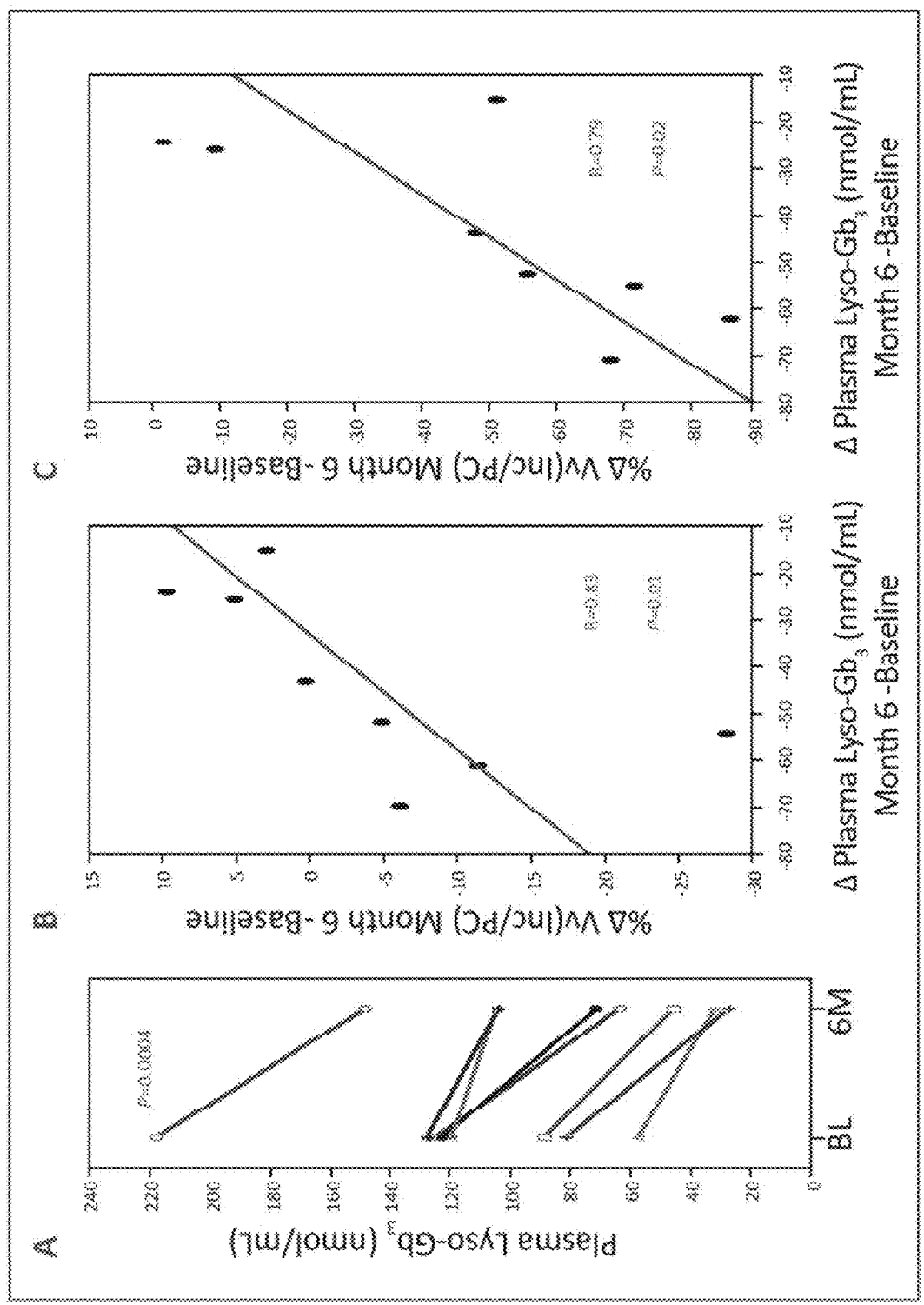
FIG. 38 shows (A) individual changes in plasma lyso-Gb3 from baseline to after 6 months of DGJ treatment; individual comparisons between changes in plasma lyso-Gb3 with (B)

Kidney biopsy samples from enzyme replacement therapy-naïve male patients with Fabry disease with GLA mutations amenable to DGJ (N=8), taken at baseline and again after 6 months of DGJ treatment, were studied by masked unbiased electron microscopy stereology. The mean±SD V(Inc/PC) of all patients decreased from 2568±1408 μm³ at baseline to 1282±792 μm³ after 6 months of DGJ (p=0.0182), as shown in FIG. 35. There was a correlated reduction in mean podocyte volume from 6680±2835 μm³ at baseline to 3525±2084 μm³ (p=0.004) after 6 months of DGJ (r=0.98, p=0.00003), as shown in FIG. 36. These findings indicate that the podocyte cytoplasmic shrinkage was proportional to GL-3 loss; thus, the volume fraction of podocyte cytoplasm attributable to GL-3 did not change significantly. The magnitude of podocyte GL-3 volume reduction following DGJ correlated with improvement of foot process width (r=0.82, p=0.02), as shown in FIG. 37. Mean plasma lyso-Gb3 also decreased from 118±48 nM at baseline to 75±42 nM after 6 months of DGJ (p=0.0004), as shown in FIG. 38. This decrease correlated with % reduction in podocyte GL-3 volume (r=0.79, p=0.02). There was a trend between decrease in podocyte GL-3 volume and proteinuria (r=0.69, p=0.06) following treatment with DGJ for 6 months as shown in FIG. 39, but no association was found with glomerular filtration rate. In this study, DGJ treatment was associated with a loss of GL-3 inclusions in podocytes in patients with Fabry disease. The sensitive quantitative method used can assess treatment efficacy for this important cell type over a relatively short period of time. This method is also more sensitive than the methods described above in the kidney analysis of Example 5 (as shown in FIG. 14), as well as the methods earlier in this example relating to qualitative assessment of podocyte GL-3.

Safety and Adverse Events.

During Stage 1, the treatment-emergent adverse events were similar between groups. Adverse events with a higher frequency in patients receiving DGJ compared to placebo were headache (12/34 patients—35% versus 7/33 patients—21%) and nasopharyngitis (6/34 patients—18% versus 2/34—6%). The most frequently reported adverse events for Stage 2 were headache (9/63 patients—14%) and procedural pain (7/63 patients—11%-related to kidney biopsies) and, for the open-label-extension, proteinuria (9/57 patients—16%), headache (6/57 patients—11%), and bronchitis (6/57 patients—11%). Most adverse events were mild or moderate in severity. No adverse events led to DGJ discontinuation.

Six patients experienced serious adverse events during Stage 1 (2: DGJ; 4: placebo), 5 during Stage 2, and 11 during the open-label-extension. Two serious adverse events were assessed as possibly related to DGJ by the investigator—fatigue and paresthesia. Both occurred in the same patient between months 12-24 and resolved. No individual serious adverse event was reported by >1 patient. Two patients discontinued DGJ due to serious adverse events; both were deemed unrelated to DGJ. No deaths were reported.

Treatment-emergent proteinuria was reported in 9 patients (16%) between months 12-24, and in one case, was judged as DGJ-related. In 5 patients, the 24-month values were in the same range as baseline. Three patients with suitable mutations had overt baseline proteinuria (>1 g/24-hr), which increased over 24-months. In 23/28 patients with baseline proteinuria <300 mg/24-h, 24-hour urine protein remained stable during DGJ treatment.

There was no progression to end-stage renal disease, no cardiac death and no stroke as defined in Banikazemi et al. There was a single case of transient ischemic attack—judged unrelated to DGJ.

Analyses of vital sign, physical findings, laboratory, and ECG parameters did not reveal any clinically relevant effect of DGJ.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

It is further to be understood that all values are approximate, and are provided for description.

Patents, patent applications, publications, product descriptions, and protocols are cited throughout this application, the disclosures of which are incorporated herein by reference in their entireties for all purposes.

What is claimed is:

1. A method for treatment of Fabry disease in a human patient in need thereof, the method comprising administering to the patient a therapeutically effective dose of 1-deoxygalactonojirimycin or a salt thereof, wherein the therapeutically effective dose provides one or more of:
   a. a mean maximum drug plasma concentration ($C_{max}$) bioequivalent to about 9 µM;
   b. a mean time to maximum drug plasma concentration ($T_{max}$) bioequivalent to about 3 hours; or
   c. a mean drug plasma half-life ($t_{1/2}$) bioequivalent to about 3 hours,
wherein the 1-deoxygalactonojirimycin or salt thereof is administered every other day.

2. The method of claim 1, wherein the 1-deoxygalactonojirimycin or salt thereof is administered as an oral dosage form.

3. The method of claim 2, wherein the oral dosage form comprises a tablet, a capsule or a solution.

4. The method of claim 1, wherein the 1-deoxygalactonojirimycin or salt thereof enhances α-galactosidase A activity.

5. The method of claim 1, wherein the patient is male.

6. The method of claim 1, wherein the patient is female.

7. The method of claim 1, wherein the therapeutically effective dose provides a $C_{max}$ bioequivalent to about 9 µM.

8. The method of claim 1, wherein the therapeutically effective dose provides a $T_{max}$ bioequivalent to about 3 hours.

9. The method of claim 1, wherein the therapeutically effective dose provides a $t_{1/2}$ bioequivalent to about 3 hours.

10. A method for treatment of Fabry disease in a human patient in need thereof, the method comprising administering to the patient a therapeutically effective dose of 1-deoxygalactonojirimycin or a salt thereof, wherein the therapeutically effective dose provides one or more of:
   a. a mean maximum drug plasma concentration ($C_{max}$) within 20% of 9 µM;
   b. a mean time to maximum drug plasma concentration ($T_{max}$) within 20% of 3 hours; or
   c. a mean drug plasma half-life ($t_{1/2}$) within 20% of 3 hours,
wherein the 1-deoxygalactonojirimycin or salt thereof is administered every other day.

11. The method of claim 10, wherein the 1-deoxygalactonojirimycin or salt thereof is administered as an oral dosage form.

12. The method of claim 11, wherein the oral dosage form comprises a tablet, a capsule or a solution.

13. The method of claim 10, wherein the 1-deoxygalactonojirimycin or salt thereof enhances α-galactosidase A activity.

14. The method of claim 10, wherein the patient is male.

15. The method of claim 10, wherein the patient is female.

16. The method of claim 10, wherein the therapeutically effective dose provides a $C_{max}$ within 20% of 9 µM.

17. The method of claim 10, wherein the therapeutically effective dose provides a $T_{max}$ within 20% of 3 hours.

18. The method of claim 10, wherein the therapeutically effective dose provides a $t_{1/2}$ within 20% of 3 hours.

* * * * *